(12) United States Patent
Weichselbaum et al.

(10) Patent No.: US 8,034,791 B2
(45) Date of Patent: Oct. 11, 2011

(54) ACTIVATION OF EGR-1 PROMOTER BY DNA DAMAGING CHEMOTHERAPEUTICS

(75) Inventors: Ralph R. Weichselbaum, Chicago, IL (US); Donald W. Kufe, Wellesley, MA (US); Mitchell Posner, Chicago, IL (US); Helena Mauceri, Wheaton, IL (US); James O. Park, New York, NY (US)

(73) Assignees: The University of Chicago, Chicago, IL (US); Dana-Farber Cancer Institute, Boston, MA (US)

( * ) Notice: Subject to any disclaimer, the term of this patent is extended or adjusted under 35 U.S.C. 154(b) by 902 days.

(21) Appl. No.: 11/467,799

(22) Filed: Aug. 28, 2006

(65) Prior Publication Data

US 2007/0036748 A1  Feb. 15, 2007

Related U.S. Application Data

(63) Continuation-in-part of application No. 10/117,442, filed on Apr. 5, 2002, now abandoned, and a continuation-in-part of application No. 10/795,090, filed on Mar. 5, 2004, now abandoned.

(60) Provisional application No. 60/282,040, filed on Apr. 6, 2001, provisional application No. 60/452,489, filed on Mar. 6, 2003.

(51) Int. Cl.
*A61K 48/00* (2006.01)
*A01N 63/00* (2006.01)
*A01N 65/00* (2009.01)
*C12N 5/07* (2010.01)
*C12N 5/10* (2006.01)
*C07H 21/02* (2006.01)
*C07H 21/04* (2006.01)

(52) U.S. Cl. ............... 514/44 R; 424/93.1; 424/93.2; 435/355; 536/23.1; 536/23.5; 536/24.1

(58) Field of Classification Search .................. None
See application file for complete search history.

(56) References Cited

U.S. PATENT DOCUMENTS

| 633,626 | A | 9/1899 | Stone |
|---|---|---|---|
| 4,201,767 | A | 5/1980 | Fullerton et al. |
| 4,370,417 | A | 1/1983 | Hung et al. |
| 4,415,732 | A | 11/1983 | Caruthers et al. |
| 4,458,066 | A | 7/1984 | Caruthers et al. |
| 4,554,101 | A | 11/1985 | Hopp |
| 4,587,055 | A | 5/1986 | Regen |
| 4,664,911 | A | 5/1987 | Uhr et al. |
| 4,677,063 | A | 6/1987 | Mark et al. |
| 4,677,064 | A | 6/1987 | Mark et al. |
| 4,684,611 | A | 8/1987 | Schilperoort et al. |
| 4,769,331 | A | 9/1988 | Roizman et al. |
| 4,792,447 | A | 12/1988 | Uhr et al. |
| 4,797,368 | A | 1/1989 | Carter et al. |
| 4,833,080 | A | 5/1989 | Brent et al. |
| 4,835,098 | A | 5/1989 | Orr et al. |
| 4,952,500 | A | 8/1990 | Finnerty et al. |
| 5,045,451 | A | 9/1991 | Uhr et al. |
| 5,128,126 | A | 7/1992 | Boniver |
| 5,139,941 | A | 8/1992 | Muzyczka et al. |
| 5,176,617 | A | 1/1993 | Fischell et al. |
| 5,206,152 | A | 4/1993 | Sukhatme |
| 5,252,479 | A | 10/1993 | Srivastava |
| 5,264,618 | A | 11/1993 | Felgner et al. |
| 5,288,641 | A | 2/1994 | Roizman |
| 5,302,523 | A | 4/1994 | Coffee et al. |
| 5,322,783 | A | 6/1994 | Tomes et al. |
| 5,354,855 | A | 10/1994 | Cech et al. |
| 5,359,046 | A | 10/1994 | Capon et al. |
| 5,384,253 | A | 1/1995 | Krzyzek et al. |
| 5,464,765 | A | 11/1995 | Coffee et al. |
| 5,538,877 | A | 7/1996 | Lundquist et al. |
| 5,538,880 | A | 7/1996 | Lundquist et al. |
| 5,550,318 | A | 8/1996 | Adams et al. |

(Continued)

FOREIGN PATENT DOCUMENTS

AU  657111  6/1995

(Continued)

OTHER PUBLICATIONS

Bold, R.J., et al., "Gemcitabine-Induced Programmed Cell Death (Apotosis) of Human Pancreatic Carcinoma Is Determined by Bcl-2 Content" Annals of Surgical Oncology, (Jun. 1999), vol. 6, No. 3, pp. 279-285.*

Fritzell, J.A. et al., "Role of DNA mismatch repair in the cytotoxicity of ionizing radiation," Cancer Research (1997) 57:5143-5147.

Arai, M. et al., "Mechanism of doxorubicin-induced inhibition of sarcoplasmic reticulum C12+-ATPase gene transcription," Cir. Res. (2000) 86(1):8-14.

Joki, T. et al., "Modification of doxorubicin molecule enhanced the early growth response gene 1 promoter activity," Jikeikai Med. J. (1996) 43(1):1-7.

(Continued)

*Primary Examiner* — Robert M Kelly
(74) *Attorney, Agent, or Firm* — Andrus, Sceales, Starke & Sawall, LLP

(57) ABSTRACT

The present invention relates to methods of inducing expression of a polynucleotide encoding a therapeutic polypeptide, e.g., TNF-α, in a cell comprising contacting the cell with a construct comprising an Egr-1 promoter operably linked to a polynucleotide encoding the polypeptide, and at least one chemotherapeutic agent, wherein the chemotherapeutic agent induces expression of the polypeptide. The invention also relates to methods of inhibiting a neoplastic cell, comprising contacting the cell with a construct comprising an Egr-1 promoter operably linked to a polynucleotide encoding TNF-α and a chemotherapeutic agent. The present invention further relates to methods of inhibiting or reducing the growth of a tumor in a subject, comprising co-administering to the subject a construct comprising an Egr-1 promoter operably linked to a polynucleotide encoding TNF-α and a chemotherapeutic agent, wherein the co-administration inhibits or reduces the ability of the tumor to grow.

33 Claims, 18 Drawing Sheets

U.S. PATENT DOCUMENTS

| | | | |
|---|---|---|---|
| 5,563,055 | A | 10/1996 | Townsend et al. |
| 5,571,797 | A * | 11/1996 | Ohno et al. .................... 514/44 |
| 5,578,706 | A | 11/1996 | Ghetie et al. |
| 5,580,859 | A | 12/1996 | Felgner et al. |
| 5,589,466 | A | 12/1996 | Felgner et al. |
| 5,591,616 | A | 1/1997 | Hiei et al. |
| 5,610,042 | A | 3/1997 | Chang et al. |
| 5,612,318 | A | 3/1997 | Weichselbaum et al. |
| 5,652,095 | A | 7/1997 | Taniguchi et al. |
| 5,656,610 | A | 8/1997 | Shuler et al. |
| 5,672,344 | A | 9/1997 | Kelley et al. |
| 5,686,072 | A | 11/1997 | Uhr et al. |
| 5,702,932 | A | 12/1997 | Hoy et al. |
| 5,736,524 | A | 4/1998 | Content et al. |
| 5,759,566 | A | 6/1998 | Poli et al. |
| 5,762,904 | A | 6/1998 | Okada et al. |
| 5,767,072 | A | 6/1998 | Vitetta et al. |
| 5,770,581 | A | 6/1998 | Weichselbaum et al. |
| 5,780,448 | A | 7/1998 | Davis et al. |
| 5,789,215 | A | 8/1998 | Berns et al. |
| 5,795,715 | A | 8/1998 | Livache et al. |
| 5,817,636 | A | 10/1998 | Weichselbaum et al. |
| 5,871,727 | A | 2/1999 | Curiel |
| 5,889,136 | A | 3/1999 | Scaringe et al. |
| 5,925,565 | A | 7/1999 | Berlioz et al. |
| 5,935,819 | A | 8/1999 | Eichner et al. |
| 5,935,935 | A | 8/1999 | Connelly et al. |
| 5,945,100 | A | 8/1999 | Fick |
| 5,981,274 | A | 11/1999 | Tyrrell et al. |
| 5,994,136 | A | 11/1999 | Naldini et al. |
| 5,994,624 | A | 11/1999 | Trolinder et al. |
| 6,013,516 | A | 1/2000 | Verma et al. |
| 6,066,624 | A | 5/2000 | Woo et al. |
| 6,069,757 | A * | 5/2000 | Arai et al. .................... 360/8 |
| 6,143,290 | A | 11/2000 | Zhang et al. |
| 6,156,736 | A | 12/2000 | Weichselbaum et al. |
| 6,228,356 | B1 | 5/2001 | Glorioso et al. |
| 6,524,832 | B1 | 2/2003 | Kufe et al. |
| 6,605,712 | B1 | 8/2003 | Weichselbaum et al. |
| 6,899,870 | B1 | 5/2005 | McDonnell et al. |
| 7,041,653 | B2 * | 5/2006 | Weichselbaum et al. ....... 514/44 |
| 7,214,368 | B2 * | 5/2007 | Rasmussen et al. ......... 424/93.1 |
| 2001/0006954 | A1 | 7/2001 | Weichselbaum et al. |
| 2003/0082685 | A1 | 5/2003 | Weichselbaum et al. |
| 2004/0242523 | A1 | 12/2004 | Weichselbaum et al. |

FOREIGN PATENT DOCUMENTS

| | | |
|---|---|---|
| EP | 0273085 | 7/1988 |
| EP | 0662137 | 5/2005 |
| WO | WO 92/11033 | 12/1991 |
| WO | WO 92/17598 | 10/1992 |
| WO | WO 94/06916 | 3/1994 |
| WO | WO 94/09699 | 5/1994 |
| WO | WO 95/06128 | 3/1995 |
| WO | WO 95/27071 | 10/1995 |
| WO | WO 96/33280 | 10/1996 |
| WO | 99/27908 | 6/1999 |
| WO | WO 99/32619 | 7/1999 |
| WO | WO 99/65515 | 12/1999 |
| WO | WO 00/44914 | 8/2000 |
| WO | WO 01/36646 | 5/2001 |
| WO | WO 01/68836 | 9/2001 |
| WO | WO 02/083653 | 10/2002 |

OTHER PUBLICATIONS

Ohba, M. et al., "Production of hydrogen peroxide by transforming growth factor-beta-1 and its involvement in induction of egr-1 in mouse osteoblastic cells," J. Cell Biol. (1994) 126(4)1079-1088.

Yu, J. et al., "Coactivating factors p300 and CBP are transcriptionally crossregulated by Egr1 in prostate cells, leading to divergent responses," Molecular Cell (2004) 15:83-94 0.

Abate et al., "Redox regulation of Fos and Jun DNA-binding activity in vitro," Science (1990) 249:1157-1161.

Abou-Shoer et al., "Flavonoids from Koelreuteria Henryi and other sources as protein-tyrosine kinase inhibitors," J. Nat. Proc. (1993) 56(6):967-969.

Advani, S. et al., "Enhancement of replication of genetically engineered herpes simplex virus by ionizing radiation: a new paradigm for destrubtion of intractable tumors," Gene Therapy (1998) 5:160-165.

Ainsworth, E.J. and Chase, H.B., "Effect of microbial antigens on irradiation mortality in ice," Proc. Soc. Exp. Biol. Med. (1959) 102:483-485.

Al-Khodiary and Carr, "DNA repair mutants defining G2 checkpoint pathways in *Schizosaccharomyces pombe*," The EMBO Journal (1992) 11(4):1343-1350.

Alberts et al., "A eucaryotic gene control region consists of a promoter plus regulatory DNA sequences," Molecular Biology of the Cell (3rd Ed.) 423.

Alexander et al., "Isolated hepatic perfusion with tumor necrosis factor and melphalan for unresectable cancers confined to the liver," J. Clin. Oncol. (1998) 16:1479-1489.

Alexandropoulos, K. et al., "v-Fps-responsiveness in the Egr-1 Promoter is Mediated by Serum Response Elements," Nucleic Acids Research (1992) 20(9):2355-2359.

Andrews, G.K. et al., "The heat shock response in HeLa cells is accompanied by elevated expression of the c-fos proto-oncogene," Mol. Cell. Biol. (1987) 7:3452-3458.

Angel, P. et al., "Induction of metallothionein and other mRNA species by carcinogens and tumor promoters in primary human skin fibroblasts," Mol. Cell Biol. (1986) 6:1760-1766.

Angel, P. et al., "12-O-Tetradecanoyl-phorbol-13-acetate induction of the human collagenase gene is mediated by an inducible enhancer element located in the 5'-flanking region," Mol. Cell Biol. (1987) 7:2256-2266.

Angel, P. et al., "Oncogene jun encodes a sequence-specific trans-activator similar to AP-1," Nature (1988) 332:166-171.

Angel et al., "The jun proto-oncogene is positively autoregulated by its product, Jun/AP-1," Cell (1988) 55:875-885.

Arai et al., "Cytokines: Coordinators of immune and inflammatory responses," Ann. Rev. Biochem. (1990) 59:783-836.

Arap et al., "Replacement of the p16/DCKN2 gene supresses human glioma cell growth," Cancer Res. (1995) 55:1351-1354.

Atherton-Fessler et al., "Mechanisms of p34cdc2 regulation," Molecular and Cellular Biology (1993) 13(3):1675-1685.

Attar et al., "Expression cloning of a novel zinc finger protein that binds to the c-fos serum response element," Molecular and Cellular Biol. (1992) 12(5):2432-2443.

Ausubel et al., *Current Protocols in Molecular Biology*, John Wiley and Sons, Inc., (1994).

Baichwal, V.R. and Tjian, R., "Control of c-Jun activity by interaction of a cell-specific inhibitor with regulatory domain δ: differences between v- and c-Jun," Cell(1990) 63:815-825.

Baichwal, V.R. et al., "v-SRC and EJ Ras alleviate repression of c-Jun by a cell-specific inhibitor," Nature(1991)352:165-168.

Baichwal, V.R. and Sugden, B., "Vectors for gene transfer derived from animal DNA viruses: transient and stable expression of transferred genes," Gene Transfer, Kucherlapati R., ed., New York, Plenum Press, (1986) 117-148.

Bajorin et al., "Phase I Trial of Anti-GD 3 Mouse Monoclonal Antibody (Mab) and IL-2 in Patients with Melanoma," Proc. Annu. Meet. Am. Soc. Clin. Oncol., (1988) 7:A967.

Ballard, "The 65-kDa subunit of human NF-kB functions as a potent transcriptional activator and a target for v-Rel-mediated repression," Proc. Natl. Acad. Sci USA(1992) 89:1875-1879.

Barbet and Carr, "Fission yeast wee1 protein kinase is not required for DNA damage-dependent mitotic arrest," Nature (1993) 364:824-827.

Bates, "Genetic transformation of plants by protoplast electroporation," Mol. Biotechnol., (1994) 2(2):135-145.

Battraw and Hall, "Stable transformation of sorghum-bicolor protoplasts with chimeric neomycin phosphotransferase II and beta glucuronidase genes," Theor. App. Genet. (1991) 82(2):161-168.

Baumann et al., "Response of xenografts of human malignant gliomas and squamous cell carcinomas to fractionated irradiation," J. Radiation Oncology Biol. Phys. (1992) 23(4):803-809.

Becker et al., "Recombinant tissue-type plasminogen activator: Current concepts and guidelines for clinical use in acute myocardial infarction. Part I," Am. Heart J. (1991) 220-244.

Bedzyk, et al., "Immunological and structural characterization of a high affinity anti-fluorescein single-chain antibody," J. Biol. Chem. (1990) 265:18615-18620.

Benvenisty and Reshif, "Direct introduction of genes into rats and expression of the genes," Proc. Natl. Acad. Sci. USA (1986) 83(24):9551-9555.

Berkner, K. L., "Development of Adenovirus Vectors for the Expression of Heterologous Genes," BioTechniques (1988) 6(7):616-629.

Bernstein, L.R. and Colburn, N.H., "AP1/jun function is differentially induced in promotion-sensitive and resistant JB6 cells," Science(1989) 244:566-569.

Bernstein, S.H. et al., "Post-transcriptional regulation of the zinc finger-encoding EGR-1 gene by granulocyte-macrophage colony-stimulating factor in human U-937 monocytic leukemia cells: involvement of a pertussis toxin-sensitive G protein," Cell Growth & Differentiation (1991) 2:273-278.

Beutler and Cerami, "Tumor necrosis, cachexia, shock and inflammation: a common mediator," Ann. Rev. Biochem. (1988) 57:505-518.

Bevilacqua, M.P. et al., "Endothelial leukocyte adhesion molecule 1: an inducible receptor for neutrophils related to complement regulatory proteins and lectins," Science(1989) 243:1160-1165.

Bhattacharjee and Gupta, "Fertile transgenic indica rice produced by expression of maize ubiquitin promoter-bar chimaeric gene in the protoplasts," J. Plant Bioch. and Biotech. (1997) 6(2):69-73.

Bhuyan et al., "Lethality, DNA alkylation, and cell cycle effects of adozelesin (U-73975) on rodent and human cells," Cancer Research (1992) 52:5687-5692.

Binetruy, B. et al., "Ha-Ras augments c-Jun activity and stimulates phosphorylation of its activation domain," Nature(1991) 351:122-127.

Blaese, M. et al., "Vectors in cancer therapy: how will they deliver?" Cancer Gene Therapy (1995) 2(4):291-297.

Blaese et al., "T Lymphocyte-directed gene therapy for ADA-SCID: Initial trial results after 4 years," Science (1995) 270:475-479.

Blomer et al., "Highly efficient and sustained gene transfer in adult neurons with a lentiviral vector," J. Virol. (1997) 71(9):6641-6649.

Bohmann et al., Science (1987) 238:1386-1392.

Bonavida et al., "Synergy is document in vitro with low-dose recombinant tumor necrosis factor, cisplatin, and doxorubicin in ovarian cancer cells," Gynecol. Oncol. (1990) 38:333-339.

Bonthron et al., "Platelet-derived growth factor A chain: gene structure, chromosomal location, and basis for alternative mRNA splicing," Proc. Natl. Acad. Sci. USA (1988) 85:1492-1496.

Bonura, T. and Smith, K.C., "The involvement of indirect effects in cell-killing and DNA double-strand breakage in γ-irradiated *Escherichia coli* K-12," Int. J. Radiat. Biol. (1976) 29:293-296.

Boothman, D.A. et al., "Identification and characterization of x-ray-induced proteins in human cells," Cancer Research (1989) 49:2871-2878.

Borek, "The induction and control of radiogenic transformation in vitro: cellular and molecular mechanisms," Pharmacol. Ther. (1985) 27:99-142.

Bosher, J.M. and Labouesse, M., Nat. Cell Biol. (2000) 2:E31-E36.

Brach, M.A. et al., "Ionizing radiation induces expression and binding activity of the nuclear factor κB," The American Soc. for Clinical Invest. Inc. (1991) 88:691-695.

Braddock, "The transcription factor Egr1: a potential drug in wound healing and tissue repair," Ann. Med. (2001) 33:313-318.

Breakefield et al., "Herpes simplex virus for gene delivery to neurons," New Biologist (1991) 3:203-218.

Brenner et al., Nature (1989) 337(6208):661-663.

Brott, T., Cerebrovase Brain Metab.(1991) 3:91-113.

Brown et al., J. Immunother. (1991) 10:376-378.

Brown, D. "Gene therapy 'oversold' by researchers, journalists," The Washington Post (1995) A1, A22.

Bryant et al., "Tissue repair with a therapeutic transcription factor," Human Gene Ther. (2000) 11:2143-2158.

Buchdunger et al., "4,5-Dianilinophthalimide: A protein-tyrosine kinase inhibitor with selectivity for the epidermal growth factor receptor signal transduction pathway and potent in vivo antitumor activity," Proc. Natl. Acad. Sci. USA (1994) 91:2334-2338.

Budach et al, "The TCD50 and regrowth delay assay in human tumor xenografts: differences and implications," Int. J. Radiation Onc. Biol. Phys. (1993) 25:259-268.

Budd, G.T. et al., "A Southwest oncology group phase II trial of recombinant tumor necrosis factor in metastatic breast cancer," Cancer (1991) 68:1694-1695.

Burbage, C. et al., "Ricin fusion toxin targeted to the human granulocyte-macrophase colony stimulating factor receptor is selectively toxic to acute myeloid leukemia cells," Leuk Res. (1997) 21(7):681-690.

Buscher et al., Oncogene (1988) 3(3):301-311.

Bussemakers et al., Cancer Res. (1992) 52:2916-2922.

Caldas et al., Nat. Genet. (1994) 8:27-32.

Cantley et al., "Oncogenes and signal transduction," Cell (1991) 64:281-302.

Cao et al., "Identification and characterization of the Egr-1 gene product, a DNA-binding zinc finger protein induced by differentiation and growth signals," Mol. Cell Biol. (1990) 10(5):1931-1939.

Caplen et al., Gene (2000) 252(1-2):95-105.

Carbonelli et al. "A plasmid vector for isolation of strong promoters in *E. coli*," FEMS Microbiol. Lett. (1999) 177(1):75-82.

Carswell et al., "An endotoxin-induced serum factor that causes necrosis of tumors," Proc. Natl. Acad. Sci USA (1975) 72:3666-3670.

Caruso, M., "Gene therapy against cancer and HIV infection using the gene encoding herpes simplex virus thymidine kinase," Mol. Med. Today (1996) 1:212-217.

Casey et al., Oncogene (1991) 6:1791-1797.

Cathala et al., "A method for isolation of intact, translationally active ribonucleic acid," DNA(1983) 2:329-335.

Cemazar et al., "Effects of electrogenetherapy with p53wt combined with cisplatin on survival of human tumor cell lines with different p53 status," DNA Cell Biol. (2003) 22(12):765-775.

Chan et al., "Selective inhibition of the growth of ras-transformed human bronchial epithelial cells by emodin, a protein-tyrosine kinase inhibitor," Biochemical and Biophysical Research Communications (1993) 193(3):1152-1158.

Chandler et al., "RNA splicing specificity determined by the coordinated action of RNA recognition motifs in SR proteins," Proc. Natl. Acad. Sci. USA (1997) 94(8):3596-3601.

Chang, S.M. et al., "Temozolomide in the treatment of recurrent malignant glioma," Cancer (2004) 100(3):605-611.

Chaudhary et al., Proc. Natl. Acad. Sci. USA(1987) 84:4538-4542.

Chaudhary et al., Proc. Natl. Acad. Sci. (1990) 87:9491-9494.

Chen et al., "Structural of malhamensilipin A, an inhibitor of protein tyrosine kinase, from the cultured chrysophyte poterioochromonas malhamensis," J. Natl. Prod. (1994) 57(4):524-527.

Chen and Okayama, "High-efficiency transformation of mammalian cells by plasmid DNA," Mol. Cell Biol. (1987) 7(8):2745-2752.

Cheng et al., Cancer Res. (1994) 54:5547-5551.

Cheung et al., "Conformation dependence of antipeptide antibodies: characterization of cell-CAM105 isoform-specific antipeptide antibodies using proteins expressed in insect cells with baculoviral vectors," Arch. Biochem. Biophys. (1993) 305(2):563-569.

Chiles, T. et al., J. Immunol.(1991) 146:1730-1735.

Chirgwin, J.M. et al., Biochemistry(1979) 18:5294-5299.

Choi, C.W. et al., "Effects of 5-fluorouracil and leucovorin in the treatment of pancreatic-biliary tract adenocarcinomas," Am. J. Clin. Oncol. (2000) 23(4):425-428.

Chou, J. and Roizman, B., Proc. Natl. Acad. Sci. USA (1992) 89:3266-3270.

Christoforidis et al., Eur. J. Surg. Oncol. (2002) 28:875-890.

Christou et al., Proc. Natl. Acad. Sci. USA (1987) 84(12):3962-3966.

Christy et al., "A gene activated in mouse 3T3 cells by serum growth factors encodes a protein with 'zinc finger' sequences," Proc. Natl. Acad. Sci USA(1988) 85(21):7857-7861.

Christy et al., "DNA binding site of the growth factor-inducible protein Zif268," Proc. Natl. Acad. Sci, USA(1989) 86:8737-8741.

Chung et al, "Tumor necrosis factor-alpha-based gene therapy enhances radiation cytotoxicity in human prostate cancer," Cancer Gene Therapy (1998) 5(6):344-349.

Cleveland, D.W. et al., "Number and evolutionary conservation of α- and β-tubulin and cytoplasmic β- and γ-actin genes using specific cloned cDNA probes," Cell(1980) 20:95-105.

Cocea, "Duplication of a region in the multiple cloning site of a plasmid vector to enhance cloning-mediated addition of restriction sites to a DNA fragment," BioTechniques (1997) 23(5):814-816.

Cotten et al., Proc. Natl. Acad. Sci. USA (1992) 89(13):6094-6098.

Cotter, et al., Cancer Res. (1992) 52:997-1005.

Couch, R.B. et al., "Immunizatoin with types 4 and 7 adenovirus by selective infection of the intestinal tract," Am. Rev. Resp. Dis. (1963) 88:394-403.

Coupar et al., "A general method for the construction of recombinant vaccinia virus expressing multiple foreign genes," Gene (1988) 68:1-10.

Crystal, R.G., "Transfer of genes to humans: early lessons and obstacles to success," Science (1995) 270:404-410.

Culver, K. et al., "Lymphocytes as cellular vehicles for gene therapy in mouse and man," Proc. Natl. Acad. Sci. USA (1991) 88:3155-3159.

Culver et al. Science (1992) 256(5063):1550-1552.

Culver, K.W. and Blaese, R.M. et al., "Gene therapy for cancer," Trends in Genetics (1994) 10:174-178:

Curiel, "Gene transfer mediated by adenovirus-polylysine DNA complexes," Viruses in Human Gene Therapy, J.-M.H. Vos (Ed.), Carolina Academic Press, Durham, NC, (1994) 179-212.

Curran, T. and Franza, B.R., "Fos and Jun: The AP-1 Connection," Cell (1988) 55:395-397.

Dalton, S. and Treisman, R., "Characterization of SAP-1, a protein recruited by serum response factor to the c-fos serum response element," Cell(1992) 68:597-612.

Datta et al., "Ionizing radiation activates transcription of the EGR1 gene via CArG elements," Proc. Natl. Acad. Sci. USA (1992) 89:10149-10153.

Datta et al., "Down-regulation of cell cycle control genes by ionizing radiation," Cell Growth & Differentiation (1992) 3:637-644.

Datta et al., "Involvement of reactive oxygen intermediates in the induction of c-jun gene transcription by ionizing radiation," Biochemistry (1992) 31(35):8300-8306.

Datta et al., "Reactive oxygen intermediates target CC(A/T)6GC sequences to mediate activation of the early growth response 1 transcription factor gene by ionizing radiation," Proc. Natl. Acad. Sci. USA (1993) 90:2419-2422.

Datta et al., "Overexpression of Bcl-XL by cytotoxic drug exposure confers resistance to ionizing radiation-induced internucleosomal DNA fragmentation," Cell Growth & Differentiation (1995) 6:363-370.

Datta et al., "Activation of a CrmA-insensitive, p35 sensitive pathway in ionizing radiation-induced apoptosis," J. Biol. Chem. (1997) 272:1965-1969.

Davis et al., "Cellular thiols and reactive oxygen species in drug-induced apoptosis," J. Pharmacol. Exp. Ther. (2001) 296:1-6.

De Villiers et al., Nature (1984) 312:242-246.

Delmastro, D.A. et al., "DNA damage inducible-gene expression following platinum treatment in human ovarian carcinoma cell lines," Cancer Chemother. Pharmacol. (1997) 39:245-253.

DeLuca et al., J. Virol. (1985) 56:558-570.

Demetri et al., "A phase I trial of recombinant human tumor necrosis factor and interferon-gamma: effects of combination cytokine administration in vivo," J. Clin. Oncol. (1989) 7:1545-1553.

Deonarain, M.P., "Ligand-targeted receptor-mediated vectors for gene delivery," Exp. Opin. Ther. Patents (1998) 8(1):53-69.

Deschamps et al., Science (1985) 230:1174-1177.

Devary, Y. et al., Mol. Cell. Biol.(1991) 11:2804-2811.

Devary et al., "The mammalian ultraviolet response is triggered by activation of Src tyrosine kinases," Cell (1992) 71:1081-1091.

Dewey, W.C., "In vitro systems: Standardization of endpoints," Int. J. Radiat. Oncol. Biol. Phys.(1979) 5:1165-1174.

Dewey et al., Int. J. Radiat. Oncol. Biol. Phys., (1995) 33:781-796.

D'Halluin et al., "Transgenic maize plants by tissue electroporation," Plant Cell (1992) 4(12):1495-1505.

Dignam, J.D. et al., Nucl. Acids. Res.(1983) 11:1475-1489.

Diller, Mol. Cell Biol.(1990) 10:5772-5781.

Donaldson et al., "Activation of p34cdc2 coincident with taxol-induced apoptosis," Cell Growth Differ. (1994) 5:1041-1050.

Doroshow, "Prevention of doxorubicin-induced killing of MCF-7 human breast cancer cells by oxygen radical scavengers and iron chelating agents," Biochem. Biophys. Res. Commun. (1986) 135(1):330-335.

Dressler and Kolesnick, J. Biol. Chem.(1990) 265(25):14917-14921.

Dressler et al., Science, (1992) 255:1715-1718.

Duan et al., "Sensitization of human malignant glioma cell lines to tumor necrosis factor-induced apoptosis by cisplatin," J. Neurooncol. (2001) 52:23-36.

Duan, L. et al., "Impairment of both apoptotic and cytoprotective signalings in glioma cells resistant of the combined use of cisplatin and tumor necrosis factor alpha," Clin. Cancer Res. (2004) 10(1 Pt 1):234-243.

Dubensky et al., Proc. Nat. Acad. Sci. USA, (1984) 81:7529-7533.

Eck, S.L. and Wilson, J.M., "Gene-based therapy," Goodman and Gilman's The Pharmacological Basis of Therapeutics, 9th Ed. McGraw-Hill, NY (1996) 77-101.

Economou, J.S. et al., "Genetic analysis of the human tumor necrosis factor α/cachectin promoter region in a macrophage cell line," J. Exp. Med.(1989) 170:321-326.

Edbrooke et al., Mol. Cell. Biol., (1989) 9(5):1908-1916.

Edelman and Crossin, Annu. Rev. Biochem. (1991) 60:155-190.

Edelman, Annu. Rev. Biochem. (1985) 54:135-169.

Edlund et al., Science, (1985) 230(4728):912-916.

Eggermont, A.M. et al., "Current uses of isolated limb perfusion in the clinic and a model system for new strategies," Lancet Oncol. (2003) 4:429-437.

Elbashir et al., Genes Dev. (2001) 15(2):188-200.

Elbashir et al., Nature (2001) 411:494-498.

Elroy-Stein et al., Proc. Nat'l. Acad. Sci. USA (1989) 86(16):6126-6130.

Elshami, A.A. et al., "Treatment of pleural mesothelioma in an immunocompetent rat model utilizing adenoviral transfer of the herpes simplex virus thymidine kinase gene," Human Gene Therapy (1996) 7(2):141-148.

Emoto et al., EMBO J. (1995) 14(24):6148-6156.

Endo, Y. and Tsurngi, K., J. Biol. Chem.(1987) 262(17):8128-8130.

Enoch and Nurse, "Mutation of fission yeast cell cycle control genes abolishes dependence of mitosis on DNA replication," Cell (1990) 60:665-673.

Ezzeddine, Z.D. et al., New Biol.(1991) 3(6):608-614.

Fauser, A.A., J. Cell Biochem.(1991) 45:353-358.

Fechheimer, M. et al., "Transfection of mammalian cells with plasmid DNA by scrape loading and sonication loading," Proc. Natl. Acad. Sci. USA (1987) 84(23):8463-8467.

Felgner, P.L. et al., Proc. Natl. Acad. Sci. USA (1987) 84:7413-7417.

Feng and Holland, Nature (1988) 334:165-167.

Ferkol et al., "Regulation of the phosphoenolpyruvate carboxykinase/human factor IX gene introduced into the livers of adult rats by receptor-mediated gene transfer," FASEB J. (1993) 7:1081-1091.

Field, J. et al., Mol. Cell Biol. (1988) 8(5):2159-2165.

Fiers, FEBS Letters (1991) 285(2):199-212.

Firak and Subramanian, Mol. Cell. Biol. (1986) 6(11):3667-3676.

Fire et al., Nature (1998) 391:806-811.

Fisch et al., Mol. Cell Biol. (1987) 7(10):3490-3502.

Foecking and Hofstetter, "Powerful and Versatile Enhancer-Promoter Unit for Mammalian Expression Vectors," Gene (1986) 45:101-105.

Folgueras, A. et al., "Matrix metalloproteinases in cancer: from new functions to improved inhibition strategies," Int. J. Dev. Biol. (2004) 48:411-424.

Forbes et al., Exp. Cell Res. (1992) 198:367-372.

Fornace et al., Cancer Research (1986) 46:1703-1706.

Fornace, A.J. et al.,"DNA damage-inducible transcripts in mammalian cells," Proc. Natl. Acad. Sci. USA (1988) 85:8800-8804.

Fornace, A.J. et al., "Coordinate induction of metallothioneins I and II in rodent cells by UV irradiation," Mol. Cell Biol. (1988) 8(11):4716-4720.

Fornace, A.J. et al., "Induction of β-polymerase mRNA by DNA-damaging agents in Chinese hamster ovary cells," Mol. Cell Biol. (1989) 9:851-853.
Forster and Symons, Cell (1987) 49:211-220.
Fraley, R.T. et al., "Entrapment of a bacterial plasmid in phospholipid vesicles: Potential for gene transfer," Proc. Natl. Acad. Sci. USA (1979) 76(7):3348-3352.
French et al., Circulation (1994) 90(5):2414-2424.
Friedman, H.S. et al., "Activity of temozolomide in the treatment of central nervous sytem tumor xenografts," Cancer Res. (1995) 55:2853-2857.
Friedman, H.S. et al., "Temozolomide and treatment of malignant glioma," Clin. Cancer Res. (2000) 6(7):2585-2597.
Friedmann, "Progress toward human gene therapy," Science (1989) 244:1275-1281.
Frixen et al., J. Cell Biol. (1991) 113(1):173-185.
Fujita et al., Cell (1987) 49:357-367.
Fuks et al., Cancer Res. (1994) 54:2582-2590.
Gashler, A.L. et al., "A novel repression module, an extensive activation domain, and a bipartite nuclear localization signal defined in immediate-early transcription factor Egr-1," Molecular and Cellular Biology (1993) 13(8):4556-4571.
Gashler, A. and Sukhatme, V.P., "Early Growth Response Protein 1 (Egr-1): Prototype of a Zinc-finger Family of Transcription Factors," Progress in Nucleic Acid Research and Molecular Biology vol. 50 (1995) Academic Press, Inc., 191-224.
Gately et al., "Human prostate carcinoma express enzymatic activity that converts human plasminogen to the angiogenesis inhibitor, angiostatin," Cancer Res. (1996) 56:4887-4890.
Gerlach et al., Nature(1987) 328:802-805.
Gescher, "Analogs of staurosporine: potential anticancer drugs?," Gen. Pharmacol. (1998) 31(5):721-728.
Gessler, M. et al., "The human MyoD1 (MYF3) gene maps on the short arm of chromosome 11 but is not associated with the WAGR locus or the region for the Beckwith-Wiedemann syndrom," Hum. Genet.(1990) 86(2):135-138.
Gessler, M. et al., "Homozygous deletion in Wilms tumours of a zinc-finger gene identified by chromosome jumping," Nature (1990) 343:774-778.
Ghanem, M.A. et al., "Expression and prognostic value of Wilms' tumor 1 and early growth response 1 proteins in nephroblastoma," Clinical Cancer Research (2000) 6(11):4265-4271.
Ghosh et al., "Cloning of the p50 DNA binding subunit of NF-Kappa B: homology to rel and dorsal," Cell (1990) 62:1019-1029.
Ghosh, et al., Targeting of Liposomes to Hepatocytes, "Liver Diseases" (1991) 87-103.
Ghosh-Choudhury et al., "Protein IX, a minor component of the human adenovirus capsid, is essential for the packaging of full-length genomes," EMBO J. (1987) 6(6):1733-1739.
Ghosh-Choudhury and Graham, Biochem. Biophys. Res. Comm. (1987) 147:964-973.
Giancotti and Ruoslahti, Cell (1990) 60:849-859.
Gillies et al., Cell (1983) 33:717-728.
Gillespie et al., "Inhibition of pancreatic cancer cell growth in vitro by the tyrphostin group of tyrosine kinase inhibitors," Br. J. Cancer (1993) 68:1122-1126.
Gilman, M.Z., "The c-fos serum response element responds to protein kinase C-dependent and -independent signals but not to cyclic AMP," Genes Dev. (1988) 2:394-402.
Ginsberg et al., Proc. Natl. Aca. Sci. USA (1991) 88:1651-1655.
Gius, D. et al., "Transcriptional activation and repression by Fos are independent functions: The C terminus represses immediate-early gene expression via CArG elements," Mol. Cell. Biol.(1990) 10(8):4243-4255.
Glorioso et al., Ann. Rev. Microbiol. (1995) 49:675-710.
Gloss et al., EMBO J. (1987) 6(12):3735-3743.
Gluzman, Y. et al., "Helper-free adenovirus type-5 vectors," Eukaryotic Viral Vectors, Gluzman, Y., Ed., Cold Spring Harbor Press, Cold Spring Harbor, New York (1982) 187-192.
Godbout et al., Mol. Cell. Biol. (1988) 8(3):1169-1178.
Goetze, S. et al., "TNFalpha regulates expression of chemoattractant-inducible transcription factors in vascular lesions through MAPK," European Heart Journal (2000) 21:P3482 Suppl. S.

Goldfeld et al., Proc. Natl. Acad. Sci. USA (1990) 87:9769-9773.
Golumbek, P.T. et al. Science (1991) 254(5032):713-716.
Gomez-Foix et al., "Adenovirus-mediated transfer of the muscle glycogen phosphorylase gene into hepatocytes confers altered regulation of glycogen," J. Biol. Chem. (1992) 267(35):25129-25134.
Gomez-Munoz et al., J. Biol. Chem. (1994) 269(12):8937-8943.
Gonen et al., Cancer Immunol. Immunother. (1992) 35:388-394.
Gonzalez, V.M. et al., "Is cisplatin-induced cell dealth always produced by apoptosis?" Molecular Pharm. (2001) 59(4):657-663.
Gonzalez-Zulueta, M. et al., "Methylation of the 5' CpG island of the p16/CDKN2 tumor suppressor gene in normal and transformed human tissues correlates with gene silencing," Cancer Research (1995) 55(20):4531-4535.
Goodbourn and Maniatis, "Overlapping positive and negative regulatory domains of the human β-Interferon Gene," Proc. Natl. Acad. Sci. USA (1988) 85:1447-1451.
Goodbourn, S. et al., "The human β-interferon gene enhancer is under negative control," Cell (1986) 45:601-610.
Goodman, L.E. et al., "Structure and expression of yeast DPR1, a gene essential for the processing and intracellular localization of ras proteins," Yeast (1988) 4:271-281.
Goodman, L.E. et al., "Mutants of Saccharomyces cerevisiae defective in the farnesylation of Ras proteins," Proc. Natl. Acad. Sci. USA (1990) 87:9665-9669.
Gopal, Mol. Cell Biol, (1985) 5(5):1188-1190.
Gorczyca et al., Cancer Res. (1993) 53:1945-1951.
Gorczyca, W. et al., "DNA strand breaks occurring during apoptosis: their early in situ detection by the terminal deoxynucleotidyl transferase and nick translation assays and prevention by serine protease inhibitors," Int'l J. Oncol. (1992) 1:639-648.
Gorecki, D.C., "Prospects and problems of gene therapy: an update," Exp. Opin. Emerging Drugs (2001) 6(2):187-198.
Gossen and Bujard, Proc. Natl. Acad. Sci. USA (1992) 89:5547-5551.
Gossen et al., Science (1995) 268:1766-1769.
Gottschalk et al., Inter. Immun. (1993) 6(1):121-130.
Gottschalk et al., Proc. Natl. Acad. Sci. USA (1994) 91:7350-7354.
Gottschalk, et al., "Resistance to anti-IgM-induced apoptosis in a WEHI-231 subline is due to insufficient production of ceramide," Eur. J. Immunol. (1995) 25:1032-1038.
Gottshalk, A. and Quintans, J., "Apoptosis in B lymphocytes: The WEHI-231 perspective," Immunol. Cell Biol. (1995) 73:8-16.
Gould et al., "Complementation of the mitotic activator, p80cdc25, by a human protein-tyrosine phosphatase," Science (1990) 250:1573-1576.
Graham, F.L. et al., "Characteristics of a human cell line transformed by DNA from human adenovirus type 5," J. Gen. Virol. (1977) 36:59-72.
Graham, F.L. "Covalently closed circles of human adenovirus DNA are infectious," EMBO J. (1984) 3(12):2917-2922.
Graham, R. and Gilman, M., Science (1991) 251:189-192.
Graham and Prevec, "Adenovirus-based expression vectors and recombinant vaccines,"Vaccines: New approaches to immunological problems, Butterworth-Heinemann, Boston, MA (1992) 20:363-390.
Graham and Prevec, "Manipulation of adenovirus vectors," Methods in Molecular Biology: Gene Transfer and Expression Protocols 7 E.J. Murray (ed.) Clifton, NJ, Humana Press (1991) 109-128.
Graham and Van Der Eb, Virology (1973) 52:456-467.
Grant et al., "Modulation of 1-[beta-D-arabinofuranosyl] cytosine-induced apoptosis in human myeloid leukemia cells by staurosporine and other pharmacological inhibitors of protein kinase C," Oncol. Res. (1994) 6(2):87-99.
Gray et al., Planta Medica (1980) 39:209.
Greene et al., Immunology Today (1989) 10:272-278.
Grishok et al., Science, (2000) 287:2494-2497.
Grosschedl and Baltimore, Cell (1985) 41:885-897.
Grunhaus, A. and Horwitz, M.S. "Adenoviruses as cloning vectors," Seminar in Virology (1992) 3:237-252.
Gubits, R.M. et al., "Expression of immediate early genes after treatment of human astrocytoma cells with radiation and taxol." Int. Jour. of Radiation Onc., Bio., Physics (1993) 27(3):637-642.

Gupta, M.P. et al., "EGR-1, a serum-inducible zinc finger protein, regulates transcription of the rat cardiac α-myosin heavy chain gene," J. Biol. Chem. (1991) 266:(20)12813-12816.

Gupta et al., "Thyroid-stimulating hormone activates phospholipase D in FRTL-5 thyroid cells via stimulation of protein kinase C," Endocrinology (1995) 136(9):3794-3799.

Gupta et al., "Combined gene therapy and ionizing radiation is a novel approach to treat human esophageal adenocarcinoma," Ann. Surg. Oncol (2002) 9(5):500-504.

Gustafson et al., "Hydrogen peroxide stimulates phospholipase A2-mediated archidonic acid release in cultured intestinal epithelial cells (INT 407)," Archidonic Acid Release (1991) 26:237-247.

Hadley, S.W. et al., Bioconjug. Chem. (1991) 2:171-179.

Haggerty and Monroe, Cell Immun. (1994) 154:166-180.

Haimovitz-Friedman et al., "Ionizing radiation acts on cellular membranes to generate ceramide and initiate apoptosis," J. Exp. Med. (1994) 180:525-535.

Haimovitz-Friedman et al., Cancer Res. (1994) 54:2591-2597.

Halazonetis et al., Cell (1988) 55(5):917-924.

Hall, E.J. Radiobiology for the Radiologist, Harper and Row, Lippincott, Philadelphia (1988) 17-38.

Hall, *Radiobiology for the Radiologist*, Harper and Row (1994) 17-38.

Hallahan et al., "Increased tumor necrosis factor α mRNA after cellular exposure to ionizing radiation," Proc. Natl. Acad. Sci. USA (1989) 86:10104-10107.

Hallahan et al. "The interaction between recombinant human tumor necrosis factor and radiation in 13 human tumor cell lines," Int. J. Rad. Onc. Biol. (1990) 19:69-74.

Hallahan et al., "Transcriptional regulation of the TNF gene by x-irradiation," Proc. Am. Assoc. Cancer Res. (1990) 31(0):75.

Hallahan et al., "Protein kinase C mediates x-ray inducibility of nuclear signal transducers EGR1 and JUN," Proc. Natl. Acad. Sci. USA (1991) 88(6):2156-2160.

Hallahan, D. et al., "Tumor necrosis factor gene expression is mediated by protein kinase C following activation by ionizing radiation," Cancer Research (1991) 51:4565-4569.

Hallahan et al., "Mechanisms of x-ray mediated protooncogene c-jun expression in radiation-induced human sarcoma cell lines," Int. J. Radiation Oncology Biol. Phys. (1991) 21(6):1677-1681.

Hallahan, D.E. et al., "Inhibition of protein kinases sensitizes human tumor cells to ionizing radiation," Radiat. Res. (1992) 129:345-350.

Hallahan et al., "Phase I dose escalation study of tumor necrosis factor and radiation," Intl. J. Rad. Oncol. Biol. Phys. (1993) 27(1):184 Abstract 94.

Hallahan et al., "Radiation signaling mediated by Jun activiation following dissociation from a cell type-specific repressor," J. Biol. Chem. (1993) 268(7):4903-4907.

Hallahan et al., "The role of cytokines in radiation oncology," Important Advances in Oncology (1993) DeVita, et al. eds., J.B. Lippincott Co., Philadelphia, PA (1993) 71-80.

Hallahan, D.E. et al., "Membrane-derived second messenger regulates x-ray-mediated tumor necrosis factor α gene induction," Proc. Natl Acad. Sci. USA, (1994) 91:4897-4901.

Hallahan et al., "Ketoconazole attenuates radiation-induction of tumor necrosis factor," Int. J. Radiation Oncology (1994) 29(4):777-780.

Hallahan et al., "C-jun and Egr-1 participate in DNA synthesis and cell survival in response to ionizing radiation exposure," J. Biol. Chem. (1995) 270:30303-30309.

Hallahan et al., "Phase I dose-escalation study of tumor necrosis factor-alpha and concomitant radiation therapy," Cancer J. Sci. Am. (1995) 1(3):204-209.

Hallahan et al., "Spatial and temporal control of gene therapy using ionizing radiation," Nat. Med. (1995) 1:786-791.

Hallahan, D. et al., "E-selectin induction by ionizing radiation is independent of cytokine induction," Bioch. Biophys. Research Commun. (1995) 217(3):784-795.

Hallahan, D.E. et al., "Radiation-mediated gene expression in the pathogenesis of the radiation response," Seminars in Rad. Oncol. (1996) 6(4):250-267.

Hallahan, D.E. et al., "Prolonged c-jun expression in irradiated ataxia telangiectasia fibroblasts," Int. J. Radiat. Oncol. Biol. Phys. (1996) 36:355-360.

Hallahan, D.E. et al., "Ionizing radiation mediates expression of cell adhesion molecules in distinct histologic patterns within the lung," Cancer Research (1997) 57:2096-2099.

Hallahan et al., Cancer Res. (1998) 58:5484-5488.

Hallahan, D.E. et al., "The role of gene therapy in radiation oncology," Cancer Treatment and Research (1998) 93:153-167.

Hammond, L.A. et al., "Phase I and pharmacokinetic study of temozolomide on a daily-for-5-days schedule in patients with advasssnced solid malignancies," J. Clin. Oncol. (1999) 17(8):2604-2613.

Hanna, N.N. et al., "Modification of theradiation response by the administration of exogenous genes," Semin. Rad. Oncol. (1996) 6(4):321-328.

Hanna, N.N. et al., "Virally directed cytosine deaminase/s-fluorocytosine gener therapy enhances radiation response," Cancer Res. (1997) 57:4205-4209.

Hanna et al., "A phase I study of tumor necrosis factor-α gene transfer with radiation therapy for advanced solid tumors," Proc. of ASCO, Abstract No. 344 (2002).

Hannun and Linardic, "Sphingolipid breakdown products: anti-proliferative and tumor-suppressor lipids," Biochem. Biophys. Acta. (1993) 1154:223-236.

Hansen et al., "Re-examination and further development of rapid dye method for measuring cell growth/cell kill," J. Immunol. Methods (1989) 119:203-210.

Harbour, J.W. and Dean, D.C., "Rb function in cell-cycle regulation and apoptosis," Nature Cell. Biol. (2000) 2:E65-E67.

Harland, R.H. and Weintraub, H., "Translation of mRNA injected into Xenopus Oocytes is specifically inhibited by antisense RNA," J. Cell Biol. (1985) 101:1094-1099.

Harlow and Lane, *Antibodies: A laboratory manual*, Cold Spring Harbor Laboratory (1988).

Harmon and Allan, Scanning Microsc. (1988) 2:561-568.

Hartley et al., "DNA sequence selectivity of guanine-N7 alkylation by nitrogen mustards is preserved in intact cells," Nucleic Acids Research (1992) 20(12):3175-3178.

Hartwell and Weinert, "Checkpoints: Controls that ensure the order of cell cycle events," Science (1989) 246:629-634.

Haslinger and Karin, Proc. Natl. Acad. Sci. USA (1985) 82(24):8572-8576.

Hattori, K. et al., "Structure and chromosomal localization of the functional intronless human JUN protooncogene," Proc. Natl. Acad. Sci. USA(1988) 85:9148-9152.

Hauber and Cullen, J. Virology (1988) 62(3):673-679.

Havell et al., J. Exp. Med. (1988) 167:1067-1085.

He, B. et al., "RAM2, an essential gene of yeast, and RAMI encode the two polypeptide components of the farnesyltransferase that prenylates a-factor and Ras proteins," Proc. Natl. Acad. Sci. USA (1991) 88:11373-11377.

He et al., Plant Cell Reports (1994) 14:192-196.

Helfrich et al., "C225 anti-epidermal growth factor receptor (EGFR) monoclonal antibody sensitizes human non-small cell lung cancer to both radiation and chemotherpay cytotoxicity in-vitro and in-vivo," Int. J. Radiat. Oncol. Bio. 51(3Suppl), American Soc.

Hempel et al., "Tyrosine phosphorylation of phospholipase C-12 upon cross-linking of membrane Ig on murine B lymphocytes," J. Immuno. (1992) 148(10):3021-3027.

Hen, R. et al., "A mutated polyoma virus enhancer which is active in undifferentiated embryonal carcinoma cells is not repressed by adenovirus-2 E1A products," Nature, (1986) 321:249-251.

Hensel, G. et al., "PMA-responsive 5' flanking sequences of the human TNF gene," Lymphokine Res. (1989) 8(3):347-351.

Herbert et al., "Chelerythrine is a potent and specific inhibitor of protein kinase C," Biochem. Biophys. Res. Commun., (1990) 172:993-999.

Herman, J.G. et al., "Inactivation of the CDKN2/p16/MTS1 gene is frequently associated with aberrant DNA methylation in all common human cancers," Cancer Research (1995) 55(20):4525-4530.

Herr, W. and Clarke, J., The SV40 enhancer is composed of multiple functional elements that can compensate for one another, Cell (1986) 45:461-470.
Herrlich, P., "The problem of latency in human disease. Molecular action of tumor promoters and carcinogens," Accomplishments in Cancer Research, Lippincott, Philadelphia (1987) 213-230.
Herrlich et al., "DNA damage-induced gene expression: signal transduction and relation to growth factor signaling," Physiol. Biochem. Pharmacol. (1992) 119:187-223.
Hesdorffer, C. et al., "Efficient gene transfer in live mice using a unique retroviral packaging line," DNA Cell Biol. (1990) 9(10):717-723.
Herz and Gerard, "Adenovirus-mediated transfer of low density lipoprotein receptor gene acutely accelerates cholesterol clearance in normal mice," Proc. Natl. Acad. Sci. USA (1993) 90:2812-2816.
Hill, S. et al. "Low-dose tumour necrosis factor α and melphalan in hyperthermic isolated limb perfusion," Br. J. Surg. (1993) 80:995-997.
Hirochika et al., J. Virol. (1987) 61(8):2599-2606.
Hirose, Y. et al., "p53 effects both the duration of G2/M arrest and the fate of temozolomide-treated human glioblastoma cells," Cancer Res. (2001) 61:1957-1963.
Hirsch et al., Mol. Cell. Biol. (1990) 10(5):1959-1968.
Hodgson, "Advances in vector systems for gene therapy," Exp. Opin. Ther. Patents (1995) 5:459-468.
Holbrook et al., Virology (1987) 157:211-219.
Holland et al., Virology (1980) 101:10-24.
Hollander, C.M. and Fornace, A.J., Jr., "Induction of fos by DNA-damaging agents," Cancer Res. (1989) 49:1687-1692.
Hollstein et al., Science (1991) 253(5015):49-53.
Homma, Y. et al., "Translocation of protein kinase C in human leukemia cells susceptible or resistant to differentiation induced by phorbol 12-myristate 13-acetate," Proc. Natl. Acad. Sci USA (1986) 83(19):7316-7319.
Honess and Roizman, J. Virol (1975) 16(5):1308-1326.
Honess and Roizman, J. Virol. (1974) 14(1):8-19.
Horlick and Benfield, Mol. Cell. Biol (1989) 9(6):2396-2413.
Horton et al., Nucleic Acids Res. (1995) 23:3810-3815.
Horwich et al., "Synthesis of hepadenovirus particles that contain replication-defective duck hepatitis B virus genomes in cultured HuH7 cells," J. Virol. (1990) 64(2):642-650.
Hou et al., "Rapid Optimization of Electroporation Conditions for Soybean and Tomato Suspension Cultured Cells," Supplements Plant Physiology (1996) 111:166.
Houben, "Free radicals produced by ionizing radiation in bone and its constituents," Int. J. Radiat. Biol. Relat. Stud. Phys. Chem. Med. (1971) 20:373-389.
Hsu et al., "Inhibition kinetics and selectivity of the tyrosine kinase inhibitor erbstatin and a pyridone-based analogue," Biochemical Pharmacology (1992) 43(11):2471-2477.
Hu and Fan, "Protein kinase C inhibitor calphostin C presents cytokine-induced angiogenesis in the rat," Inflammation (1995) 19(1):39-54.
Huang et al., Cell (1981) 27:245-255.
Hug, H. et al., "Organization of the murine Mx gene and characterization of its interferon- and virus-inducible promoter," Mol. Cell Biol. (1988) 8(8):3065-3079.
Hughes, R.M., "Strategies for Cancer Gene Therapy," J. Surg. Oncol. (2004) 85:28-35.
Hunt et al., Proc. Natl. Acad. Sci. USA (1986) 83(11):3786-3790.
Hussussian et al., Nature Genetics (1994) 8:15-21.
Hwang et al., Mol. Cell. Biol. (1990) 10(2):585-592.
Hwu et al., "Functional and molecular characterization of tumor-infiltrating lymphocytes transduced with tumor necrosis factor-a cDNA for the gene therapy of cancer in humans," J. Immunol. (1993) 150(9):4104-4115.
Imagawa, M. et al., "Transcription factor AP-2 mediates induction by two different signal-transduction pathways: protein kinase C and cAMP," Cell (1987) 51:251-260.
Imbra, R.J. and Karin, M., "Phorbol ester induces the transcritpional stimulatory activity of the SV40 enhancer," Nature (1986) 323:555-558.
Imler et al., Mol. Cell. Biol. (1987) 7(7):2558-2567.
Indap and Rao, Natl. Med. J. India (1995) 8:65-67.
Inouye et al., "Up-promoter mutations in the Ipp gene of *Escherichia coli*," Nucl. Acids Res. (1985) 13:3101-3109.
Irie and Morton, "Regression of cutaneous metastatic melanoma by intralesional injection with human monoclonal antibody to ganglioside GD2," Proc. Nat'l. Acad. Sci. USA (1986) 83(22):8694-8698.
Jacobson et al., "Role of Ced-3/ICE-family proteases in staurosporine-induced programmed cell death," J. Cell. Biol. (1996) 133:1041-1051.
Jacobson et al., "Programmed cell death and Bcl-2 protection in the absence of a nucleus," Embo. J. (1994) 13:1899-1910.
Jakobovits et al., Mol. Cell. Biol. (1988) 8(6):2555-2561.
Jameel and Siddiqui, Mol. Cell. Biol., (1986) 6(2):710-715.
Jarvis et al., Clinical Cancer Research (1996) 2:1-6.
Jarvis et al., "Induction of apoptotic DNA fragmentation and cell death in HL-60 human promyelocytic leukemia cells by pharmacological inhibitors of protein kinase C," Cancer Res. (1994) 54:1707-1714.
Jarvis et al., Proc. Natl. Acad. Sci. USA (1994) 91:73-77.
Jarvis, W.D. et al., "Induction of apoptosis and potentiation of ceramide-mediated cytotoxicity by sphingoid bases in human myeloid leukemia cells," J. Biol. Chem. (1996) 271(14):8275-8284.
Jayasuriya et al., "Emodin, a protein tyrosine kinase inhibitor from *Polygonum cuspidatum*," J. Nat. Proc. (1992) 55(5):696-698.
Jaynes et al., Mol. Cell. Biol. (1988) 8(1):62-70.
Ji, et al., Biochem. Biophys. Res. Commun. (1995) 212:640-647.
Johnson, P. et al., Mol. Cell Biol.(1991) 11(1):1-11.
Johnson and Stevenson, "Cisplatin and its analogues," Cancer. Principles and Practice of Oncology, (eds. Devita, Hellman and Rosenberg) (2001) 376-388.
Johnson et al., Mol. Cell. Biol (1989) 9(8):3393-3399.
Johnsson et al., "The c-sis gene encodes a precursor of the B chain of platelet-derived growth factor," EMBO J. (1984) 3:921-928.
Joki, T. et al., "Activation of the radiosensitive EGR-1 promoter induces expression of the herpes simplex virus thymidine kinase gene and sensitivity of human glioma cells to ganciclovir," Human Gene Ther. (1995) 6:1507-1513.
Jones and Murray, J. Biol. Chem (1995) 270:5007-5013.
Jones, N. and Shenk, T., "Isolation of deletion and substitution mutants of adenovirus type 5," Cell (1978) 13:181-188.
Joyce, Nature (1989) 338:217-224.
Jung, M. et al., "Mutations in the p53 gene in radiation-sensitive and-resistant human squamous carcinoma cells," Cancer Res. (1992) 52:6390-6393.
Kadesch and Berg, Mol. Cell. Biol (1986) 6(7):2593-2601.
Kaeppler et al., Plant Cell Reports (1990) 9:415-418.
Kageyama et al., J. Biol. Chem (1987) 262(5):2345-2351.
Kalderon, D. et al., Cell (1984) 39:499-509.
Kamb, A. et al., "Analysis of the p16 gene (CDKN2) as a candidate for the chromosome 9p melanoma susceptibility locus," Nature Genetics (1994) 8:22-26.
Kamb et al., Science (1994) 264:436-440.
Kaneda et al., Science (1989) 243:375-378.
Karin et al., Mol. Cell. Biol (1987) 7(2):606-613.
Karlsson et al., EMBO J. (1986) 5(9):2377-2385.
Kartalou and Essigmann, "Mechanisms of resistance to cisplatin," Mutat. Res. (2001) 478:23-43.
Kastan et al., "Participation of p53 protein in the cellular response to DNA damage," Cancer Research (1991) 51:6304-6311.
Katinka et al., Cell (1980) 20:393-399.
Katinka et al., Nature (1981) 290:720-722.
Kato et al., J. Biol. Chem. (1991) 266(6):3361-3364.
Kawamoto et al., Mol. Cell. Biol. (1988) 8(1):267-272.
Kearns et al., "Recombinant Adeno-Associated Virus (AAV_CFTR) Vectors do not Integrate in a Site-Specific Fashion in an Immortalized Epithelial Cell Line," Gene Ther. (1996) 3:748-755.
Kelleher and Vos, "Long-term episomal gene delivery in human lymphoid cells using human and avian adenoviral-assisted transfection," Biotechniques (1994) 17(6):1110-1117.
Ketting et al., Cell (1999) 99:133-141.

Khachigian, L.M. and Collins, T., "Early growth response factor 1: a pleiotropic mediator of inducible gene expression," J. Mol. Med. (1998) 76:613-616.

Kharbanda, S. et al., J. Clin. Invest.(1991) 88:571-577.

Kharbanda, S. et al., "Ionizing radiation induces rapid tyrosine phosphorylation of p34cdc2," Cancer Res. (1994) 54:1412-1414.

Kharbanda, S. et al., "Ionizing radiation stimulates a Grb2-mediated association of the stress-activated protein kinase with phosphatidylinositol 3-kinase," J. Biol. Chem. (1995) 270:18871-18874.

Kharbanda, S.et al., "Activation of the c-Abl tyrosine kinase in the stress response to DNA-damaging agents," Nature (1995) 376(6543):785-788.

Kharbanda, S. et al., "The stress response to ionizing radiation involves c-Abl-dependent phosphorylation of SHPTP1," Proc. Natl. Acad. Sci. USA (1996) 93:6898-6901.

Kharbanda, S. et al., "Nuclear signaling induced by ionizing radiation involves colocalization of the activated p56/p53lyn tyrosine kinase with p34cdc2," Cancer Res. (1996) 56:3617-3621.

Kiledjian et al., Mol. Cell. Biol. (1988) 8(1):145-152.

Kim and Cech, Proc. Natl. Acad. Sci. USA (1987) 84:8788-8792.

Klamut et al. Mol. Cell Biol (1990) 10(1):193-205.

Klein et al. Nature (1987) 327:70-73.

Knox, K.A. et al., "A study of protein kinase C isozyme distribution in relation to Bcl-2 expression during apoptosis of epithelial cells in vivo," Exp. Cell Res. (1993) 207:68-73.

Kobayashi, et al., "Calphostins (UCN-1028), novel and specific inhibitors of protein kinase C. I. Fermentation, isolation, physico-chemical properties and biological activities," J. Antibiot. (1989) 42:1470-1474.

Kobayashi, et al., Biochem. Biophys. Res. Commun. (1989) 159:548-553.

Koch et al., Mol. Cell. Biol. (1989) 9:303-311.

Kohl, N.E. et al., "Structural homology among mammalian and Saccharomyces cerevisiae isoprenyl-protein transferases," J. Biol. Chem. (1991) 266(28):18884-18888.

Kolch et al., Nature (1991) 349:426-428.

Kolesnick et al., Biochem. Cell. Bio. (1994) 72:471-474.

Kolesnick, J. Biol. Chem (1989) 264:7617-7623.

Kolesnick, Planta Medica (1994) 21:287-297.

Kondratyev, et al., Cancer Res. (1996) 56:1498-1502.

Konishi et al., "Transcriptionally targeted in vivo gene therapy for carcinoembrionic antigen-producing adenocarcinoma," J. Med. Sci. (1999) 48(3):79-89.

Korhonen et al., Blood (1995) 86(5):1828-1835.

Kotin and Berns, Virol. (1989) 170:460-467.

Kotin, R.M. et al., "Mapping and direct visualization of a region-specific viral DNA integration site on chromosome 19q13-qter," Genomics (1991) 10:831-834.

Kotin et al., Proc. Natl. Acad. Sci. USA (1990) 87:2211-2215.

Kraus et al., "Alternative promoter usage and tissue specific expression of the mouse somatostatin receptor 2 gene," FEBS Lett (1998) 428(3):165-170.

Kreitman, R.J. and Pastan, I., "Targeting Pseudomonas exotoxin to hematologic malignancies," Cancer Biol. (1995) 6:297-306.

Kriegler and Botchan, Eukaryotic Viral Vectors, Y. Gluzman, ed., Cold Spring Harbor: Cold Spring Harbor Laboratory, NY (1982) ).

Kriegler and Botchan, Mol. Cell. Biol. (1983) 3(3):325-339.

Kriegler et al., Cancer Cells 2/Oncogenes and Viral Genes, Van de Woude et al., eds, Cold Spring Harbor, Cold Spring Harbor Laboratory (1984).

Kriegler et al., Cell (1984) 38:483-491.

Kriegler et al., Cell (1988) 53:45-53.

Kriegler et al., Gene Expression, D. Hamer and M. Rosenberg, eds., New York: Alan R. Liss (1983).

Kubota, M. "Generation of DNA damage by anti-neoplastic agents," Anti-Cancer Drugs (1991) 2(6):531-541.

Kucuk et al., "Phase II trial of cisplatin, etoposide, and 5-fluorouracil in advanced non-small-cell lung cancer," Am. J. Clin. Oncol. (2000) 23:371-375.

Kuhl et al., Cell (1987) 50:1057-1069.

Kunz et al., Nucl. Acids Res. (1989) 17:1121-1138.

Kuppen et al., Br. J. Cancer (1997) 75(10):1497-1500.

Kurihara et al., "Selectivity of a replication-component adenovirus for human breast carcinoma cells expressing the MUC1 antigen," J. Clin. Invest. (2000) 106(6):763-771.

Lacroix, M. et al., "A multivariate analysis of 416 patients with glioblastoma multiforme: prognosis, extent of resection, and survival," J. Neurosurg. (2001) 95(2):190-198.

Lal, S. et al., "An implantable guide-screw system for brain tumor studies in small animals," J. Neurosurg. (2000) 92(2):326-333.

Lambert, M. et al., "X-ray-induced changes in gene expression in normal and oncogene-transformed rat cell lines," J. of the Natl. Cancer Instit. (1988) 80(18):1492-1497.

Lamph et al., Proc. Natl. Acad. Sci USA (1990) 87:4320-4324.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," J. Biol. (1999) 274(12):8282-8290.

Larrick, J.W. and Wright, S.C., "Cytotoxic mechanisms of tumor necrosis factor-a," FASEB J. (1990) 4:3215-3223.

Larsen et al., Proc. Nat'l. Acad. Sci. USA (1986) 83:8283-8287.

Laspia et al., Cell (1989) 59:283-292.

Latimer et al., Mol. Cell. Biol. (1990) 10(2):760-769.

Lau, L.F. et al., Proc. Natl. Acad. Sci. USA(1987) 84(5):1182-1186.

Laughlin et al., J. Virol. (1986) 60(2):515-524.

Lazzeri, P.A., "Stable transformation of barley via direct DNA update. Electroporation- and PEG-mediated protoplast transformation," Methods Mol. Biol. (1995) 49:95-106.

Le Gal La Salle et al., "An adenovirus vector for gene transfer into neurons and glia in the brain," Science (1993) 259:988-990.

Lebkowski, J.S. et al., "Adeno-associated virus: a vector system for efficient introduction and integration of DNA into a variety of mammalian cell types," Mol. Cell Biol. (1988) 8(10):3988-3996.

Ledley et al., Proc. Natl. Acad. Sci. USA (1987) 84(15):5335-5339.

Lee et al., "Tissue-specific promoter usage in the D1A dopamine receptor gene in brain and kidney," DNA Cell Biol (1997) 16(11):1267-1275.

Lee et al., Mol. Endocrinol. (1988) 2:404-411.

Lee et al., Nature (1981) 294:228-232.

LeJeune et al., Circ. Shock (1994) 43:191-197.

Lemaire et al., Proc. Natl. Acad. Sci. USA (1988) 85(13):4691-4695.

Levenson, V.V. et al., "Internal ribosomal entry site-containing retroviral vectors with green fluorescent protein and drug resistance markers," Human Gene Therapy (1998) 9:1233-1236.

Levine, S.R. and Brott, T.G., Prog. Cardiovasc. Dis.(1992) 34:235-262.

Levinson, B. et al., "Activation of SV40 genome by 72-base pair tandem repeats of Moloney sarcoma virus," Nature (1982) 295(5850):568-572.

Levrero et al., "Defective and nondefective adenovirus vectors for expressing foreign genes in vitro and in vivo," Gene (1991) 101:195-202.

Lewin, B., Cell (1991) 64:303-312.

Li et al., "The redox active components H2O2 and N-acetyl-L-cysteine regulate expression of c-jun and c-fos in lens systems," Exp. Eye Res. (1994) 59:179-190.

Liang, B.C. et al., "Malignant astrocytomas: focal tumor recurrence after focal external beam radiation therapy," J. Neurosurg. (1991) 75(4):559-563.

Lidor et al., Am. J. Obstet. Gynecol (1997) 177(3):579-585.

Lienard et al., "Isolated Perfusion of the Limb with High-Dose Tumour Necrosis Factor-Alpha (TNF-α), Interferon-Gamma (IFN-γ) and Melphalan for Melanoma Stage III. Results of a Multi-centre Pilot Study," Melanoma Res. (1994) 4(1):21-26.

Lim et al., Oncogene(1987) 1:263-270.

Lin and Avery, Nature (1999) 402:128-129.

Lin and Guidotti, J. Biol. Chem. (1989) 264:14408-14414.

Lin et al., Mol. Cell. Biol. (1990) 10(2):850-853.

Little, J.W. and Mount, D.W., "The SOS regulatory system of escherichia coli," Cell (1982) 29:11-22.

Long et al., J. Clin. Invest. (1988) 82:1779-1786.

Lory, J. Bacteriology(1988) 170(2):714-719.

Lowe et al., Cell (1993) 74:957-967.

Lowe et al., Nature (1993) 362:847-849.

Lowe et al., Science (1994) 266:807-810.
Lozano et al., J. Biol. Chem., (1994) 269:19200-19202.
Luna et al., "Photodynamic therapy mediated induction of early response genes," Cancer Research (1994) 54(5):1374-1380.
Luria et al., EMBO J. (1987) 6:3307-3312.
Lusky and Botchan, Proc. Nat'l. Acad. Sci. USA (1986) 83:3609-3613.
Lusky et al., Mol. Cell. Biol. (1983) 3(6):1108-1122.
Macejak, D.G. and Sarnow, P., "Internal initiation of translation mediated by the 5' leader of a cellular mRNA," Nature (1991) 353:90-94.
Maity, et al., Radiother. Oncol. (1994) 31:1-13.
Majors and Varmus, Proc. Nat'l Acad. Sci. USA (1983) 80:5866-5870.
Mann et al., Cell (1983) 33:153-159.
Manome, Y. et al., "Coinduction of c-jun gene expression and internucleosomal DNA-fragmentation by ionizing radiation," Biochemistry (1993) 32:10607-10613.
Manome, Y. et al., "Early repsonse gene induction following DNA damage in astrocytoma cell lines," Biochemical Pharmacology (1993) 45(8):1677-1684.
Manome, Y. et al., "Transgene expression in malignant glioma using a replication detective adenoviral vector containing the Egr-1 promoter: activation by ionizing radiation or uptake of radioactive iododeoxyuridine," Human Gene Ther. (1998) 9:1409-1417.
Manusama, E.R. et al., "Synergistic antitumour effect of recombinant human tumour necrosis factor alpha with melphalan in isolated limb perfusion in the rat," Br. J. Surg. (1996) 83(4):551-555.
Markowitz et al., J. Virol (1988) 62(4):1120-1124.
Marmorstein et al., Nature(1992) 356:408-414.
Marshall, "Gene therapy's growing pains," Science (1995) 269:1050-1055.
Martin and Green, Curr. Opin. Oncol (1994) 6:616-621.
Martin et al., EMBO J. (1995) 14:5191-5200.
Massuda et al., Proc. Nat'l Acad. Sci USA (1997) 94(26):14701-14706.
Matsuura et al., Brit. J. Cancer (1992) 66:1122-1130.
Mattern et al., "Human tumor xenografts as model for drug testing," Cancer and Metastatis Reviews (1988) 7:263-284.
Matthews et al., "Tumor cell killing by TNF inhibited by anaerobic conditions, free radical scavengers and inhibitors of arachadonate metabolism," Immunology(1987) 62:153-155.
Matthews et al., Tumor Necrosis Factor/Cachectin and Related Cytokinesis, Eds. Bonavina, et al. (Karger, New York) (1988) 20-25.
Mauceri, H. et al., "Tumor size does not limit radiation-inducible gene therapy in a human xenograft model," Rad. Oncol. Invest. (1995) 3:238-242.
Mauceri et al., "Tumor necrosis factor α (TNF-α) gene therapy targeted by ionizing radiation selectively damages tumor vasculature," Cancer Research (1996) 56:4311-4314.
Mauceri et al., "Increased injection number enhances adenoviral genetic radiotherapy," Radiat. Oncol. Investig. (1997) 5:220-226.
Mauceri et al., "Combined effects of angiostatin and ionizing radiation in antitumour therapy," Nature (1998) 394:287-291.
Mauceri et al., "Tumor production of angiostatin is enhanced after exposure to TNF-α," Int. J. Cancer (2002) 97:410-415.
May et al., "Interleukin-3 and bryostatin-1 mediate hyperphosphorylation of BCL2 alpha in association with suppression of apoptosis," J. Bio. Chem. (1994) 269:26865-26870.
McConkey et al., "Inhibition of DNA fragmentation in thymocytes and isolated thymocyte nuclei by agents that stimulate protein kinase C," J. Biol. Chem. (1989) 264:13399-13402.
McCubrey, J.A. et al., "Serine/threonine phosphorylation in cytokine signal transduction," Leukemia (2000) 14(1):9-21.
McGrory et al., Virology(1988) 163:614-617.
McKenna, et al., Radiat. Res. (1991) 125:283-287.
McLaughlin et al., J. Virol. (1988) 62(6):1963-1973.
McMahon, A.P. et al., "Developmental expression of the putative transcription factor Egr-1 suggests that Egr-1 and c-fos are coregulated in some tissues," Development (1990) 108:281-287.
McNeall et al., Hyperinducible Gene Expression from a Metallothionein Promoter Containing Additional Metal-Responsive Elements, Gene (1989) 76:81-88.

Merck Index, THE, Eleventh Edition.
Merlo et al., "5' CpG island methylation is associated with transcriptional silencing of the tumour suppressor p16/CDKN2/MTS1 in human cancers," Nat. Med. (1995) 1(7):686-692.
Meyn et al., Anticancer Drugs (1995) 6:443-450.
Meyn et al., Int. J. Radiat. Oncol. Biol. Phys (1994) 30:619-624.
Meyn et al., Radiat. Res (1993) 136:327-334.
Michel and Westhof, J. Mol. Biol. (1990) 216:585-610.
Miksicek et al., Cell (1986) 46:283-290.
Milbrandt, Science (1987) 238(4828):797-799.
Miller et al., Am. J. Clin. Oncol.(1992) 15(3):216-221.
Miller , Curr. Top. Microbiol. Immunol. (1992) 158:1-24.
Miller et al., "Targeted vectors for gene therapy," FASEBJ (1995) 9:190-199.
Miskin, R. and Ben-Ishai, R., "Induction of plasminogen activator by UV light in normal and xeroderma pigmentosum fibroblasts," Proc. Natl. Acad. Sci. USA (1981) 78:6236-6240.
Mitchell et al., Science (1989) 245(4916):371-378.
Mitchell et al., "Active-specific immunotherapy for melanoma," J. Clin. Oncol. (1990) 8(5):856-869.
Mitchell et al., Active Specific Immunotherapy of Melanoma with Allogeneic Cell Lysates, Ann. NY Acad. Sci. (1993) 690:153-166.
Mitchell et al., Proc. Natl. Acad. Sci. USA (1993) 90:11693-11697.
Mittelman et al., "A Phase I Pharmacokinetic Study of Recombinant Human Tumor Necrosis Factor Administered by a 5-Day Continuous Infusion," Invest. New Drugs (1992) 10:183-190.
Mizukami et al., Virology (1996) 217:124-130.
Moffat, A.S., "X-rays trigger production of TNF in laboratory experiments" Newspaper article.
Montgomery et al., Proc. Natl. Acad. Sci USA (1998) 95:15502-15507.
Moolten et al., "Curability of tumors bearing herpes thymidine kinase genes transferred by retroviral vectors," J. Natl. Cancer Inst. (1990) 82:297-300.
Mordacq et al., "Co-Localization of Elements Required for Phorbol Ester Stimulation and Glucocorticoid Repression of Proliferin Gene Expression," Genes and Dev. (1989) 3:760-769.
Moreau et al., Nucl. Acids Res. (1981) 9(22):6047-6068.
Mori et al., Cancer Res. (1994) 54:3396-3397.
Morton and Ravindranath, "Current concepts concerning melanoma vaccines," Tumor Immunology, Dalgleish (ed.), London: Cambridge University Press (1996) 241-268.
Morton et al., "Prolongation of survival in metastatic melanoma after active specific immunotherapy with a new polyvalent melanoma vaccine," Ann. Surg. (1992) 216(4):463-482.
Moulder, J.E. and Rockwell, S., "Hypoxic fractions of solid tumors: experimental techniques, methods of analysis, and a survey of existing data," Int. J. Radiat. Oncol. Biol. Phys. (1984) 10:695-712.
Muesing et al., Cell (1987) 48:691-701.
Mukherjee, A.B. et al. Proc. Natl. Acad. Sci. USA (1978) 75(3):1361-1365.
Mulligan et al., Proc. Nat'l Acad. Sci. USA (1981) 78(4):2072-2076.
Mundschau, L.J. and Faller, D.V., "Platelet-derived growth factor signal transduction through the interferon-inducible kinase PKR. Immediate early gene induction," Journal of Biological Chemistry (1995) 270(7):3100-3106.
Mundt et al., "TNFerade, an adenovector encoding the human tumor necrosis factor alpha gene, in soft tissue sarcoma in the extremity, safety and early efficacy data," EORTC-NCI-AACR Symposium on Molecular Targets and Cancer Therapeutics, Abstract 741, Frankfurt, Germany, Nov. 19-22, 2002.
Mustelin and Altman, "Dephosphorylation and activation of the T cell tyrosine kinase pp56lck by the leukocyte common antigen (CD45)," Oncogene (1990) 5:809-813.
Muzyczka, N., "Use of Adeno-Associated Virus as a General Transduction Vector for Mammalian Cells," Current Topics in Microbiology and Immunology (Compans et al. eds.) (1992) 158:97-129.
Nabel et al., "Recombinant gene expression in vivo within endothelial cells of the arterial wall," Science (1989) 244:1342-1344.
Nagasawa et al., "Absence of a radiation-induced first-cycle G1-S arrest in p53+ human tumor cells synchronized by mitotic selection," Cancer Res. (1998) 58:2036-2041.

Nagasawa et al., Int. J. Radiat. Biol. (1994) 66:373-379.
Nagata and Golstein, Science (1995) 267:1449-1456.
Nakabeppu et al., Cell(1988) 55(5):907-915.
Nakamoto et al., "A new method of antitumor therapy with a high dose of TNF perfusion for unresectable liver tumors," Anticancer Res. (2000) 20:4087-4096.
Naldini et al., "In vivo gene delivery and stable transduction of nondividing cells by a lentiviral vector," Science (1996) 272(5259):263-267.
Nawroth and Stern, J. Exp. Med. (1986) 163:740-745.
Neale et al., Immunology(1988) 64:81-85.
Nedwin, G.E. et al., "Human lymphotoxin and tumor necrosis factor genes: structure, homology and chromosomal localization," Nucl. Acids Research, (1985) 13(17):6361-6373.
Neta and Oppenheim, "Radioprotection with cytokines-learning from nature to cope with radiation damage," Cancer Cells (1991) 3(10):391-396.
Neta et al., "Interdependence of the Radioprotective Effects of Human Recombinant Interleukin 1α, Tumor Necrosis Factor α, Granulocyte Colony-Stimulating Factor, and Murine Recombinant Granulocyte-Macrophage Colony-Stimulating Factor," J. Immunology (1988) 140:1:108-111.
Neta et al., "Comparison of in Vivo Effects of Human Recombinant IL 1 and Human Recombinant IL 6 in Mice," Lymphokine Res. (1988) 7:4:403-412.
Neta et al., "Role of cytokines (interleukin 1, tumor necrosis factors, and transforming growth factor beta) in natural and lipopolysaccharide-enhanced radioresistance," J. Exp. Med.(1991) 173:1177-1182.
Neta et al., "Role of interleukin 6 (IL-6) in protection from lethal irradiation and in endocrine responses to IL-1 and tumor necrosis factor," J. Exp. Med.(1992) 175:689-694.
Ng et al., Nuc. Acids Res. (1989) 17(2):601-615.
Nicolas and Rubenstein, Vectors: A survey of molecular cloning vectors and their uses, Rodriguez and Denhardt (eds.), Stoneham: Butterworth (1988) 493-513.
Nicolau, C. and Sene, C., "Liposome-mediated DNA transfer in eukaryotic cells. Dependence of the transfer efficiency upon the type of liposomes used and the host cell cycle stage," Biochimica et Biophysica Acta (1982) 721:185-190.
Nicolau et al., Proc. Natl. Acad. Sci. USA(1983) 80:1068-1072.
Nicolau et al., "Liposomes as Carriers for in Vivo Gene Transfer and Expression," Methods in Enzymology (1987) 149: 157-177.
Nixon et al., "The design of biological properties of selective inhibitors of protein kinase C," Second Messenger Systems (1992) 419-425.
Nobori et al., Nature (1994) 368:753-756.
Nomoto et al., "Cloning and characterization of the alternative promoter regions of the human LIMK2 gene responsible for alternative transcripts with tissue-specific expression," Gene (1999) 236(2):259-271.
Nose et al., "Transcriptional activation of early-response genes by hydrogen peroxide in a mouse osteoblastic cell line," Eur. J. Biochem. (1991) 201:99-106.
Nurse, "Universal control mechanism regulating onset of M-phase," Nature (1990) 344:503-508.
Obeid et al., Science (1993) 259:1769-1771.
Obrador et al., Curr. Pharm. Biotechnol. (2001) 2:119-130.
Obrink, BioEssays, (1991) 13(5):227-233.
Odin et al., "Quantitative Determination of the Organ Distribution of the Cell Adhesion Molecule Cell—CAM 105 by Radioimmunoassay," Exp. Cell Res. (1987) 171:1-15.
Ogawa, K., Neuropathologica (1989) 77(3):244-253.
Ohta et al., "A possible role in sphingosine in induction of apoptosis by tumor necrosis factor-alpha in human neutrophils," FEBS Lett. (1994) 355:267-270.
Ojeda, et al., Cell. Immunol (1990) 125:535-539.
Okabe et al., "BE-23372M, a novel protein tyrosine kinase inhibitor I. producing organism, fermentation, isolation and biological activities," J. Antibiotics (1994) 47(3):289-293.
Okamoto et al., Proc. Nat'l Acad. Sci. USA (1994) 91:11045-11049.
Old, L.J., "Tumor necrosis factor (TNF)," Science (1985) 230(4726):630-632.
Old, L.J., "Tumor Necrosis Factor," Sci. Amer. (1988) 258:59-60 & 69-75.
Olivierio et al., EMBO J. (1987) 6(7):1905-1912.
O'Malley et al., Cancer Res. (1996) 56(8):1737-1741.
O'Malley et al., Mol. Endocrinol (1997) 11(6):667-673.
Omirulleh et al., Plant Mol. Biol. (1993) 21:415-428.
Ondek et al., EMBO J. (1987) 6:1017-1025.
Orlow et al., Cancer Res. (1994) 54:2848-2851.
Ornitz et al., Mol. Cell. Biol. (1987) 7(10):3466-3472.
Osmani et al., "Parallel activation of the NIMA and p34cdc2 cell cycle-regulated protein kinases is required to initiate mitosis in *A. nidulans*," Cell (1991) 67:283-291.
Ostrove et al., Virology (1981) 113:521-533.
Ouellette et al., "Expression of two 'immediate early' genes, Egr-1 and c-fos, in response to renal ischemia and during compensatory renal hypertrophy in mice," J. Clinc. Invest. (1990) 85:766-771.
Overell et al., J. Immunol. Methods(1991) 141:53-62.
Palmiter et al., Nature (1982) 300:611-615.
Papathanasiou, M. et al., Proc. Ann. Meet. Am. Assoc. Cancer Res. (1990) 31:A1802.
Papathanasiou et al., "Identification of an x-ray inducible human gene and its altered expression in ataxia telangiectasia," Proc. of the Amer. Assoc. for Cancer Res.(1990) 31:304.
Pape and Kim, Mol. Cell. Biol. (1989) 9(3):974-982.
Park et al., "Transcriptional control of viral gene therapy by cisplatin," J. Clin. Invest. (2002) 110(3):403-410.
Park, J. Biol. Chem (1995) 270:15467-15470.
Paskind et al., Virology (1975) 67:242-248.
Pech et al., Mol. Cell. Biol. (1989) 9(2):396-405.
Pelletier and Sonenberg, "Internal initiation of translation of eukaryotic mRNA directed by a sequence derived from poliovirus RNA," Nature (1988) 334:320-325.
Perales et al., Proc. Natl. Acad. Sci. (1994) 91:4086-4090.
Perez, R.P., "Cellular and molecular determinants if cisplatin resistance," Euro. J. Cancer (1998) 34(10):1535-1542.
Perez-Stable and Constantini, Mol. Cell. Bio. (1990) 10(3):1116-1125.
Physician's Desk Reference.
Picard et al., "A Lymphocyte-Specific Enhancer in the Mouse Immunoglobulin κ Gene," Nature (1984) 307:80-82.
Pinkert et al., "An Albumin Enhancer Located 10 kb Upstream Functions Along with its Promoter to Direct Efficient, Liver-Specific Expression in Transgenic Mice," Genes & Development (1987) 1:268-276.
Pleiman et al., Mol. Cell Biol. (1993) 13(9):5877-5887.
Plevova, P., "Prevention and treatment of chemotherapy- and radiotherapy- induced oral mucositis: a review," Oral Oncol. (1999) 35:453-470.
Poli and Cortese, Proc. Natl. Acad. Sci. USA (1989) 86:8202-8206.
Ponnazhagen et al., "Lack of Site-Specific Integration of the Recombinant Adeno-Associated Virus 2 Genomes in Human Cells," Human Gene Therapy (1997) 8:275-284.
Ponnazhagen et al., J. Gen. Virol. (1996) 77:1111-1122.
Ponta et al., Proc. Nat'l Acad. Sci. USA (1985) 82:1020-1024.
Porton et al., Mol. Cell. Biol. (1990) 10(3):1076-1083.
Post et al., Cell (1981) 24:555-565.
Post and Roizman, Cell (1981) 25:227-232.
Potrykus et al., Mol. Gen. Genet. (1985) 199:169-177.
Potter, H. et al., "Enhancer-dependent expression of human $\kappa$ immunoglobulin genes introduced into mouse pre-B lymphocytes by electroporation," Proc. Natl.' Acad. Sci. USA (1984) 81:7161-7165.
Preiss et al., J. Biol. Chem (1986) 261:8597-8600.
Prywes, R. and Roeder, R.G., Cell (1986) 47:777-784.
Prywes et al., Proc. Natl. Acad. Sci USA(1988) 85(19):7206-7210.
Pulverer, B.J. et al., "Phosphorylation of c-jun mediated by MAP kinases," Nature(1991) 353:670-674.
Queen and Baltimore, Cell (1983) 35:741-748.
Quinn et al., Mol. Cell. Biol. (1989) 9(11):4713-4721.
Quinones et al., "The egr-1 gene is induced by DNA-damaging agents and non-genotoxic drugs in both normal and neoplastic human cells," Life Sci. (2003) 72:2975-2992.

Quintans et al., Biochem. Biophys. Res. Commun (1994) 202:710-714.
Qureshi, S. et al., "v-Src activates mitogen-responsive transcription factor Egr-1 via serum response elements," J. Biol. Chem. (1991) 266(17):10802-10806.
Qureshi et al., J. Biol. Chem.(1991) 266(31):20594-20597.
Qureshi, S. et al., "v-Src activates both protein kinase C-dependent and independent signaling pathways in murine fibroblasts," Oncogene (1991) 6:995-999.
Racher et al., "Culture of 293 Cells in Different Culture Systems: Cell Growth and Recombinant Adenovirus Production," Biotechnology Techniques (1995) 9:3:169-174.
Radford and Murphy, Int. J. Radiat. Biol. (1994) 65:229-239.
Radler et al., Science (1997) 275:810-814.
Raff et al., "Programmed cell death and the control of cell survival," Philos. Trans. R. Soc. Lond. B. Biol. Sci. (1994) 345:265-268.
Ragot et al., "Efficient adenovirus-mediated transfer of a human minidystrophin gene to skeletal muscle of mdx mice," Nature (1993) 361:647-650.
Ramsamooj et al., "Differential expression of proteins in radioresistant and radiosensitive human squamous carcinoma cells," J. Natl. Cancer Inst. (1992) 84:622-628.
Rauch, D.P. et al., "Activity of gemcitabine and continuous infusion fluorouracil in advanced pancreative cancer," Oncology (2001) 60(1):43-48.
Rauscher, F.J., Cell(1988) 52:471-480.
Ravindranath et al., "Role of Gangliosides in Active Immunotherapy with Melanoma Vaccine," Intern. Rev. Immunol. (1991) 7:303-329.
Raza, S.M. et al., "Necrosis and glioblastoma: a friend or foe? A review and a hypothesis" Neurosurgery (2002) 51:2-13.
Redondo et al., Science (1990) 247(4947):1225-1229.
Reid, T. et al., "Resistance to killing by tumor necrosis factor in an adipocyte cell line caused by a defect in arachidonic acid biosynthesis," J. Biol. Chem. (1991) 266(25):16580-16586.
Reinhold-Hurek and Shub, Nature (1992) 357:173-176.
Reisman and Rotter, Mol. Cell. Biol. (1989) 9(8):3571-3575.
Remington's Pharmaceutical Sciences, 15th ed. 1035-1038 and 1570-1580.
Renan, Radiother. Oncol. (1990) 19:197-218.
Resendez, Jr., E. et al., Mol. Cell. Biol. (1988) 8(10):4579-4584.
Reuland et al., "Application of the murine anti-Gd-2 antibody 14.Gd-2a for diagnosis and therapy of neuroblastoma," Nucle. Med. Biol. (1991) 18:121-125.
Rewcastle et al., "Tyrosine kinase inhibitors. 3. Structure-activity relationships for inhibition of protein tyrosine kinases by nuclear-substituted derivatives of 2,2'-dithiobis (1-methyl-N-phenyl-1H-indole-3-carboxamide)," J. Med. Chem. (1994) 37:2033-2042.
Rhodes et al., "Transformation of maize by electroporation of embryos," Methods Mol. Biol. (1995) 55:121-131.
Rich et al., "Development and analysis of recombinant adenoviruses for gene therapy of cystic fibrosis," Human Gene Ther. (1993) 4:461-476.
Ridgway, Vectors: A survey of molecular cloning vectors and their uses, Rodriguez and Denhardt, eds., Stoneham: Butterworth, (1988) 467-492.
Rippe et al., Mol. Cell. Biol. (1989) 9(5):2224-2227.
Rippe, R.A. et al., "DNA-Mediated gene transfer into adult rat hepatocytes in primary culture," Mol. Cell. Biol. (1990) 10(2):689-695.
Rittling et al., Nucl. Acids Res. (1989) 17(4):1619-1633.
Robaye et al., "Tumor Necrosis Factor Induces Apoptosis (Programmed Cell Death) in Normal Endothelial Cells in Vitro," Amer. J. Pathol. (1991) 138:2:447-453.
Roehn, T.A. et al., "CCNU-dependent potentiation of TRAIL/Apo2L-induced apoptosis in human glioma cells in p53-independent but may involve enhance cytochrome c release," Oncogene (2001) 20(31):4128-4137.
Roeske, J.C. et al., Int. J. Radiat. Oncol. Biol. Phys. (1990) 19:1539-1548.
Roizman, R. and Sears, A.E., "Herpes simplex viruses and their replication," Virology, 2nd Ed. (Field, Knipe, Chanock, Melnick, Hirsch, Monath, Roizman, eds.) Raven Press, New York, (1990) 1795-1841.
Roizman and Sears, Fields' Virology, 3rd Ed., Fields et al. eds. (Raven Press, New York, NY) (1995) 2231-2295.
Rollins et al., Am. J. Respir. Cell Mol. Biol.(1992) 7:126-127.
Ron et al., Mol. Cell. Biology (1991) 11(5):2887-2895.
Rorsman et al., "Structural characterization of the human platelet-derived growth factor A-chain cDNA and gene: alternative exon usage predicts two different precursor proteins," Mol. Cell Biol. (1988) 8(2):571-577.
Rosen et al., Cell (1985) 41:813-823.
Rosenfeld et al., "In vivo transfer of the human cystic fibrosis transmembrane conductance regulator gene to the airway epithelium," Cell (1992) 68:143-155.
Rosenfeld et al., "Adenovirus-mediated transfer of a recombinant α1-antitrypsin gene to the lung epithelium in vivo," Science (1991) 252:431-434.
Rosenthal et al., Semin. Oncol. (1995) 22:13-17.
Rotenberg et al., "Deletion analysis of protein kinase C inactivation by calphostin C," Mol. Carcinog. (1995) 12:42-49.
Roth et al., "Retrovirus-mediated wild-type p53 gene transfer to tumors of patients with lung cancer," Nature Medicine (1996) 2(9):985-991.
Roux, P. et al., Proc. Natl. Acad. Sci. USA (1989) 86(23):9079-9083.
Rubin et al., "Correlation between the anticellular and DNA fragmenting activities of tumor necrosis factor," Cancer Res.(1988) 48:6006-6010.
Ruff and Gifford, Infect. Immun. (1981) 31(1):380-385.
Ryan et al., EMBO J.(1989) 8(6):1785-1792.
Ryder, K. et al., Proc. Natl. Acad. Sci. USA (1988) 85:1487-1491.
Saito, R. et al., "Convection-enhanced delivery of tumor necrosis factor-related apoptosis-inducing ligand with systemic administration of temozolomide prolongs survival in an intracranial glioblastoma xenograft model," Cancer Res. (2004) 64(19)6848-6862.
Sakamoto, K.M. et al., "5' upstream sequence and genomic structure of the human primary response gene, EGR-1/TIS8," Oncogene (1991) 6:867-871.
Sakihama et al., "Differential Susceptibility of a Rat Glioma Cell Line and its Clones to Herpes Simplex Virus Types 1 and 2," Acta. Virol. (1991) 35:127-134.
Sambrook et al., Molecular cloning: A laboratory manual (1989) Cold Spring Harbor Laboratory, Cold Spring Harbor, New York.
Sambrook et al., *Molecular Cloning*, Cold Spring Harbor Laboratory Press, Cold Spring Harbor, NY (2000).
Samuels et al., "Increased glutathione peroxidase activity in a human sarcoma cell line with inherent doxorubicin resistance," Cancer Res. (1991) 51:521-527.
Samulski et al., EMBO J. (1991) 10:3941-3950.
Sanchez and Elledge, Bioessays (1995) 17:545-548.
Santana et al., Cell (1996) 88:189-199.
Sariban, E. et al., J. Clin. Invest.(1988) 81:1506-1510.
Sartorius, U. et al., "Molecular mechanisms of death-receptor-mediated apoptosis," Chembiochem. (2001) 2:21-29.
Sarver et al., Science (1990) 247:1222-1225.
Satake et al., "Biological activities of oligonucleotides spanning the F9 point mutation within the enhancer region of polyoma virus DNA," J. Virology (1988) 62(3):970-977.
Sausville et al., "Clinical pharmacology of UCN-01: initial observations and comparison to preclinical models," Cancer Chemother. Pharmacol. (1998) 42:S54-S59.
Scanlon, M. et al., Cell Biol. (1989) 86:182-186.
Scanlon et al., Proc. Natl. Acad. Sci. USA (1991) 88:10591-10595.
Schaffner et al., J. Mol. Biol. (1988) 201:81-90.
Schorpp, M. et al., "UV-induced extracellular factor from human fibroblasts communicates the UV response to nonirradiated cells," Cell (1984) 37:861-868.
Schroter et al., "Increased p34cdc2-dependent kinase activity during apoptosis: a possible activation mechanism of Dnase I leading to DNA breakdown," Eur. J. Cell Biol. (1996) 69:143-150.
Schwartz et al., "Potentiation of apoptosis by treatment with the protein kinase C-specific inhibitor safingol in mitomycin C-treated gastric cancer cells," J. Natl. Cancer Inst. (1995) 87:1394-1399.
Searle et al., Mol. Cell. Biol. (1985) 5(6):1480-1489.

Seeburg "The Human Growth Hormone Gene Family" DNA (1982) 1:239-249.
Seetharam, S. et al., "Modulation of the apoptotic response of radiation resistant xenografts of human carcinoma by *Pseudomonas* exotoxin-chimeric protein," Cancer Res. (1998) 58:3215-3220.
Senturker et al., "Induction of apoptosis by chemotherapeutic drugs without generation of reactive oxygen species," Arch. Biochem. Biophysics (2002) 397(2):262-272.
Senzer et al., "TNFerade biologic, an adenovector with a radiation-inducible promoter, carrying the human tumor necrosis factor alpha gene: a phase I study in patients with solid tumors," J. Clinc. Oncol. (2004) 22(4):592-601.
Serrano et al., Nature (1993) 366:704-707.
Serrano et al., Science (1995) 267:249-252.
Sersa, G. et al., "Anti-tumor effects of tumor necrosis factor alone or combined with radiotherapy," Int. J. Cancer (1988) 42:129-134.
Seung, L.P. et al., "Genetic radiotherapy overcomes tumor resistance to cytotoxic agents," Cancer Research (1995) 55:5561-5565.
Shafman, T.D. et al. "Defective induction of stress-activated protein kinase activity in ataxia-telangiectasia cells exposed to ionizing radiation," Cancer Res. (1995) 55:3242-3245.
Shao et al., "Abrogation of an S-phase checkpoint and potentiation of camptothecin cytotoxicity by 7-hydroxystaurosporine (UCN-01) in human cancer cell lines, possibly influenced by p53 function," Cancer Res. (1997) 57:4029-4035.
Sharma et al., "An open-label, phase I, dose-escalation study of tumor necrosis factor-α (TNFerade™ biologic gene transfer with radiation therapy for locally advanced, recurrent, or metastatic solid tumors," Human Gene Therapy (2001) 12:1109-1131.
Sharp, Genes Dev. (1999) 13:139-141.
Sharp and Marciniak, Cell (1989) 59:229-230.
Sharp and Zamore, Science (2000) 287:2431-2433.
Shaul and Ben-Levy, EMBO J. (1987) 6(7):1913-1920.
Shaw et al., Cell(1989) 56:563-572.
Shayakhmetov, D.M. et al., "Analysis of adenovirus sequestration in the liver, transduction of hepatic cells, and innate toxicity after injection of fiber-modified vectors," J. Virol. (2004) 78(10):5368-5381.
Shen et al., J. Biol. Chem. (1996) 271:148-152.
Sheng et al., Mol. Cell Biol. (1988) 8(7):2787-2796.
Sherman et al., Mol. Cell. Biol. (1989) 9(1):50-56.
Sherman et al., "Ionizing radiation regulates expression of the c-jun photooncogene," Proc. Natl. Acad. Sci USA (1990) 87(15):5663-5666.
Sherman, M.L. et al., "Transcriptional and post-transcriptional regulation of c-jun expression during monocytic differentiation of human myeloid leukemic cells," J. Biol. Chem. (1990) 265:3320-3323.
Sherman et al., "Ionizing radiation regulates expression of the c-jun proto-oncogene," Proc. Am. Assoc. Cancer Res. (1990) 31(0):13.
Sherman, M. et al., "Regulation of tumor necrosis factor gene expression by ionizing radiation in human myeloid leukemia cells and peripheral blood monocytes," Amer. Soc. Clin. Invest. (1991) 87:1794-1797.
Shi et al., "Premature p34cdc2 activation required for apoptosis," Science (1994) 263:1143-1145.
Shirahama et al., "Sphingosine induces apoptosis in androgen-independent human prostaticcarcinoma DU-145 cells by suprression of bcl-X(L) gene expression," FEBS Lett. (1997) 407:97-100.
Shiraishi et al., Transplant International (1997) 10:207-211.
Sinha et al., "Relationships between proto-oncogene expression and apoptosis induced by anticancer drugs in human prostate tumor cells," Biochim. Biophys. ACTA (1995) 1270:12-18.
Sleigh and Lockett, J. EMBO (1985) 4(13B):3831-3837.
Slungaard et al., J. Exp. Med. (1990) 171:2025-2041.
Smets, "Programmed cell death (apoptosis) and response to anti-cancer drugs," Anti-Cancer Drugs (1994) 5(1):3-9.
Smith and Moss, Gene (1983) 25:21-28.
Smith and Rutledge, "Random study of hexamethylmelamine, 5-fluorouracil, and melphalan in treatment of advanced carcinoma of the ovary," Nat'l. Cancer Inst. Monogr. (1975) 42:169-172.
Sodhi and Gupta, "Increased release of hydrogen peroxide (H2O2) and superoxide anion (O2) by murine macrophages in vitro after cis-platin treatment," Int. J. Immunopharmacol. (1986) 8(7):709-714.
Song et al., Cytotoxic T Lymphocyte Responses to Proteins Encoded by Heterologous Transgenes Transferred in Vivo by Adenoviral Vectors, Human Gene Therapy (1997) 8:1207-1217.
Spalholz et al., Cell (1985) 42:183-191.
Spandau and Lee, J. Virology (1988) 62(2):427-434.
Spandidos and Wilkie, EMBO J. (1983) 2(7):1193-1199.
Speigelman et al., J. Biol. Chem. (1989) 264(3):1811-1815.
Spriggs et al., "Recombinant human tumor necrosis factor administered as a 24-hour intravenous infusion a Phase I and pharmacologic study," J. Natl. Cancer Inst. (1988) 80:1039-1044.
Spriggs et al., "Clinical Studies withTumour Necrosis Factor," Tumour Necrosis Factor and Related Cytotoxins (1987) 206-227.
Srivastava et al., J. Virol. (1983) 45(2):555-564.
Staba, M-J et al., "Adenoviral TNF-α gene therapy and radiation damage tumor vasulature in a human malignant glioma xenograft," Gene Therapy (1998) 5:293-300.
Staba, M.J. et al., Cancer Gene Therapy (2000) 7:13-19.
Stabel, S., "Protein Kinase C—An Enzyme and its Relatives," Cancer Biology (1994) 5:277-284.
Stephens et al., "The Bovine Papillomavirus Genome and its Uses as a Eukaryotic Vector," Biochem. J. (1987) 248:1-11.
Stephens et al., Radiat. Res. (1993) 135:75-80.
Stephens et al., Radiation Research (1991) 127:308-316.
Stewart, L.A., "Chemotherapy in adult high-grade glioma: a systematic review and meta-analysis of individual patient data from 12 randomised trials." Lancet (2002) 359(9311):1011-1018.
Stone et al, "Recombinant human gamma interferon administered by continuous intravenous infusion in acute myelogenous leukemia and myelodysplastic syndromes," Am. J. Clinc. Oncol. (1993) 16:159-163.
Stopera, S. et al., Carcinogen.(1992) 13(4):573-578.
Stratford et al., "Evaluation of the Transfer and Expression in Mice of an Enzyme-Encoding Gene Using a Human Adenovirus Vector," Human Gene Therapy (1990) 1:241-256.
Strum et al., J. Biol. Chem. (1994) 269:15493-15497.
Stuart et al., Nature (1985) 317:828-831.
Stumpo et al., J. Biol. Chem. (1988) 263(4):1611-1614.
Stupp, R. et al., "Promising survival for patients with newly diagnosed glioblastoma multiforme treated with concomitant radiation plus temozolomide followed by adjuvant temozolomide," J. Clin. Oncol. (2002) 20(5):1375-1382.
Sugarman et al., Science(1985) 230:943-945.
Suggs, S.V. et al., "cDNA sequence of the human cellular early growth response gene Egr-1," Nucleic Acids Res. (1990) 18(14):4283.
Sukhatme et al., "A zinc finger-encoding gene coregulated with c-fos during growth and differentiation, and after cellular depolarization," Cell (1988) 53(1):37-43.
Sukhatme, V.P. et al., "A novel early growth response gene rapidly induced by fibroblast, epithelial cell and lymphocyte mitogens," Oncogene (1987) 1:343-355.
Sulkowska et al., "Cyclophosphamide-induced generation of reactive oxygen species. Comparison with morphological changes in type II alveolar epithelial cells and lung capillaries," Exp. Toxicol. Pathol. (1998) 50:209-220.
Sullivan and Peterlin, Mol. Cell Biol. (1987) 7(9):3315-3319.
Suzuki et al., Cancer Res. (1992) 52:734-736.
Szumiel, Int. J. Radiat. Bio. (1994) 66:329-341.
Tabara et al., Cell (1999) 99:123-132.
Takebe et al., Mol. Cell. Biol. (1988) 8(1):466-472.
Tanaka, N. et al., "Response of adenosquamous carcinoma of the pancreas to interferon-α, tumor necrosis factor-α and 5-fluorouracil combined treatment," Anticancer Research (1994) 14:2739-2742.
Tartaglia, L.A. et al., "Two TNF receptors," Immunology Today (1992) 13:151-153.
Tartaglia, L.A. et al., "Tumor necrosis factor receptor signaling," J. Biol. Chem. (1992) 267:4304-4307.
Tartaglia, L.A. et al., "Tumor necrosis factor's cytotoxic activity is signaled by the p55 TNF receptor," Cell (1993) 73:213-216.
Tartaglia et al., "A novel domain within the 55 kd TNF receptor signals cell death," Cell (1993) 74:845-853.
Tavernier et al., Nature (1983) 301:634-636.
Taylor and Kingston, Mol. Cell. Biol. (1990) 10(1):165-175.

Taylor and Kingston, Mol. Cell. Biol. (1990) 10(1):176-183.
Taylor et al., "Stimulation of the Human Heat Shock Protein 70 Promoter in Vitro by Simian Virus 40 Large T Antigen," J. Biol. Chem. (1989) 264:27:16160-16164.
Teicher et al., "Prostate carcinoma response to cytotoxic therapy: in vivo resistance," In Vivo (1997) 11(6):453-462.
Temin, "Retrovirus Vectors for Gene Transfer: Efficient Integration into and Expression of Exogenous DNA in Vertebrate Cell Gehones," Gene Transfer (1986) 149-187.
Teng, M.N. et al., "Long-term inhibition of tumor growth by tumor necrosis factor in the absence of cachexia or T-cell immunity," Proc. Natl. Acad. Sci. USA (1991) 88:3535-3539.
Thiesen et al., J. Virology (1988) 62(2):614-618.
Thom et al., J. Clin. Oncol. (1995) 13:264-273.
Thomsen, D.R. et al., Proc. Natl. Acad. Sci. USA (1984) 81:659-663.
Thompson and Fields, J. Biol. Chem. (1996) 271:15045-15053.
Tiefenbrunn, A.J., Am. J. Cardiol.(1992) 69:3A-11A.
Top et al., "Immunization with live types 7 and 4 adenovirus vaccines. II. Antibody response and protective effect against acute respiratory disease due to adenovirus type 7," J. Infect. Dis. (1971) 124:155-160.
Tratschin et al., Mol. Cell Biol. (1984) 4(10):2072-2081.
Treisman, R., "The SRE: A Growth Factor Responsive Transcriptional Regulator," Cancer Biology (1990) 1:47-58.
Treisman, R., "Identification of a Protein-Binding Site that Mediates Transcriptional Response of the c-fos Gene to Serum Factors," Cell (1986) 46:567-574.
Treisman, Cell (1985) 42:889-902.
Trienzenberg et al., Genes & Development(1988) 2:718-729.
Tronche et al., "Anatomy of the Rat Albumin Promoter," Mol. Biol. Med. (1990) 7:173-185.
Tronche et al., Mol. Cell. Biol. (1989) 9(11):4759-4766.
Trubetskoy et al., Bioconjugate Chem.(1992) 3:323-327.
Trudel et al., "A 3' Enhancer Contributes to the Stage-Specific Expression of the Human β-Globin Gene," Genes & Development (1987) 1:954-961.
Tsai-Morris, C.-H. et al., "5' flanking sequence and genomic structure of Egr-1, a murine mitogen inducible zinc finger encoding gene," Nucleic Acids Research(1988) 16:8835-8846.
Tsumaki, N. et al., Modular arrangement of cartilage- and neural tissue-specific cis- elements in the mouse alpha2(XI) collagen promoter, J. Biol. Chem. (1998) 273(36):22861-22864.
Tur-Kaspa et al., Mol. Cell Biol. (1986) 6:716-718.
Tyndall et al., Nuc. Acids. Res. (1981) 9(23):6231-6250.
Uckun et al., Int. J. Radiol. Onc. Biol. Phys.(1989) 16:415-435.
Uckun et al., "Ionizing radiation stimulates unidentified tyrosine-specific protein kinases in human b-lymphocyte precursors, triggering apoptosis and clonogenic cell death," Proc. Natl. Acad. Sci. USA (1992) 89:9005-9009.
Uckun et al., "Tyrosine phosphorylation is a mandatory proximal step in radiation-induced activation of the protein kinase C signaling pathway in human B-lymphocyte precursors," Proc. Natl. Acad. Sci. USA (1993) 90:252-256.
Uckun et al., Science (1995) 267:886-891.
Ueta et al., "Manganese superoxide dismutase negatively regulates the induction of apoptosis by 5-flurouracil, peplomycin and γ-rays in squamous cell carcinoma cells," Jpn. J. Cancer Res. (1999) 90:555-564.
Umbas et al., Cancer Res. (1992) 52:5104-5109.
Unlap, T. et al., Nucleic Acids Res.(1992) 20:897-902.
Uzvolgyi et al., "Reintroduction of a normal retinoblastoma gene into refinoblastoma and ostrosarcoma cells inhibits the replication associated function of SV40 large T antigen," Cell Growth Diff. (1991) 2:297-303.
Van Brussel et al., "Chemosensitivity of prostate cancer cell lines and expression of multidrug resistance-related proteins," Eur. J. Cancer (1999) 35:664-671.
Van Der Donk et al., "Detection of a new substrate-derived radical during inactivation of ribonucleotide reductase from Escherichia coli by gemcitabine 5'-diphosphate," Biochemistry (1998) 37:6419-6426.

Van Engeland, M. et al., "Annexin V-affinity assay: a review on an apoptosis detection system based on phosphatidylserine exposure," Cytometry (1998) 31:1-9.
Van Straaten, F. et al., Proc. Natl. Acad. Sci. USA (1983) 80:3183-3187.
Vannice and Levinson, J. Virology (1988) 62(4):1305-1313.
Varbiro et al., "Direct effect of taxol on free radical formation and mitochondrial permeability transition," Free Radio. Biol. Med, (2001) 31:548-558.
Varmus et al., Cell (1981) 25:23-36.
Vasseur et al., Proc. Natl. Acad. Sci. USA (1980) 77(2):1068-1072.
Venable et al., J. Biol. Chem. (1994) 269:26040-26044.
Verheij et al., Nature (1996) 380:75-79.
Verma and Somia, "Gene therapy—promises, problems and prospects," Nature (1997) 389:239-242.
Vilcek et al. J. Exp. Med. (1986) 163:632-643.
Vile et al., "In vitro and in vivo targeting of gene expression in melanoma cells," Cancer Research (1993) 53:962-967.
Vogel, S.N. and Hogan, M., "Role of cytokines in endotoxin-mediated host responses," Immunophysiology, Role of Cells and Cytokines in Immunity and Inflammation (Oppenheim, ed) (1990) Oxford University Press, London, 238-258.
Vokes and Weichselbaum, J. Clin. Oncol. (1990) 8:911-934.
Vokes et al., "Head and neck cancer," N. Engl. J. Med. (1993) 328:184-194.
Waddick et al., Blood(1991) 77:2364-2371.
Wagner et al., Proc. Natl. Acad. Sci. (1990) 87(9):3410-3414.
Wallach, J. Immunol. (1984) 132(5):2464-2469.
Walsh, K., Mol. Cell. Biol.(1989) 9(5):2191-2201.
Walther et al., "Retrovirus-mediated gene transfer of tumor necrosis factor alpha into colon carcinoma cells generates a growth inhibition," (1993) 13:1565-1573.
Walther and Stein, J. Mol. Med., (1996) 74:379-392.
Wang and Calame, Cell (1986) 47:241-247.
Wang, A.M. et al., Science (1985) 228:149-154.
Wang et al., "UNC-01: a potent abrogator of G2 checkpoint function in cancer cells with disrupted p53," J. Natural Cancer Inst. (1996) 88:956-965.
Ward et al., "The effect of steroids on radiation-induced lung disease in the rat," Rad. Res. (1993) 136:22-28.
Ward et al., "The pulmonary response to sublethal thoracic irradiation in the rat," Rad. Res. (1993) 136:15-21.
Watanabe et al., Cancer Res. (1988) 48:2179-2183.
Waters, C.M. et al., "Identification and characterisation of the egr-1 gene product as an inducible, short-lived, nuclear phosphoprotein," Oncogene (1990) 5:669-674.
Watson, J.D. et al., Molecular Biology of the Gene, 4th Ed., Benjamin/Cummings Publishing Co., Inc., Menlo Park, California (1987) 313.
Watt et al., Proc. Natl. Acad. Sci. (1986) 83(2):3166-3170.
Weber et al., Cell (1984) 36:983-992.
Weichselbaum, R. et al., "X-ray sensitivity of fifty-three human diploid fibroblast cell strains from patients with characterized genetic disorders," Cancer Research (1980) 40:920-925.
Weichselbaum et al., "Inherently radioresistant cells exist in some human tumors," Proc. Natl. Acad. Sci. USA (1985) 82:4732-4735.
Weichselbaum et al., "Radiation-resistant and repair-proficient human tumor cells may be associated with radiotherapy failure in head-and neck-cancer patients," Proc. Natl. Acad. Sci. USA(1986) 83:2684-2688.
Weichselbaum et al., "In vitro radiobiological parameters of human sarcoma cell lines," Int. J. Radiation Oncology Biol. Phys.(1988) 15:937-942.
Weicheselbaum et al., "Possible applications of biotechnology to radiotherapy," Eur. J. Cancer (1991) 27(4):405-407.
Weichselbaum et al., "Biological consequences of gene regulation after ionizing radiation exposure," J. Natl. Cancer Inst. (1991) 83(7):480-484.
Weichselbaum et al., "Gene therapy targeted by ionizing radiation," Int. J. Radiation Oncology Biol. Phys. (1992) 24:565-567.
Weichselbaum et al., "Gene therapy targeted by radiation preferentially radio-sensitizes tumor cells," Cancer Research (1994) 54:4266-4268.

Weichselbaum, R.R. et al., "Radiation induction of immediate early genes: effectors of the radiation-stress response," Int. J. Radiat. Oncol. Biol. Phys. (1994) 30:229-234.

Weichselbaum, R.R. et al., "Ionizing radiation: a molecular switch for gene therapy," Internet Book of Gene Therapy (1995) 205-210.

Weichselbaum et al., "Molecular targeting of gene therapy and radiotherapy," Acta Oncol. (2001) 40:735-738.

Weil et al., "Constitutive expression of the machinery for programmed cell death," J. Cell Biol. (1996) 133:1053-1059.

Weinberg, Science (1991) 254(5035):1138-1146.

Weinberger et al., "Localization of a Repressive Sequence Contributing to B-Cell Specificity in the Immumoglobulin Heavy-Chain Enhancer," Mol. & Cell. Biol. (1988) 988-992.

Werthman et al., Journal of Urology (1996) 155(2):753-756.

Wiedenmann et al., J. Cancer Res. Clin. Oncol. (1989) 115:189-192.

Wiegmann et al., Cell (1994) 78:1005-1015.

Wilson et al., Nucleic Acids Res.(1978) 5(2):563-581.

Wilson et al., "Implantation of vascular grafts lined with genetically modified endothelial cells," Science (1989) 244:1344-1346.

Winans et al., J. Bacteriology (1985) 161(3):1219-1221.

Wincott et al., Nucleic Acids Res. (1995) 23(14):2677-2684.

Witte et al., "Effects of irradiation on the release of growth factors from cultured bovine, porcine, and human endothelial cells," Cancer Research(1989) 49:5066-5072.

Wolfe et al., "Restoration of Normal Lysosomal Function in Mucopolsaccharidosis Type VII Cells by Retroviral Vector-Mediated Gene Transfer," Proc. Natl. Acad. Sci. (1990) 87:2877-2881.

Woloschak et al., "Modulation of gene expression in Syrian hamster embryo cells following ionizing radiation," Cancer Res.(1990) 50:339-344.

Wong et al., Gene (1980) 10:87-94.

Wong, G.W.H. and Goeddel, D.V., "Induction of manganous superoxide dismutase by tumor necrosis factor: Possible protective mechanism," Science(1988) 242:941-944.

Wong, G.H.W. et al., "Manganous superoxide dismutase is essential for cellular resistance to cytotoxicity of tumor necrosis factor," Cell(1989) 58:923-931.

Wong, G. et al., "Tumor necrosis factor selectively sensitizes human immunodeficiency virus-infected cells to heat and radiation," Proc. Natl. Acad. Sci. USA(1991) 88:4372-4376.

Wong, G.H. et al., "Antiviral activity of tumor necrosis factor is signaled through the 55-kDa receptor, type 1 TNF," J. Immunol. (1992) 149(10):3350-3353.

Wong, S-S. et al., "Superinduction of TNF-α and IL-6 in macrophages by vomitoxin (deoxynivalenol) modulated by mRNA stabilization," Toxicology (2001) 161:139-149.

Wu et al., "Liver-Detected Gene Delivery," Advanced Drug Delivery Rev. (1993) 12:159-167.

Wu and Wu, Biochem. (1988) 27:887-892.

Wu, G.Y. and Wu, C.H., "Receptor-mediated in vitro gene transformation by a soluble DNA carrier system," J. Biol. Chem. (1987) 262:(10)4429-4432.

Wu, H.K. et al., "Promoter-dependent tissue-specific expressive nature of imprinting gene, insulin-like growth factor II, in human tissues," Biochem. Biophys. Res. Commun. (1997) 233(1):221-226.

Yamanashi et al., "Activation of Src-like protein-tyrosine kinase Lyn and its association with phosphatidylinositol 3-kinase upon B-cell antigen receptor-mediated signaling," Proc. Natl. Acad. Sci. USA (1992) 89:1118-1122.

Yamauchi et al., "Intracellular hydroxyl radical production induced by recombinant human tumor necrosis factor," Cancer Res.(1989) 49:1671-1675.

Yamini, B et al., "Transcriptional targeting of adenovirally delivered tumor necrosis factor alpha by temozolomide in experimental glioblastoma," Cancer Res. (2004) 64(18):6381-6384.

Yang et al., Proc. Natl. Acad. Sci USA (1990) 87:9568-9572.

Young et al., N. Engl. J. Med. (1978) 7, 299(23):1261-1266.

Yuan, Z.M. et al., "Activation of protein kinase C δ by the c-Abl tyrosine kinase in response to ionizing radiation," Oncogene (1998) 16:1643-1648.

Zafarullah et al., "Molecular mechanisms of N-acetylicysteine actions," Cell Mol. Life Sci. (2003) 60:6-20.

Zhou and Elledge, "Isolation of crt mutants constitutive for transcription of the DNA damage inducible gene RNR3 in *Saccharomyces cerevisiae*," Genetics (1992) 131:851-866.

Zhou et al., "Stably Transformed Callus of Wheat by Electroporation-Induced Direct Gene Transfer," Plant Cell Reports (1993) 12:612-616.

Zimmerman et al., "Oxidative damage in murine tumor cells treated in vitro by recombinant human necrosis factor," Cancer Res.(1989) 49:1644-1648.

Zerial et al., "The Product of a Novel Growth Factor Activated Gene, fos B, Interacts with JUN Proteins Enhancing their DNA Binding Activity," EMBO J. (1989) 8:3:805-813.

Zucker et al., Proc. Soc. Exp. Biol. Med.(1991) 198:693-702.

Zufferey et al., "Multiply attenuated lentiviral vector achieves efficient gene delivery in vivo," Nat. Biotechnol. (1997) 15(9):871-875 "The Control of Gene Therapy with Radiation".

* cited by examiner

ACTIVATION OF EGR-1 PROMOTER BY DNA DAMAGING CHEMOTHERAPEUTICS

CROSS REFERENCE TO RELATED APPLICATIONS

This application is a continuation-in-part of U.S. application Ser. No. 10/117,442, filed Apr. 5, 2002, now abandoned, which claims priority to U.S. Provisional Application No. 60/282,040, filed Apr. 6, 2001, and is also a continuation-in-part of U.S. application Ser. No. 10/795,090, filed Mar. 5, 2004, now abandoned, which claims priority to U.S. Provisional Application No. 60/452,489, filed Mar. 6, 2003. The entire texts of the above-referenced disclosures are hereby incorporated by reference.

INTRODUCTION

Therapy for cancer has largely involved the use of chemotherapy, in which highly toxic chemicals are given to the patient, and/or radiotherapy, in which toxic doses of radiation are administered. Chemotherapeutics that have been used successfully to combat certain cancers are frequently ineffective against other cancers, or are effective only at doses that are so high as to cause unacceptable toxicity. Although cancer chemotherapy has advanced dramatically in recent years, very few chemotherapeutic agents are curative in human cancer treatment when delivered alone. First, any single agent may only target a subset of the total population of malignant cells present, leaving a subpopulation of cancerous cells to continue growing. Second, cells can develop resistance upon prolonged exposure to a drug. Most chemotherapeutic agents must be delivered in combination with other agents to achieve curative effects.

Another approach to treating cancer involves gene therapy. Gene therapy involves the transfer of a foreign polynucleotide into a cancer cell, often a polynucleotide encoding a polypeptide that is a tumor suppressor or inducer of apoptosis, under conditions suitable for expression of the therapeutic polypeptide. Once expressed, the polypeptide confers a beneficial effect on the tumor cell by either slowing its growth, inhibiting its metastatic potential, or inducing apoptosis. However, the clinical effectiveness of cancer gene therapy has been limited by the lack of control of therapeutic gene expression within the tumor and selective targeting of the vector to the tumor.

Combination therapies, which employ two or more agents with differing mechanisms of action and differing toxicities, have been useful for circumventing drug resistance and increasing the target cell population. In addition, certain combinations of agents may be synergistic; in other words, their combined effect is greater than predicted based on their individual activities. Thus, combining different agents can be a powerful strategy for treating cancer. However, combination therapies do not consistently provide the desired therapeutic effect and may contribute to multi-drug resistance. In addition, antagonistic or biochemical interactions between the different therapies may lead to a reduced effectiveness and/or increased cytotoxicity for the combination than for either treatment alone.

SUMMARY

The present invention relates to transcriptional targeting, i.e., method of delivering a construct encoding a therapeutic polypeptide in conjunction with a chemotherapeutic agent to a subject, wherein the chemotherapeutic agent induces expression of the polypeptide. Such methods allow for the targeted expression of a therapeutic polypeptide that is directly or indirectly toxic to neoplastic and/or malignant cells, thereby avoiding toxicity that may be associated with systemic administration of the polypeptide. In addition, the combined treatment effect of the therapeutic polypeptide with chemotherapy may enhance the therapeutic response of neoplastic and/or malignant cells or a tumor to a greater degree than treatment with either therapy alone.

Moreover, transcriptional targeting methods employing co-administration of a construct comprising a promoter operably linked to a polynucleotide encoding a therapeutic polypeptide and a chemotherapeutic agent are useful when it is possible to infuse or directly inject gross tumors, even in the presence of micrometastases, since the construct/chemotherapeutic agent combination is effective against gross tumor and micrometastatic disease.

In one embodiment, the invention provides methods of inducing expression of a polypeptide in a cell, comprising concomitantly contacting the cells with a construct comprising an Egr-1 promoter operably linked to a polynucleotide encoding the polypeptide, and at least one chemotherapeutic agent, wherein the chemotherapeutic agent induces expression of the polypeptide.

In another embodiment, the invention provides a method of inhibiting a neoplastic cell. The method comprises concomitantly contacting the cell with: a) a construct comprising an Egr-1 promoter operably linked to a polynucleotide encoding TNF-$\alpha$; and b) a chemotherapeutic agent.

In a further embodiment, the present invention provides methods of inhibiting or reducing the growth of a tumor in a subject, comprising co-administering to the subject: a) a construct comprising an Egr-1 promoter operably linked to a polynucleotide encoding TNF-$\alpha$; and b) a chemotherapeutic agent capable of inducing expression of the TNF-$\alpha$ from the Egr-1 promoter.

In another embodiment, the present invention provides methods of enhancing the antiproliferative effect of chemotherapy in a subject, comprising co-administering to the subject therapeutically effective amounts of a construct comprising a promoter operably linked to a polynucleotide encoding TNF-$\alpha$ and a chemotherapeutic agent, wherein the expression of TNF-$\alpha$ enhances the antiproliferative effect of the chemotherapy.

Other advantages and a fuller appreciation of specific adaptations, compositional variations, and physical attributes of the invention will be gained upon an examination of the following detailed description of exemplary embodiments, taken in conjunction with the figures.

DETAILED DESCRIPTION OF SEVERAL EMBODIMENTS

Figure 1:
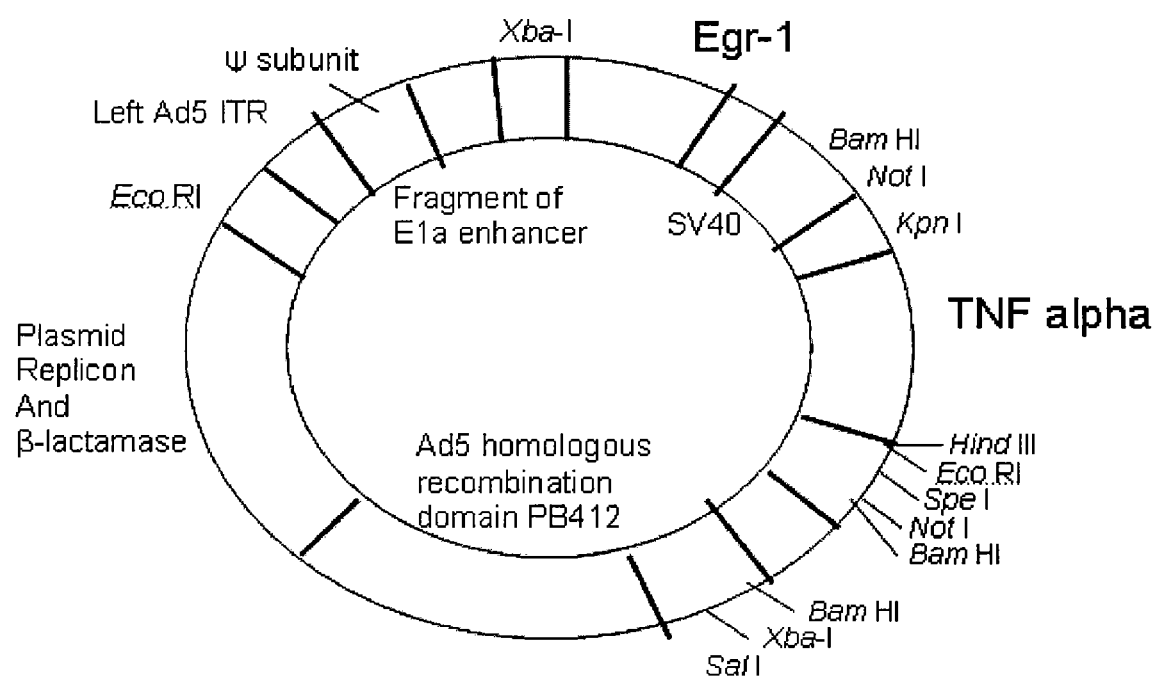
FIG. 1 is a schematic diagram of an adenoviral vector comprising an Egr-1 promoter operably linked to a polynucleotide encoding TNF-$\alpha$ (referred to herein below as "Ad.Egr.TNF").
Figure 2:
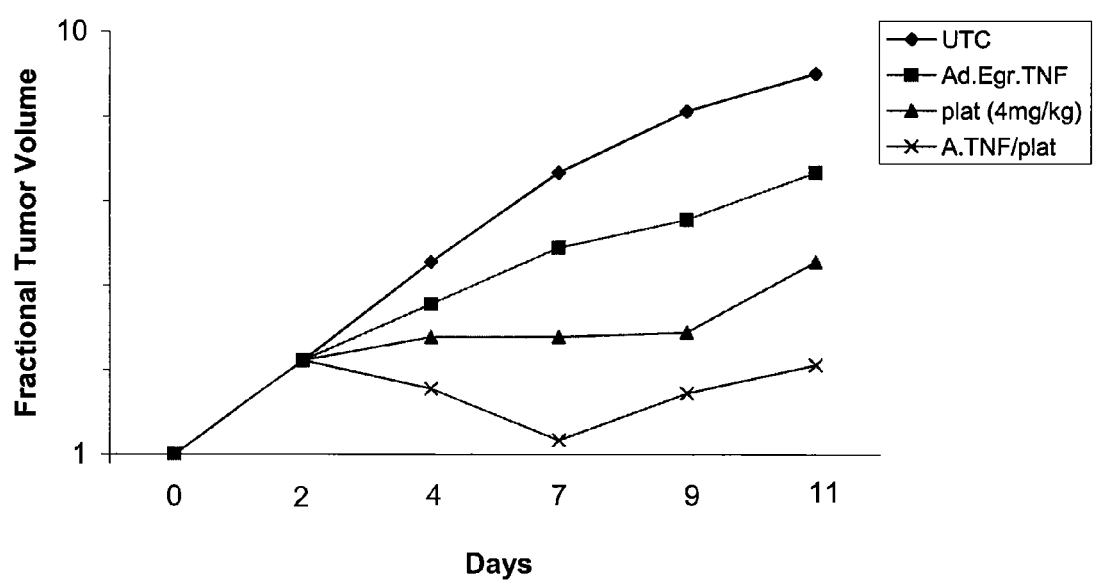
FIG. 2 is a graph comparing changes in fractional tumor volumes over time between untreated cells (UTC), and cells contacted with Ad.Egr.TNF, with and without cisplatin.
Figure 3:
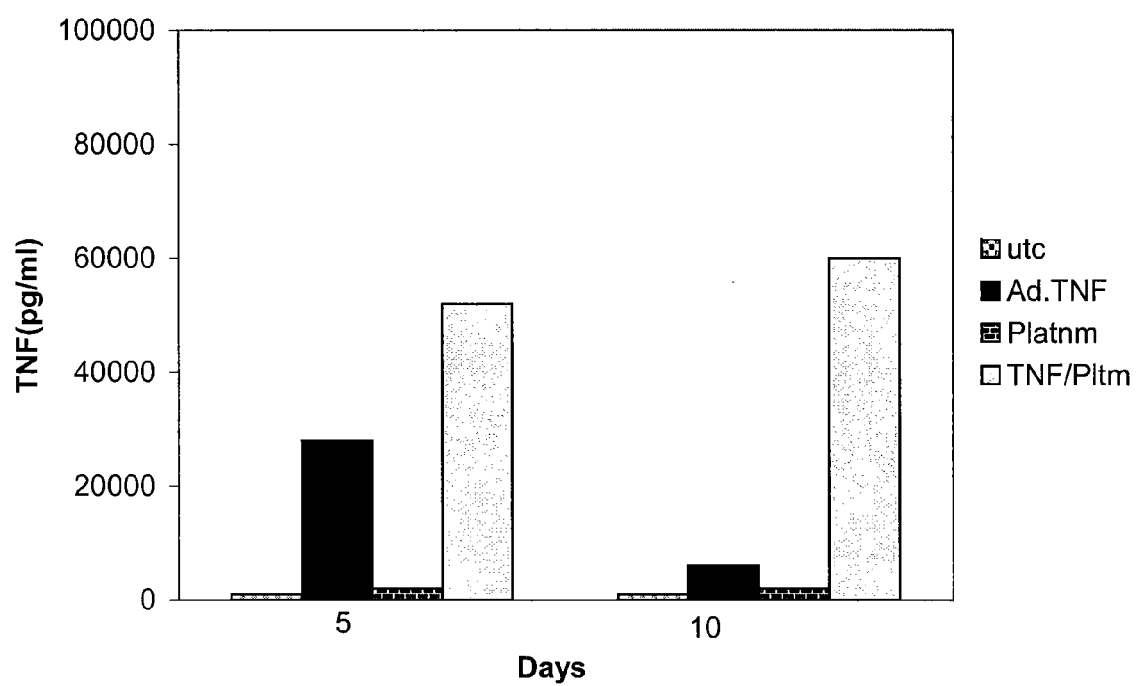
FIG. 3 is a graph comparing levels of TNF-$\alpha$ expression in UTC, and cells contacted with Ad.Egr.TNF, with and without cisplatin.
Figure 4:
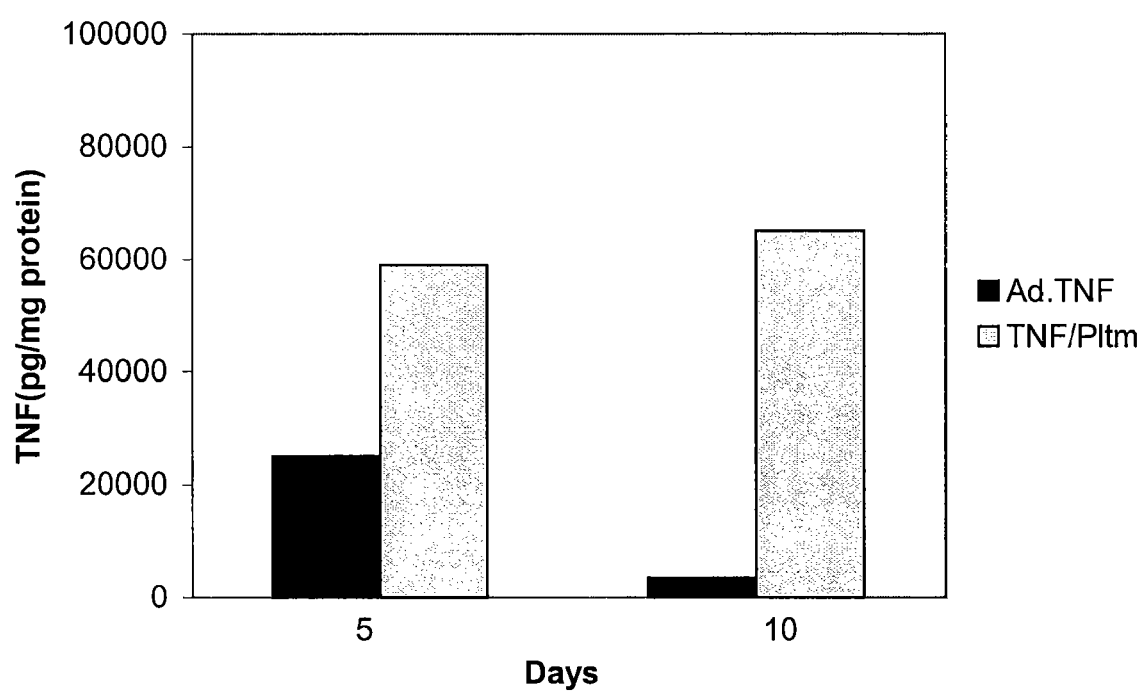
FIG. 4 is a graph comparing levels of TNF-$\alpha$ induction over time in cells contacted with Ad.Egr.TNF, with and without cisplatin.
Figure 5:
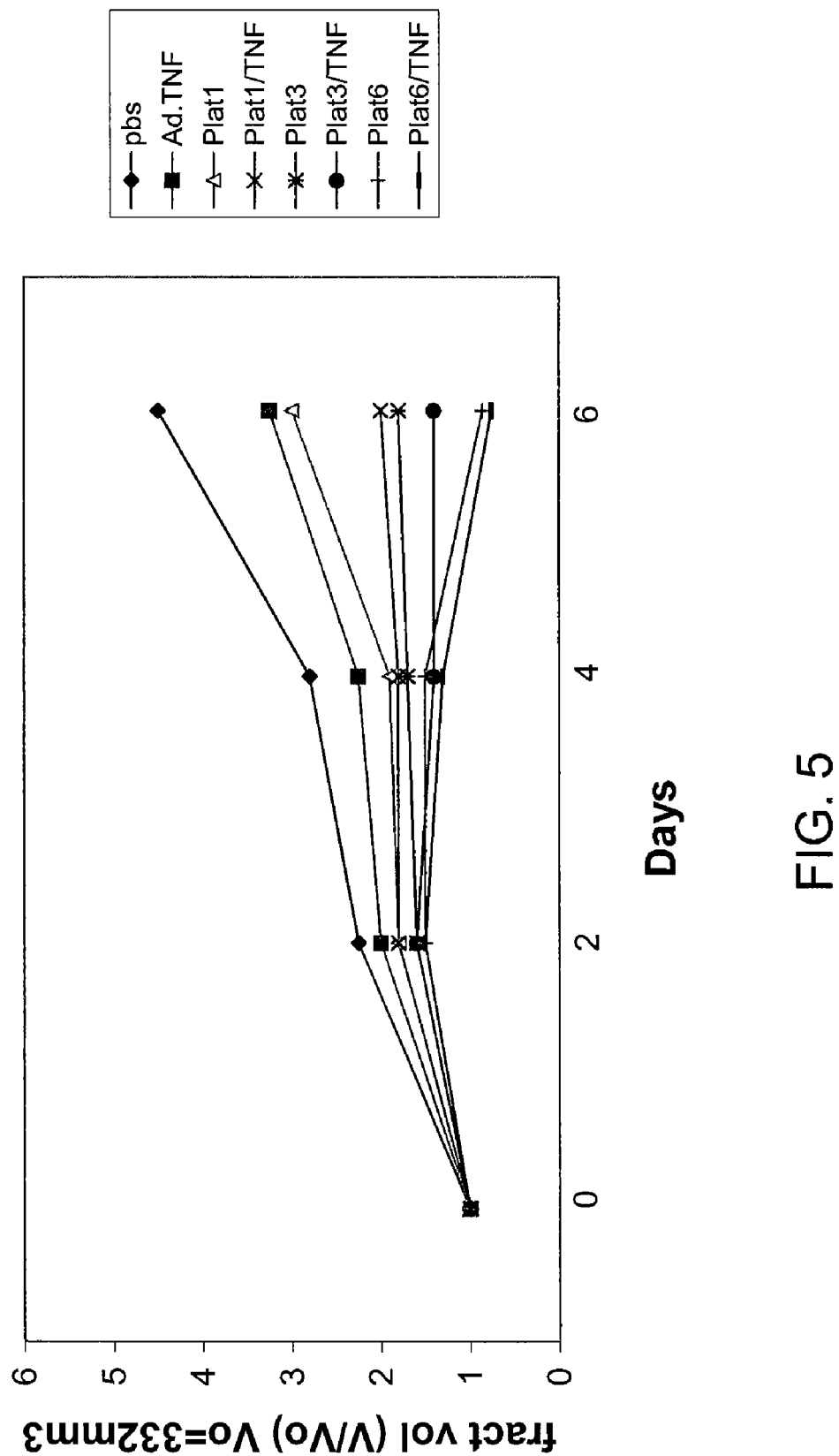
FIG. 5 is a graph comparing the response of Seg-1 cells to varying doses of cisplatin, with and without Ad.Egr.TNF.

The present inventors have previously demonstrated that a construct consisting of the 5' Egr-1 CArG elements ligated to a TNF-α cDNA express high levels of intratumoral TNF-α following radiation (IR) exposure. Tumors transduced with the chimeric Egr-TNF construct and treated with IR exhibited increased regression compared to tumors treated with either agent alone, which may be due to the intratumoral induction of TNF-α production by IR, and the cytotoxic interaction of TNF-α and IR on the tumor cells and the tumor vasculature (Weichselbaum et al., Acta Oncologica, Vol. 40:6, pp. 735-38 (2001), incorporated herein by reference). In the present invention, the inventors used various chemotherapeutic agents to induce expression of a polynucleotide encoding TNF-α under control of the chemotherapeutic agent-inducible CArG elements of the Egr-1 promoter.

Accordingly, the present invention includes methods of inducing expression of a polypeptide in a cell, inhibiting a neoplastic cell, and inhibiting or reducing growth of a tumor and/or enhancing the antiproliferative effect of chemotherapy in a subject. The methods include, but are not limited to, concomitantly contacting the cell or neoplastic cell with, or co-administering to the subject, a construct comprising a promoter operably linked to a polynucleotide encoding a therapeutic polypeptide in conjunction with a chemotherapeutic agent. In some embodiments, the methods further include co-administration to the subject of an adjunct therapy, such as, but not limited to, surgery and/or radiation.

Before any embodiments of the invention are explained in detail, it is understood that all of the compositions and methods disclosed and claimed herein can be made and executed without undue experimentation in light of the present disclosure. While the compositions and methods of this invention have been described in terms of exemplary embodiments, it will be apparent to those skilled in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. In addition, all patents and publications listed or described herein are incorporated in their entirety by reference.

Unless defined otherwise, all technical and scientific terms used herein have the same meaning as commonly understood by one of ordinary skill in the art to which this invention belongs. For purposes of clarity and as an aid in the understanding of the invention, as disclosed and claimed herein, the following definitions may be useful.

As used herein, the singular forms "a," "an," and "the" include plural referents unless the content clearly dictates otherwise. Thus, for example, reference to a composition containing "a chemotherapeutic agent" may mean that the composition includes a mixture of two or more chemotherapeutic agents. It should also be noted that the term "or" is generally employed in its sense including "and/or" unless the content clearly dictates otherwise.

As used herein, a "chemotherapeutic effective dose" of the chemotherapeutic agent refers to that amount which, when administered to a mammal, e.g., a human, for treating a cancer or neoplastic condition, is sufficient to effect treatment of the condition, i.e., the amount which is sufficient to cause an improvement in a clinically significant condition and/or symptom in a patient. In the context of the invention, an "effective amount" of a chemotherapeutic agent may also refer to the amount of agent that is sufficient to induce expression of a polypeptide from a co-administered construct. This amount may be equal to, or less than, the chemotherapeutic effective dose. Similarly, an "effective amount" of the construct refers to that amount which, when co-administered with the chemotherapeutic agent, is sufficient to result in sufficient expression of the polypeptide to result in treatment of the condition, either alone or in combination with the treatment effect of the chemotherapeutic agent.

As used herein, the term "co-administration" or "co-administering" refers to the administration of one component of the method, e.g., a construct comprising an Egr-1 promoter operably linked to a polynucleotide encoding a polypeptide, with another component, e.g., a chemotherapeutic agent, concurrently, (i.e., simultaneously in time), or sequentially, (i.e., administration of one component, followed by administration of the other component). That is, after administration of one component, the second component can be administered substantially immediately after the first component, or the second component can be administered an effective time period after the first component, the effective time period being the amount of time given for realization of benefit from the co-administration of the components. One would generally ensure that a significant period of time did not expire between the time of delivery of each component, such that the chemotherapeutic agent would be present in an amount capable of inducing expression of the therapeutic polypeptide.

Similarly, as used herein, "concomitantly" refers to performing one step of the method, i.e., contacting a cell with a construct comprising an Egr-1 promoter operably linked to polynucleotide encoding a polypeptide, at the same time, or a reasonable amount of time before and/or after, performing a second step of the method, i.e., contacting the cell with a chemotherapeutic agent. Again, such combination methods may involve contacting the cells with the construct before, during and/or after contacting the cells with the chemotherapeutic agent. Such combination therapy also can embrace contacting the cells with the construct and chemotherapy as described above in further combination with other biologically active agents or modalities such as, but not limited to, another chemotherapeutic agent, ionizing radiation and/or surgery.

As used herein, "patient" and/or "subject" refers to a mammal, more suitably a human, in need of treatment for a neoplastic disease. For purposes of study, a subject may also be an animal model, such as, e.g., a mouse.

As used herein, "treating" or "treatment" of a cancer, tumor or neoplastic condition in a subject includes one or more of: (1) inhibiting a tumor, i.e., arresting its development, (2) inhibiting or reducing growth of a tumor in a subject, i.e., arresting or preventing metastases, (3) enhancing the antiproliferative effect of chemotherapy and/or gene therapy in a subject, i.e., improving the subject's response to a treatment regime.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification.

The present invention includes methods for inducing expression of a polypeptide in a cell. The methods include, but are not limited to, concomitantly contacting the cell with a construct comprising an Egr-1 promoter operably linked to a polynucleotide encoding the polypeptide and at least one chemotherapeutic agent, wherein the chemotherapeutic agent induces expression of the polypeptide. In some embodiments, the methods further include further contacting the cell with an adjunct therapy, such as, but not limited to, radiation.

The term "construct" is used herein to refer to a polynucleotide which includes, but is not limited to, an inducible promoter operably linked to a polynucleotide encoding a therapeutic polypeptide, wherein expression of the polynucleotide encoding the polypeptide is under the control of the promoter. According to the present invention, the construct contains sufficient portions of the Egr-1 promoter to confer chemical inducibility. In some embodiments, constructs may include, but are not limited to, plasmids, cosmids, viruses (bacteriophage, animal viruses, and plant viruses) and artificial chromosomes (e.g., YACs). In a particularly suitable embodiment, constructs of the invention are delivered to the cells and/or tumor via adenoviral vectors, although other viral vectors are specifically contemplated. One of skill in the art would be well equipped to create a construct through standard molecular and/or recombinant techniques.

In the context of the invention, an "Egr-1 promoter" refers to the 5' regulatory sequences of the native promoter that are capable of controlling the chemotherapeutic agent-induced transcription of downstream polynucleotide sequences operably linked thereto. The native Egr-1 promoter has a complex structure which has been previously analyzed in the context of radiation- and $H_2O_2$-induced gene expression. It contains multiple ETS binding sites, three of which exist as parts of two serum response elements (SREs), SREI and SREII. The SREs, also known as CArG motifs, are cis-elements that regulate the expression of many growth factor responsive genes. There are a total of six SRE's, each comprising the consensus CC(A+T-rich)6GG sequence. In some embodiments, the construct comprises the entire Egr-1 promoter, including the CArG elements of the native Egr-1 gene. In other embodiments, the construct comprises the six CArG elements of the native Egr-1 promoter. In yet other embodiments, the construct comprises less than all of the six CArG element and may include as few as one CArG element.

As used herein, "operably linked" or "operably connected" refers to a functional linkage between a regulatory sequence (such as a promoter or array of transcription factor binding sites) and a second nucleic acid sequence, wherein the regulatory sequence directs transcription of the nucleic acid corresponding to the second sequence. For instance, a promoter or enhancer is operably linked to a coding sequence if it affects the transcription of the coding sequence.

Suitable polynucleotides for use in the constructs of the invention may include, but are not limited to those encoding polypeptides exhibiting therapeutic effects on neoplastic cells. The polypeptide may be a tumor suppressor, an inducer of apoptosis, an enzyme, a toxin, a cytokine, or any other protein with antitumor activity. Examples of tumor suppressors include Rb, p16, p53, PTEN, MDA7 or BRCA1 or BRCA2. Examples of inducers of apoptosis include Bax, Bad, Bik, AdE1B, Bim, Bcl-$X_s$, Bak, TRAIL, Harakiri or Bid. Examples of suitable enzymes include thymidine kinase, cytosine deaminase, or hypoxanthine guanine phosphoribosyl transferase. Examples of toxins include pseudomonas exotoxin, diptheria toxin, cholera toxin, pertussis toxin A subunit, enterotoxin A, or ricin A chain. Other polypeptides which exhibit antineoplastic effects include interleukins (IL) and cytokines, β-interferon, α-interferon, γ-interferon, angiostatin, thrombospondin, endostatin, METH-1, METH-2, GM-CSF, G-CSF, M-CSF and tumor necrosis factors (TNF) such as TNF-α and TNF-β. One of ordinary skill in the art will recognize that the invention is not limited by any particular polypeptide of interest, such as those disclosed above, as long as the polypeptide has an anti-neoplastic effect.

One particularly suitable therapeutic polypeptide is TNF-α. TNF-α is a cytokine secreted by macrophages and other hematopoetic cells that has antitumor activity in animal studies. TNF-α is cytotoxic for many malignant and/or neoplastic cells and also plays an important role in the defense against viral, bacterial and parasitic infections and in autoimmune responses. TNF-α can have a direct toxic effect on neoplastic cells, as well as cytotoxic and thrombotic effects on the tumor vasculature, and has been reported to be a successful therapeutic strategy for various sarcomas and melanomas. TNF-α has the ability to sensitize tumor cells to chemotherapy, exert potent anti-angiogenic effects on tumor microvasculature and increase vascular permeability which can potentially enhance the therapeutic effect of the chemotherapeutic agent(s).

Suitable in vitro and in vivo methods for administration of the construct may include, but are not limited to, any method by which a polynucleotide (e.g., DNA) can be introduced into an organelle, a cell, a tissue or an organism, as described herein, or as would be known to one of ordinary skill in the art. In vitro methods include, but are not limited to, direct delivery of polynucleotides, such as by ex vivo transfection, by injection (U.S. Pat. Nos. 5,994,624, 5,981,274, 5,945,100, 5,780,448), including microinjection, by electroporation, by calcium phosphate precipitation, by using DEAE-dextran followed by polyethylene glycol, by direct sonic loading, by liposome mediated transfection and receptor-mediated transfection, by microprojectile bombardment, by agitation with silicon carbide fibers, by PEG-mediated transformation of protoplasts, by desiccation/inhibition-mediated DNA uptake and/or any combination of such methods. Suitable in vivo methods of administering the construct to the subject may include, but are not limited to, use of viral vectors, and more suitably, adenoviral vectors.

The construct may be administered in an amount effective to cause arrest of the proliferation of the neoplastic cells and/or regression of the growth of a tumor when a chemotherapeutic agent is also administered to the subject in amount sufficient to induce expression of the polypeptide. For example, a construct comprising an Egr-1 promoter operably linked to a polynucleotide encoding TNF-α may be intratumorally administered to a mouse in an amount of $5 \times 10^9$ p.u. and to a human subject in an amount ranging from about $4 \times 10^7$ to $4 \times 10^{14}$ p.u.

Suitably, the construct may be administered in an amount effective to prevent further proliferation of the cells and/or regression of the tumor, without being overly toxic to the cell or subject. Further, the construct may be delivered to the subject in a number of doses over a period of time. For example, in one suitable embodiment the construct is delivered to the subject in about six doses over a 7 to 21 day period. In another suitable embodiment the construct is delivered to the subject in about six doses over a 7 to 70 day period. Thus, construct dosing schedules may be for a variety of time periods and/or as determined by one of ordinary skill in the art.

Chemotherapeutic agents are particularly useful in methods of transcriptional targeting wherein control of the expression of polynucleotides expressing therapeutic polypeptides is desired to treat widespread metastasis in addition to treating a solid tumor. In addition, many tumors either are or become resistant to TNF-α, radiation and/or various chemotherapeutic agents after treatment with these agents, and the addition of a second therapeutic agent can result in reversal of such resistance. For example, the combined treatment of TNF-α and cisplatin has revealed synergistic antitumor effects without any evidence of increased adverse side effects when compared with cisplatin treatment alone.

The term "chemotherapeutic agent," refers to a therapeutic compound and/or drug which may be used to, among other things, treat cancer. For example, a chemotherapeutic agent may include, but is not limited to, any agent that interferes with cell division, disrupts normal functionality of microtubules, inhibits utilization of a metabolite, substitutes nucleotide analogs into cellular DNA, or inhibits enzymes necessary for DNA replication. Chemotherapeutic agents, such as cisplatin, may also be used to activate or induce the Egr-1 promoter by mechanisms including, but not limited to, producing oxygen free-radical intermediates, creating DNA damage and/or causing cellular stress or growth cycle arrest. (See Yu, et al., Molec. Cell, Vol. 15, pp. 83-94 (2004), incorporated herein by reference). Non-DNA damaging agents (e.g., topotecan) may also induce the Egr-1 promoter by inhibiting nuclear enzymes that play an essential role in several aspects of DNA metabolism including replication, transcription, recombination and chromosome segregation. For example, topotecan is believed to induce the Egr-1 promoter by causing DNA lesions resulting from inhibition of topoisomerase I.

Induction of Egr-1 by some chemotherapeutic agents is believed to take place on a transcriptional level and induction of Egr-1 by compounds that do not cause direct DNA damage, such as resveratrol, vincristine or taxol, strongly suggests that it is not DNA damage per se that leads to Egr-1 induction. Blockage of DNA replication and/or arrest of the cell cycle may also be the physiological conditions triggering Egr-1 induction, as inhibition of DNA replication (i.e., Cytarabine ("Ara-C")) can also induce Egr-1 expression. While Egr-1 expression seems to be largely induced by the same kinds of DNA damaging agents and antimitotic drugs which are also known to trigger the induction of p53, this induction may actually have largely independent molecular mechanisms since induction of p53 is principally due to posttranslational regulatory mechanisms, while Egr-1 induction appears to be based on transcriptional activation.

Expression of Egr-1 may be induced by a variety of chemotherapeutic agents, including DNA damaging agents and/or non-DNA damaging agents. Chemotherapeutic agents function by a variety of mechanisms and include those agents disclosed in Goodman and Gilman, "The Pharmacological Basis of Therapeutics," $8^{th}$ ed., pp. 1202-63 (McGraw-Hill, Inc. 1990), incorporated herein by reference. Although DNA damaging compounds are not always classified as chemotherapeutic agents, the term "chemotherapeutic agent" as used herein encompasses DNA damaging agents, as well as other agents.

Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). In some embodiments, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m² to about 20 mg/m² for 5 days every three weeks for a total of three courses being contemplated in certain embodiments. In some embodiments, the amount of cisplatin delivered to the cell and/or subject in conjunction with the construct comprising an Egr-1 promoter operably linked to a polynucleotide encoding the therapeutic polypeptide is less than the amount that would be delivered when using cisplatin alone.

Other suitable chemotherapeutic agents include antimicrotubule agents, e.g., Paclitaxel ("Taxol") and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain embodiments, appropriate intravenous doses for an adult include about 60 mg/m$^2$ to about 75 mg/m$^2$ at about 21-day intervals or about 25 mg/m$^2$ to about 30 mg/m$^2$ on each of 2 or 3 successive days repeated at about 3 week to about 4 week intervals or about 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the invention. A nitrogen mustard may include, but is not limited to, mechlorethamine ($HN_2$), cyclophosphamide and/or ifosfamide, melphalan (L-sarcolysin), and chlorambucil. Cyclophosphamide (CYTOXAN®) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorodeoxyuridine; FudR). 5-FU may be administered to a subject in a dosage of anywhere between about 7.5 to about 1000 mg/m$^2$. Further, 5-FU dosing schedules may be for a variety of time periods, for example up to six weeks, or as determined by one of ordinary skill in the art to which this invention pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present invention for these cancers as well.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the invention can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

It is anticipated that the constructs comprising an Egr-1 promoter operably linked to a polynucleotide encoding the polypeptide used in combination with chemotherapeutic agents, e.g., anti-neoplastic agents, can give rise to a significantly enhanced cytotoxic effect on neoplastic cells and/or tumors, thus providing an increased therapeutic effect. Specifically, as a significantly increased growth-inhibitory effect is obtained with the above disclosed combinations using lower concentrations of the chemotherapeutic agents compared to the treatment regimes in which the agents are used alone, there is the potential to provide therapy wherein adverse side effects associated with the chemotherapeutic agents are considerably reduced when chemotherapeutic agents are used alone in larger doses. By reducing the incidence of adverse effects, an improvement in the quality of life of a patient undergoing treatment for cancer is contemplated. Further, lowering the incidence of adverse effects may improve patient compliance and reduce the number of hospitalizations needed for the treatment of adverse effects.

Actual dosage levels of the active ingredients in the methods of this invention may be varied so as to obtain an amount of the active ingredient which is effective to achieve the desired therapeutic response for a particular patient, composition and mode of administration, without being toxic to the patient. The selected dosage level will depend upon a variety of factors, including the activity of the chemotherapeutic agent selected, the route of administration, the time of administration, the rate of excretion of the chemotherapeutic agent, the duration of the treatment, other drugs, compounds and/or materials used in combination with the particular chemotherapeutic agent, the age, sex, weight, condition, general health and prior medical history of the patient being treated, and like factors well known in the medical arts.

It is envisioned that combining the effects of chemotherapy and the expression of the therapeutic polypeptide may enhance the antitumor effect of each of these agents if used alone (i.e., if the therapeutic polypeptide is administered directly, and not induced by the presence of the chemotherapeutic agent). A physician having ordinary skill in the art can readily determine and prescribe the effective amount of the construct and the chemotherapeutic agent required. For example, the physician could start doses of the construct and/or chemotherapy at levels lower than that required in order to achieve the desired therapeutic effect and gradually increase the dosage until the desired effect is achieved.

In addition to concomitantly administering a construct of the invention and a suitable chemotherapeutic agent, the methods of the present invention may further comprise administration of an adjunct therapy, such as radiation or surgery. As used herein, an "adjunct therapy" refers to any treatment that is used in addition to the primary treatment, i.e., delivery of the construct and chemotherapeutic agent. Suitable examples may include, but are not limited to, the use of surgical treatment or the delivery of ionizing radiation and/or an additional chemotherapeutic agent.

As is known in the art, radiation may be administered in a variety of fashions. For example, radiation may be electromagnetic or particulate in nature. Electromagnetic radiation useful in the practice of this invention includes, but is not limited to, x-rays and gamma rays. Particulate radiation useful in the practice of this invention includes, but is not limited to, electron beams, proton beams, neutron beams, alpha particles, and negative pi mesons. The radiation may be delivered using conventional radiological treatment apparatus and methods, and by intraoperative and stereotactic methods. Additional discussion regarding radiation treatments suitable for use in the practice of this invention may be found throughout Steven A. Leibel et al., *Textbook of Radiation Oncology*, W. B. Saunders Co. (1998), and more particularly in Chapters 13 and 14. Radiation may also be delivered by other methods such as, but not limited to, targeted delivery, for example by radioactive "seeds," or by systemic delivery of targeted radioactive conjugates. The amount of radiation delivered to the desired treatment volume may be variable. Radiation may suitably be administered in amount effective to cause arrest or regression of the cancer in a host, when the radiation is administered with a construct of the invention and a chemotherapeutic agent. For example, radiation is suitably administered in at least about 1 Gray (Gy) fraction at least once every other day to a treatment volume, is more suitably administered in at least about 2 Gy fractions at least once per day to a treatment volume, and even more suitably administered in at least about 2 Gy fractions at least once per day to a treatment volume for five consecutive days per week.

Surgical treatment for removal of the cancerous growth is generally a standard procedure for the treatment of tumors and cancers. The types of surgery that may be used in combination with the present invention include, but are not limited to, preventative, diagnostic or staging, curative and palliative surgery, and any other method that would be contemplated by those of skill in the art.

The present methods will be of use in the clinical treatment of neoplastic cells, abnormal growth of cells and/or hyperproliferative cells, various types of cancer and/or tumors. As used herein, the term "neoplastic" means an abnormal growth of a cell or tissue (e.g., a tumor) which may be benign or cancerous. As used herein, "abnormal growth of cells" and/or "hyperproliferative cells" are meant to refer to cell growth independent of normal regulatory mechanisms (e.g., loss of contact inhibition), including the abnormal growth of benign and malignant cells or other neoplastic diseases. As used herein, the term "tumor" includes neoplasms that are identifiable through clinical screening or diagnostic procedures including, but not limited to, palpation, biopsy, cell proliferation index, endoscopy, mammography, digital mammography, ultrasonography, computed tomography (CT), magnetic resonance imaging (MRI), positron emission tomography (PET), radiography, radionuclide evaluation, CT- or MRI-guided aspiration cytology, and imaging-guided needle biopsy, among others. Such diagnostic techniques are well known to those skilled in the art and are described in Holland, et al., *Cancer Medicine*, 4th Ed., Vol. One, Williams & Wilkins, Baltimore, Md. (1997).

"Inhibiting a neoplastic cell," as used herein, refers to inducing apoptosis, anoikis or necrosis, and/or interfering with cell division, disrupting normal functionality of microtubules, inhibiting utilization of a metabolite, substituting nucleotide analogs into cellular DNA, or inhibiting enzymes necessary for DNA replication, in the cell to which the construct and chemotherapeutic agent is delivered. The neoplastic cell may be a cancer cell, for example, a lung cancer cell, prostate cancer cell, ovarian cancer cell, testicular cancer cell, brain cancer cell, skin cancer cell, colon cancer cell, rectal cancer cell, gastric cancer cell, esophageal cancer cell, tracheal cancer cell, head & neck cancer cell, pancreatic cancer cell, liver cancer cell, breast cancer cell, ovarian cancer cell, lymphoid cancer cell, leukemia cell, cervical cancer cell, or vulvar cancer cell. Such treatment may also be particularly useful tools in the treatment of neoplastic diseases and/or cancers, for example, in treating patients with lung cancer, prostate cancer, ovarian cancer, testicular cancer, brain cancer, skin cancer, colon cancer, rectal cancer, gastric cancer, esophageal cancer, tracheal cancer, head & neck cancer, pancreatic cancer, liver cancer, breast cancer, ovarian cancer, lymphoid cancer, leukemia, cervical cancer, vulvar cancer or melanoma.

The following examples are included to demonstrate preferred embodiments of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, thus, the following examples are provided to assist in a further understanding of the invention. The particular materials and conditions employed are intended to be further illustrative of the invention and are not limiting on the reasonable scope of the appended claims.

EXAMPLES

Example 1

Experimental Methods

The following materials and methods were used in the experiments described in Examples 2-5.

Cells and cell culture. Cell lines Seg-1, a human esophageal adenocarcinoma (Dr. David Beer, Univ. of Michigan, Ann Arbor, Mich.), and DHD/K12/TRb (PROb), a rat colon adenocarcinoma established in syngeneic BD-IX rats by 1,2-dimethylhydrazine induction (Dr. Francois Martin, Univ. of Dijon, France), were maintained in Dulbecco's Modified Eagle Medium (DMEM) (GibcoBRL, Grand Island, N.Y.) supplemented with Fetal Bovine Serum (FBS, 10% v/v) (Intergen, Purchase, N.Y.), penicillin (100 IU/ml), and streptomycin (100 µg/ml) (GibcoBRL), at 37° C. and 7.5% $CO_2$.

Animals. Athymic nude mice (Frederick Cancer Research Institute, Frederick, Md.) received food and water ad libitum. Experiments were in accordance with the guidelines of the University of Chicago.

Viral vectors. The viral vectors Ad.Egr.TNF.11D and Ad.Null.3511.11D (GenVec, Gaithersburg, Md.) were stored at −80° C., and diluted to the appropriate concentration in formulation buffer.

In vitro measurement of TNF-α protein. Seg-1 and PROb cells were plated at $10^5$ cells/well in 12-well plates (Becton Dickinson, Bedford, Mass.), grown overnight, and infected with either Ad.Null.3511.11D or Ad.Egr.TNF.11D at 100 multiplicities of infection (MOI) in serum-free medium for 2-3 hours. IR treated cells in complete medium were exposed to 5 Gy using a Pantak PCM 1000 x-ray generator. Cells in the cisplatin group were exposed to 5 µM cisplatin in complete medium. Cells and supernatants were harvested by scraping at 24, 48, and 72 hours, and production of human TNF-α was quantified by ELISA (R&D Systems, Minneapolis, Minn.) following three cycles of freeze-thaw lysis. Assays were performed in triplicate. Duplicate treatment plates were used to adjust for the cytotoxicity of IR and cisplatin. Cells were harvested using versene (0.02% EDTA in HBSS) and trypsin-EDTA (0.25% trypsin, 1 mM EDTA.4Nα) (GibcoBRL) and cells were counted using the hemocytometer with trypan blue (0.4%) exclusion (GibcoBRL). Protein assays were performed to normalize for protein concentration (Bio-Rad, Hercules, Calif.).

In vitro luciferase reporter assay. The Egr-1 constructs pE425 (596 base pairs containing all CArG elements, no AP-1 sites) and pE660 (minimal Egr-1 promoter, 115 base pairs, no CArG elements) (Datta et al., 1993) were evaluated following sequence confirmation and insertion of the PCR product into the pGL3 basic firefly luciferase reporter plasmid construct (Promega, Madison, Wis.) by enzyme restriction and ligation. JM109 competent cells (Stratagene, La Jolla, Calif.) were transformed with these plasmids, endotoxin-free maxipreps (Qiagen, Valencia, Calif.) were prepared, and product confirmation was performed by PCR, sequencing, enzyme restriction, and gel electrophoresis.

Seg-1 and PROb cells were plated at $10^5$ cells/well in 12-well plates and transfected with firefly luciferase reporter plasmid constructs, pGL3 basic (promoterless, negative control), pGL3 660 (minimal Egr-1 promoter), or pGL3 425 (Egr-1 promoter containing all CArG elements) using the TransFast transfection reagent (Promega). All groups were co-transfected with the Renilla luciferase reporter plasmid construct pRL-TK (HSV thymidine kinase promoter) to normalize for transfection efficiency. 48 hrs later, cells were exposed to IR (20 Gy) or cisplatin (5 μM). Cells were harvested 6 hrs later, and luciferase activity was measured using the Dual-Luciferase reporter assay system (Promega).

In vivo measurement of TNF-α protein. Seg-1 or PROb cells ($5 \times 10^6$/0.1 ml) were injected in the right hind limb of nude mice. Tumor bearing mice were randomized to one of 4 groups: intratumoral (IT) Ad.Null.3511.11D ($2 \times 10^8$ p.u./10 μl) with intraperitoneal (IP) normal saline (NS) or cisplatin (8 mg/kg) and IT Ad.Egr.TNF.11D ($2 \times 10^8$ p.u./10 μl) with IP NS or cisplatin. IP NS or cisplatin treatments were administered after IT vector. Two consecutive IT and IP injections were given. Animals were euthanized and xenografts were harvested 48 hours following the second IP injection. Xenografts were snap frozen in liquid nitrogen, and homogenized in RIPA buffer (NaCl 150 mM, Tris 10 mM, pH 7.5, EDTA 5 mM, pH 7.5, PMSF 100 mM, Leupeptin 1 μg/ml, Aprotinin 2 μg/ml) using a Brinkman Polytron Homogenizer (Kinematica AG, Lucerne, Switzerland). Following three freeze-thaw lysis cycles, the homogenate was centrifuged at 10,000 rpm (Sorvall RC5C SS34 rotor) for 10 minutes, at 4° C. TNF-α levels in the supernatants were measured using ELISA and protein assays were performed (Bio-Rad, Hercules, Calif.).

In vivo regrowth studies. Seg-1 or PROb cells ($5 \times 10^6$/0.1 ml) were injected in the right hind limb of nude mice. Tumor bearing mice were assigned to one of 4 groups: IT Ad.Null.3511.11D ($2 \times 10^8$ p.u./10 μl) with IP NS or cisplatin (3 mg/kg) and IT Ad.Egr.TNF.11D ($2 \times 10^8$ p.u./10 μl) with IP NS or cisplatin. IP NS or cisplatin injections were given following the IT vector injection, and 4 consecutive daily IT and IP injections were given. Xenografts were measured every 2 days using calipers and tumor volume was calculated (length×width×thickness)/2. Fractional tumor volumes (V/Vo, Vo=day 0 volume) were calculated and plotted.

Statistical analysis. Statistical significance was determined using two-tail student's t-test.

Example 2

In vitro Induction of TNF-α in Human and Rat Tumor Cells Following Infection with Ad.Egr.TNF.11D and Exposure to Cisplatin TNF-α production was tested in human esophageal Seg-1 cells and rat colorectal PROb cells infected with Ad.Egr.TNF.11D or Ad.Null.3511.11D following exposure to IR or cisplatin, using an ELISA specific for human TNF-α.

Figure 6A:
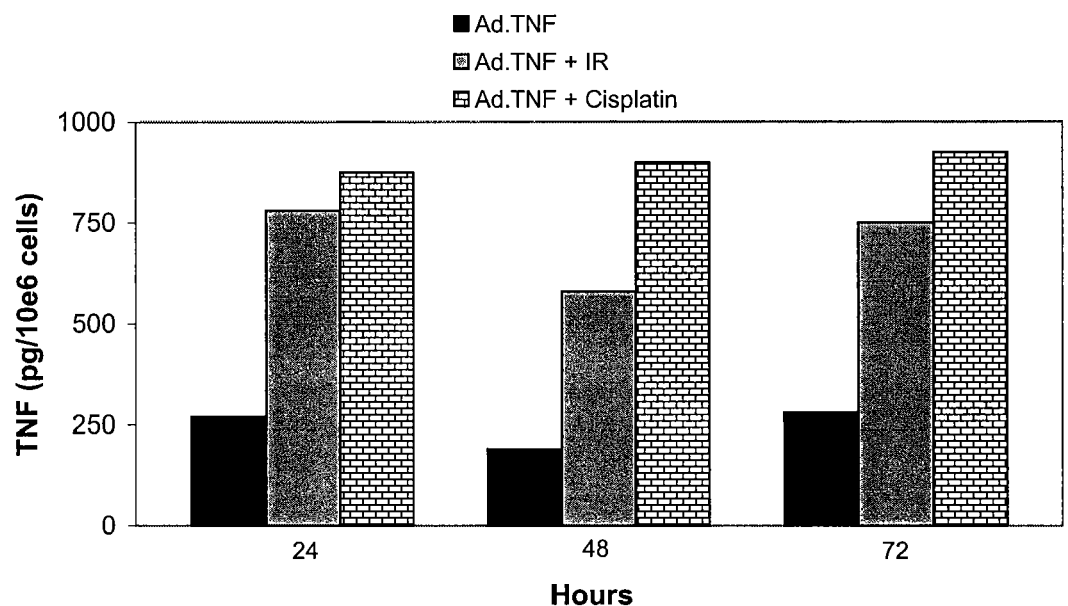
FIGS. 6A & 6B depict levels of in vitro TNF-α production by Ad.Egr.TNF-infected Seg-1 cells (6A) and PROb cells (6B) exposed to IR, cisplatin, or both, at 24, 48 and 72 hours.

No TNF-α protein was detectable in Seg-1 pellets or supernatants from cultures infected with Ad.Null.3511.11D and treated with IR or cisplatin, moderate levels were detected in cells infected with Ad.Egr.TNF.11D alone (269.3±1.9, 167.8±8.4, 260.6±14.9; P<0.001), and significant levels were detected in cells infected with Ad.Egr.TNF.11D and exposed to 5 Gy IR (768.8±32.6, 593.0±27.6, 746.0±18.5), and to 5 μM cisplatin (885.3±28.7, 892.6±21.3, 901.7±21.7; P<0.001), at 24, 48 and 72 hours, respectively. Combined treatment of Ad.Egr.TNF.11D and IR resulted in a 2.9, 3.5 and 2.9-fold increase, and Ad.Egr.TNF.11D and cisplatin resulted in a 3.3, 5.3 and 3.5-fold increase, in TNF production. See FIG. 6A.

Figure 6B:
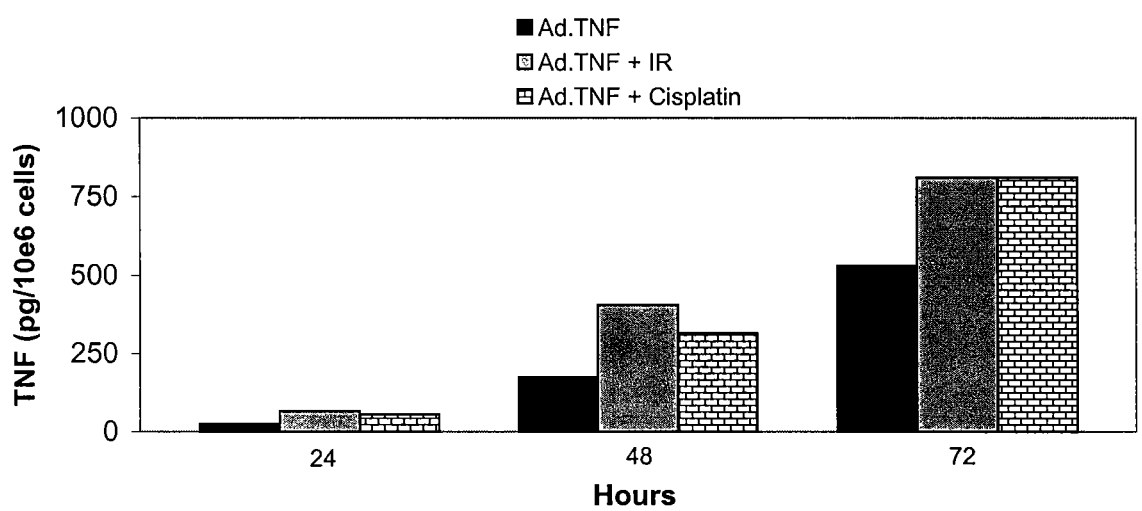

Similarly, no TNF-α protein was detectable in PROb cell pellets or supernatants from cultures infected with Ad.Null.3511.11D and treated with IR or cisplatin, moderate levels were detected in cells infected with Ad.Egr.TNF alone (17.9±1.7, 169.7±5.2, 522.5±11.3), and significant levels were detected in cells infected with Ad.Egr.TNF.11D and exposed to 5 Gy IR (55.1±4.6, 440.5±7.0, 812.7±8.9), and to 5 μM cisplatin (52.4±0.6, 318.6±30.6, 812.2±11.0) at 24, 48 and 72 hrs, respectively (P<0.001). Combined treatment with Ad.Egr.TNF.11D and IR resulted in a 3.1, 2.6 and 1.6-fold increase, and Ad.Egr.TNF.11D and cisplatin resulted in a 2.9, 1.9 and 1.6-fold increase, in TNF production. See FIG. 6B.

These results indicate that a cisplatin inducible genetic construct enhances the effects of cisplatin, in this case by TNF-α, and that cisplatin and TNF-α have different mechanisms of cell killing and therefore, cells resistant to cisplatin may be sensitive to TNF-α and vice versa. Thus, the cisplatin/Ad.Egr.TNF.11D strategy may be an effective therapy for localized tumors not effectively treated with radiotherapy or surgery alone.

Example 3

CArG Elements of the Egr-1 Promoter Mediate Induction of TNF-α by Cisplatin

Seg-1 and PROb cells were co-transfected with the firefly luciferase reporter plasmid constructs pGL3 basic (negative control), pGL3 660 (minimal Egr-1 promoter, no CArG elements), or pGL3 425 (all CArG elements, no AP-1 sites), and the Renilla luciferase reporter plasmid construct pRL-TK.

Figure 7A:
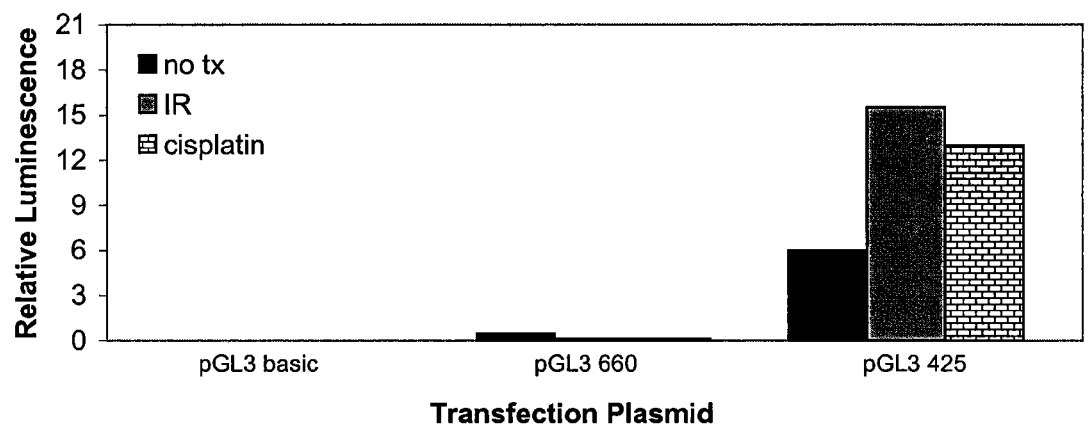
FIGS. 7A & 7B depict in vitro responses to radio- and chemo-induction of luciferase reporter constructs comprising luciferase reporter plasmid constructs pGL3, pGL3 660 or pGL3 425 in Seg-1 cells (7A) and PROb cells (7B).
Figure 7B:
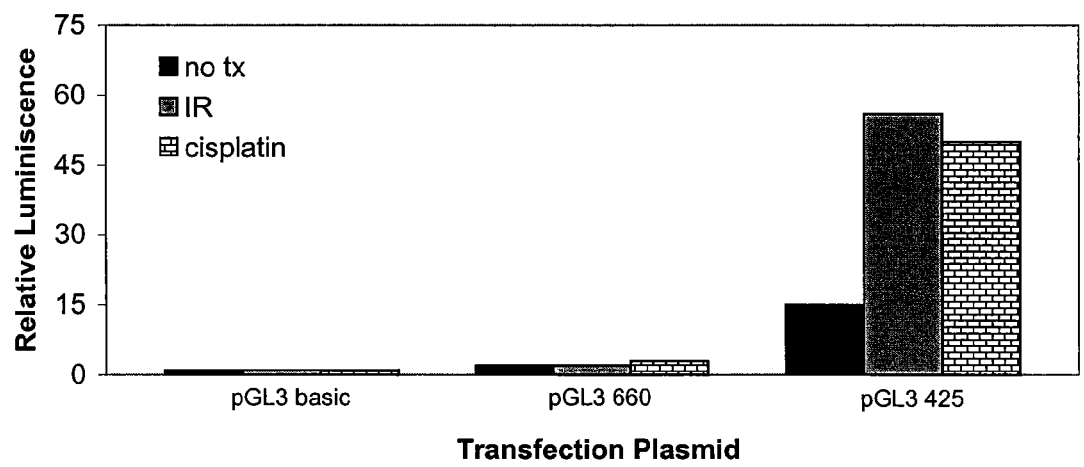

Luciferase activity (LA) was minimal in Seg-1 cells transfected with the pGL3 basic (0.01-0.02) and the pGL3 660 (0.10-0.18) plasmid constructs, while cells transfected with the pGL3 425 plasmid construct exhibited a 2.4-fold increase in relative LA (15.07) following exposure to 20 Gy IR compared to untreated control (6.37) and a 2.0-fold increase in LA (2.89) following exposure to 50 μM cisplatin compared with untreated control. See FIG. 7A. Similarly, LA was minimal in PROb cells transfected with the pGL3 basic (0.21-0.30) and the pGL3 660 (0.76-1.84) plasmid constructs, while cells transfected with the pGL3 425 plasmid construct exhibited a 4.2-fold increase in LA (57.75) following exposure to 20 Gy IR compared to untreated control (13.69), and a 3.6-fold increase in LA (49.40) following exposure to 50 μM cisplatin compared with untreated control. See FIG. 7B.

These data demonstrate that CArG elements of the Egr-1 promoter are inducible by cisplatin and mediate the transcriptional activation of the chimeric Egr-1.TNF-α gene.

Example 4

Induction of TNF-α in Human and Rat Tumor Xenografts Following Treatment with Ad.Egr.TNF.11D and Cisplatin Xenografts of Seg-1 or PROb cells growing the hind limbs of athymic nude mice were injected IT with Ad.Nul.3511.11D or Ad.Egr.TNF.11D. Tumor bearing mice were injected IP with either NS or cisplatin (3 mg/kg). TNF-α concentration in tumor homogenates was quantified using ELISA.

Figure 8A:
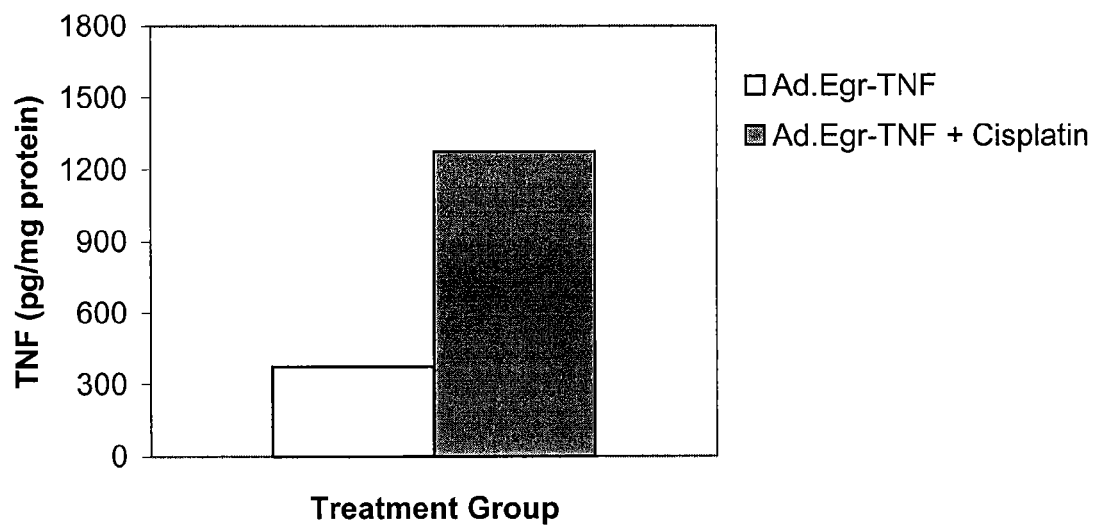
FIGS. 8A & 8B depict in vivo levels of intratumoral TNF-α produced by Seg-1 cells (8A) and PROb xenographs (8B) following treatment with Ad.Egr.TNF, with and without cisplatin.
Figure 8B:
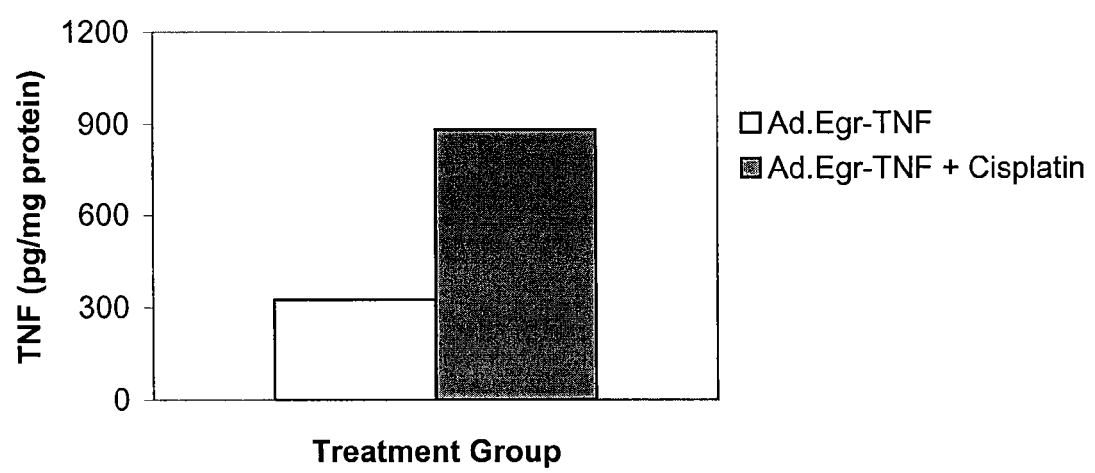

No TNF-α protein was detected in Seg-1 tumor homogenates following injection of the Ad.Null.3511.11D vector and systemic treatment with either NS or cisplatin, a moderate amount was detected with the vector alone (366.5±52.6 pg/mg), and a significant increase (3.5-fold) in IT TNF-α protein was observed following combined treatment with Ad.Egr.TNF.11D and cisplatin (1294.0±438.5 pg/mg). See FIG. 8A. Likewise, no TNF-α protein was detected in PROb tumor homogenates following injection of Ad.Null.3511.11D and systemic treatment with either NS or cisplatin, a moderate amount was detected with treatment of the vector alone (321.4±27.7 pg/mg), and a significant increase (2.7-fold) in IT TNF-α protein was observed following combined treatment with Ad.Egr.TNF.11D and cisplatin (878.6±61.9 pg/mg). See FIG. 8B.

These findings demonstrate in vivo induction of TNF-α protein by cisplatin and verify that the TNF-α protein is a product of the Ad.Egr.TNF.11D vector rather than the tumor tissue.

Example 5

Figure 9A:
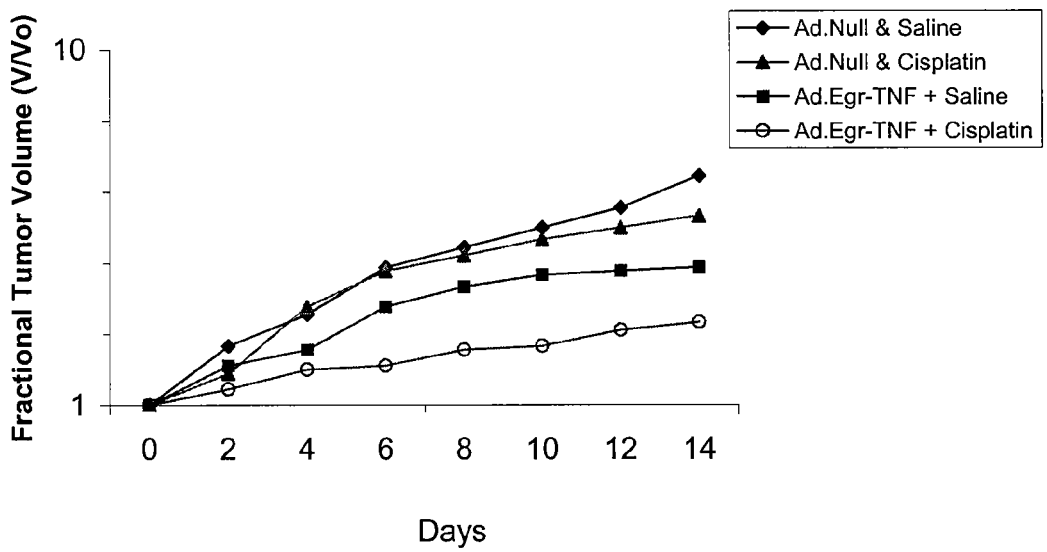
FIGS. 9A & 9B depict in vivo regrowth studies by measuring the volume of xenografts injected with a null construct (Ad.Null) and Ad.Egr.TNF, with or without cisplatin.
Figure 9B:
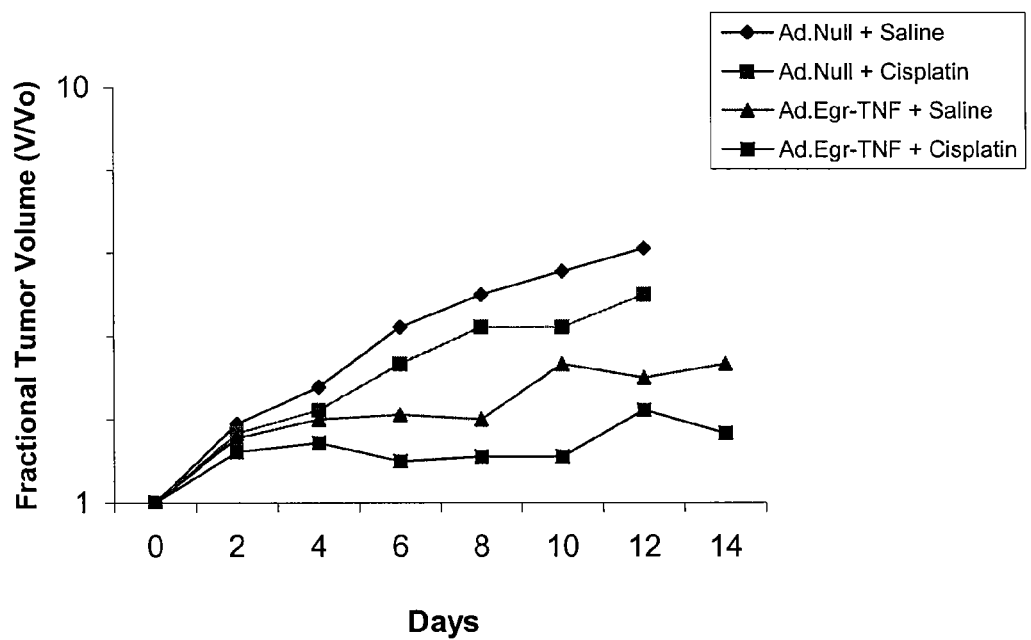

Cisplatin Inducible Ad.Egr.TNF.11D Enhances Treatment of Human and Rat Xenografts Potential antitumor effects of chemo-inducible Ad.Egr.TNF.11D and cisplatin were examined in Seg-1 and PROb xenografts In the Seg-1 studies, mean tumor volume on day 0 (initiation of treatment) was 381.3±10.8 mm$^3$ (n=48, 12 mice/tmt. gp.). Xenografts were injected IT with either Ad.Null.3511.11D or Ad.Egr.TNF.11D, and mice were injected IP with either NS or cisplatin. Control tumors exhibited a 2-fold and 4.7, and vector-only tumors exhibited a 2-fold and 3.8-fold, increase in tumor volume at days 4 and 14, respectively, while moderate tumor regression was observed with the null vector and cisplatin treatment and significant tumor regression was observed in tumors treated with Ad.Egr.TNF.11D and cisplatin. See FIG. 9A. In the PROb studies, mean tumor volume on day 0 was 244.2±6.2 mm$^3$ (n=40, 10 mice/tmt. gp.). Control tumors exhibited a 2-fold and 4.4-fold increase, and vector-only tumors experienced a 1.6-fold and 3.6-fold increase, in tumor volume at day 4 and 14, respectively, while moderate tumor regression was observed with the null vector and cisplatin treatment and significant tumor regression was observed in the tumors receiving combined vector and cisplatin treatment. See FIG. 9B.

Taken together, these data support an antitumor interaction between cisplatin and Ad.Egr.TNF.11D in xenografts of human and rodent origin, which is consistent with TNF-α induction by cisplatin observed in the in vitro and in vivo experiments. No additional toxicity was observed following combined treatment with cisplatin and Ad.Egr.TNF.11D.

Example 6

Experimental Methods

The following materials and methods were used in the experiments described in Examples 7-13.

Cells and cell culture. PC-3 cells, a human prostate adenocarcinoma cell line obtained from the ATCC, and DHD/K12/TRb (PROb), a rat colon adenocarcinoma established in syngeneic BD-IX rats by 1,2-dimethylhydrazine induction (obtained from Francois Martin, Univ. of Dijon, France), were used. The PC-3 and PROb cells were maintained in DMEM-F12 (Invitrogen Life Technologies, Carlsbad, Calif.) supplemented with FBS (10% vol/vol) (Intergen, Purchase, N.Y.), penicillin (100 IU/ml), and streptomycin (100 μg/ml) (Invitrogen Life Technologies) at 37° C. with 7.5% $CO_2$.

Chemical reagents. Reagents used include N-Acetylcysteine (NAC) (Roxane Laboratories, Inc., Columbus, Ohio), cisplatin/fluorouracil (Am. Pharm. Partners, Schaumburg, Ill.), doxorubicin (Ben Venue Labs., Bedford, Ohio), gemcitabine (Eli Lilly, Indianapolis, Ind.), paclitaxel (F. H. Faulding, Mulgrave Victoria, Australia), and cyclophosphamide (Bristol-Myers Squibb, Princeton, N.J.).

Animals. The in vivo experiments were conducted using female athymic nude mice (Frederick Cancer Research Institute, Frederick, Md.).

Xenografts. PC-3 and PROb xenografts were established by injecting $10^7$ cells/100 μl PBS, and $5 \times 10^6$ cells/100 μl PBS, respectively, into the right hind limb of 6-week old female athymic nude mice. Experiments were conducted 2-3 weeks after injection, when tumors reached an average size of 200-300 mm$^3$, in accordance with the guidelines of the Institutional Animal Care and Use Committee of the University of Chicago.

Viral vectors. Ad.Egr.TNF.11D (GenVec Inc., Gaithersburg, Md.), a replication-deficient adenoviral vector (E1-, partially E3-, E4-deleted) containing the human TNF-α gene under the control of the radiation-inducible promoter Egr-1, was stored at −80° C. and was diluted in formulation buffer (GenVec) to the appropriate concentration. See FIG. 1

In vitro measurement of TNF-α protein. PC-3 and PROb cells were plated in 96-well plates, grown overnight, and infected with Ad.Egr.TNF at 100 multiplicities of infection, incubated for three hrs, and were then treated with cisplatin (250 μM), doxorubicin (3 μM), 5-FU (20 mM) or paclitaxel (14 μM). Supernatants were harvested 24 hrs later and human TNF-α production was quantified by ELISA. Experiments were performed in quintuplicate.

In vivo measurement of TNF-α protein. PC-3 ($1 \times 10^7$ cells) or PROb cells ($5 \times 10^6$) in 100 μl PBS were injected subcutaneously into the right hind limb of nude mice. Tumor-bearing mice received IT Ad.Egr.TNF ($5 \times 10^9$ p.u. in 10 μl) with 250 μl of complete media with NS or a chemotherapeutic agent, including cisplatin (9 mg/kg), cyclophosphamide (160 mg/kg), doxorubicin (15 mg/kg), 5-fluorouracil (100 mg/kg) and gemcitabine (500 mg/kg). Each mouse IP injections were administered 20 hrs after transfection, and two consecutive IT and IP injections were given. Animals were euthanized, and xenografts were harvested 48 hrs after the second IP injection. Xenografts were snap-frozen in liquid nitrogen and homogenized in RIPA buffer (150 mM NaCl, 10 mM Tris at pH 7.5, 5 mM EDTA at pH 7.5, 100 mM PMSF, 1 μg/ml leupeptin and 2 μg/ml aprotinin). After three freeze-thaw lysis cycles, the homogenate was centrifuged for 10 minutes at 4° C. TNF-α levels in the supernatants were measured as described above.

Efficacy study. On day 0, tumor-bearing mice were volume-matched and assigned to one of four groups: NS as control, Ad.Egr.TNF only ($5 \times 10^9$ p.u. in 10 μl IP on days 0 and 3), doxorubicin (2 mg/kg IP daily for 10 days), or a combined treatment of Ad.Egr.TNF and doxorubicin. Xenografts volumes (length×width×thickness/2) were measured using calipers twice weekly. Fractional tumor volumes (V/Vo where Vo=volume on day 0) were calculated and plotted. Day 0 is the day of randomization and the first day of treatment.

Chemo-sensitivity of PC-3 and PROb cells as determined by MTS assay. PC-3 and PROb cells were plated at a density of $10^5$ cells/100 μl medium in 96-well tissue culture plates and incubated overnight. The medium was removed, and cells were infected with Ad.Egr.TNF.11D in serum-free medium at 0 and 100 multiplicities of infection (MOI) for 3 hrs. After incubation, 200 μl of complete media, with or without chemotherapeutic agents, was added. Chemotherapeutic agents used were at final concentrations of cisplatin at 46 and 460 μM, doxorubicin at 3 and 300 μM, 5-fluorouracil at 2 and 200 mM and paclitaxel at 1.4 and 140 μM. Media was removed 24 hrs later and each well was rinsed with 200 μl of complete media (CM) and aspirated. 100 μl of CM was then added with 20 μl of CellTiter 96® Aqueous One Solution Cell Proliferation Assay solution (Promega, Madison, Wis.), and the cells were allowed to incubate for 1 hr. Absorbance was measured at 490-650 nm.

Chemo-inducibility of Ad.Egr-TNF.11D in vitro. PC-3 and PROb cells were plated, infected with Ad.Egr.TNF, and incubated as discussed above. After incubation, 200 μl of CM, with or without chemotherapeutic agents, including cisplatin (250 μM), doxorubicin (3 μM), 5-fluorouracil (100 mM), gemcitabine (3 mM) and paclitaxel (14 μM) were added. Conditioned medium was harvested 24 hrs. later, and TNF-α concentration was measured (Quantikine Human TNF-α ELISA kit, R & D Systems, Minneapolis, Minn.).

Chemo-inducibility of Ad.Egr-TNF.11D in vivo. PC-3 and PROb xenografts were injected IT with $5 \times 10^9$ p.u. of Ad.Egr.TNF.11D on days 0 and 1. Saline or chemotherapeutic agents administered IP on days 1 and 2, including 9 mg/kg cisplatin, 160 mg/kg cyclophosphamide, 15 mg/kg doxorubicin, 100 mg/kg 5-FU and 500 mg/kg gemcitabine. Animals were euthanized, and xenografts were harvested 24 hrs after the second IP injection. Xenografts were snap-frozen in liquid nitrogen and homogenized in RIPA buffer (150 mM NaCl, 10 mM Tris pH 7.5, 5 mM EDTA pH 7.5, 100 mM PMSF, 1 pg/ml leupeptin and 2 μg/ml aprotinin) using a Brinkman Polytron homogenizer (Kinematica AG, Lucerne, Switzerland). After three freeze-thaw lysis cycles, the homogenate was centrifuged at 7800×g in a Sorvall RC-5C SS34 rotor (Kendro Laboratory Products, Newtown, Conn.) for 10 min at 4° C. TNF-α levels in the supernatants were measured by ELISA as described above.

N-acetyl cysteine effects on TNF-α production in vitro. PC-3 and PROb cells were plated and infected with Ad.Egr-TNF.11D as described above. PC-3 and PROb cells were treated with NAC at 0 mM, 10 mM, 20 mM and 30 mM, followed immediately by the addition of 100 mM 5-FU. Conditioned medium was collected after 24 hrs of incubation at 37° C. and stored at −20° C. TNF-α levels were determined by ELISA.

PC-3 and PROb cells were plated and infected with Ad.Egr-TNF.11D as above. Prior to the addition of chemotherapeutic agents (cisplatin, doxorubicin, 5-FU, gemcitabine and paclitaxel), 20 mM NAC in 0.1 ml complete medium was added to each well. Conditioned medium was collected after 24 hrs. of incubation at 37° C., and stored at −20° C. TNF-α levels were determined by ELISA.

Xenograft regrowth studies. Treatment was initiated on day 0 at which time mice were assigned to one of 4 treatment groups: control, doxorubicin, Ad.Egr-TNF.11D, and combination of Ad.Egr-TNF.11D and doxorubicin. On days 0 and 3, mice received IT injection of 10 μl of either $5 \times 10^9$ p.u. Ad.Egr-TNF.11D, or 10 μl of viral formulation buffer. IP injections of doxorubicin or NS (2 mg/kg) were administered daily from days 0 through 8. Xenografts were measured twice weekly and tumor volume was calculated according to the formula (length×width×thickness)/2. Fractional tumor volumes (V/V$_0$ where V$_0$=volume on day 0) were calculated and plotted.

Analysis of microvessel density. Two or three xenografts from each treatment group in the PC-3 regrowth study above were collected and fixed in 10% neutral buffered formalin, embedded in paraffin, cut in 5 μm slices, mounted, baked, cleared in xylene, and rehydrated in decreasing alcohol concentrations (100%-70%) and distilled water. Sections were microwaved in 10 mM citrate buffer at pH 6.0 for 18 min, washed and soaked in 1% hydrogen peroxide/methanol for 20 min prior to blocking with avidin-biotin (Vector Laboratories, Burlingame, Calif.) for 15 min. Slides were incubated with biotin (15 min), washed and blocked with serum-free DAKO protein (DAKO, Carpinteria, Calif.) for 10 min prior to incubation with a 1:50 dilution of goat anti-mouse CD31 antibody (Santa Cruz, Santa Cruz, Calif.) for 60 min at RT. CD-31 staining was visualized on tissue sections following incubation with DAKO biotinylated anti-goat secondary antibody for 30 min and DAB reagent (Vector) for 60 sec. Sections were counterstained with Gill 3 hematoxylin and dehydrated in ethanol (95%-100%) and xylene prior to mounting. All slides were read by an investigator blinded to the treatment groups. Positively stained vessels were counted in 5-10 high power fields (×400) per slide using light microscopy. Blood vessels were identified by endothelial cell staining and by endothelial cells surrounding intraluminal erythrocytes.

Statistical analysis. Statistical significance was determined by one-way analysis of variance (ANOVA). Differences between treatment groups were determined by either student's t test or Mann-Whitney rank sum test.

Example 7

Preliminary Results

Figure 10:
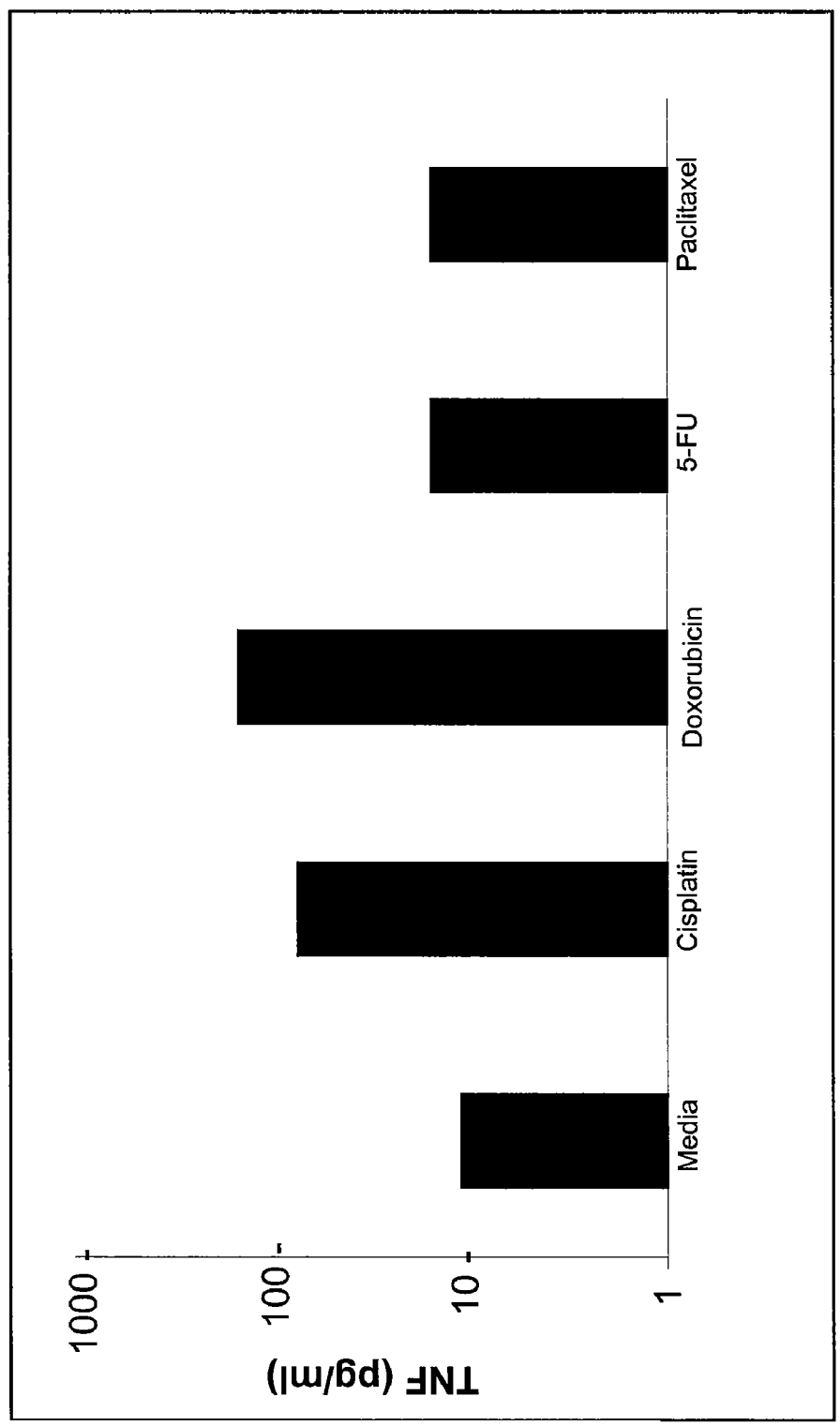
FIG. 10 depicts levels of TNF-α produced by PC-3 cells transduced in vitro with Ad.Egr.TNF.
Figure 11:
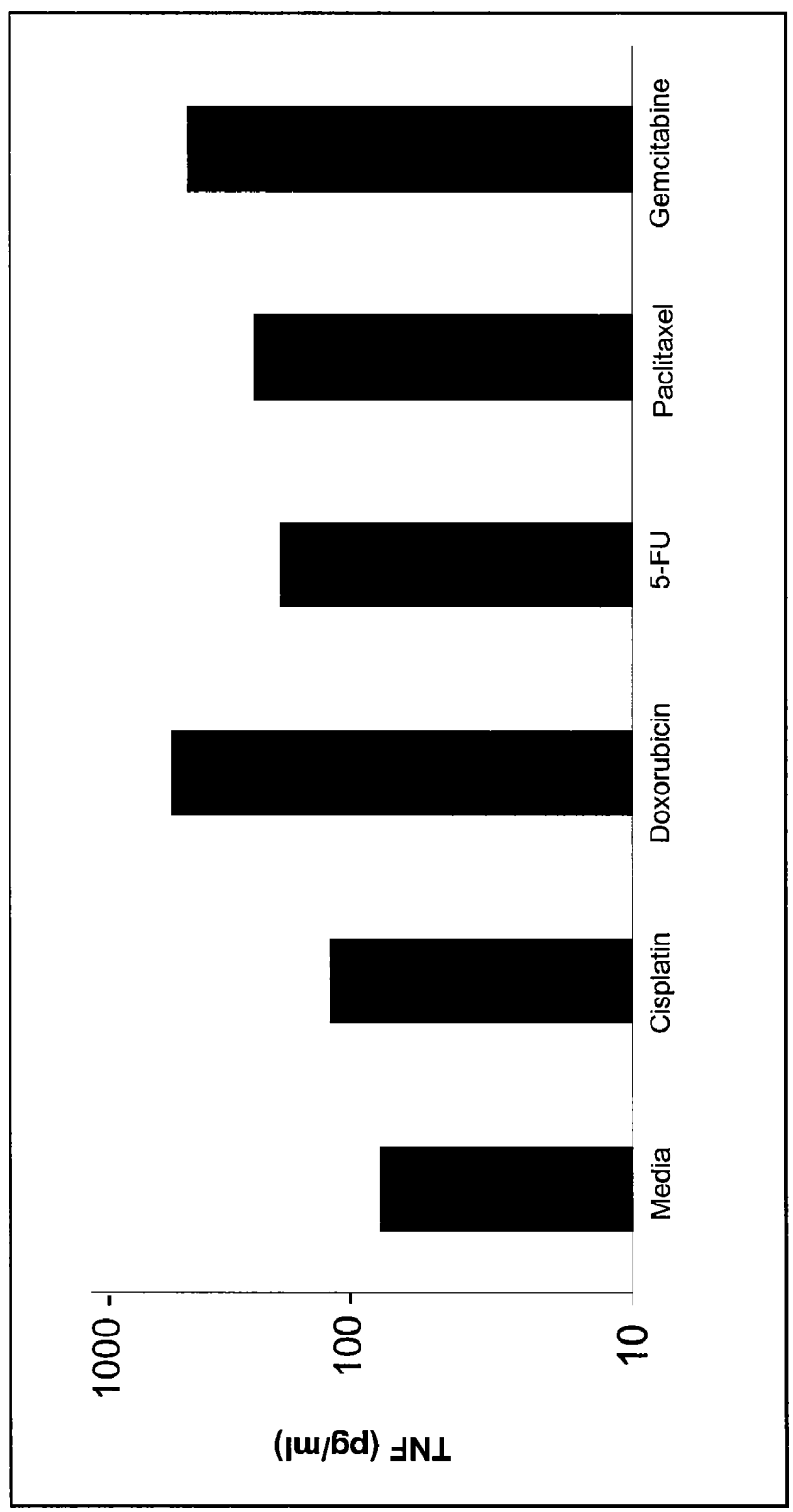
FIG. 11 depicts levels of TNF-α produced by PROb cells transduced in vitro with Ad.Egr.TNF.

In vitro study. Vector treated PC-3 cells showed increased TNF levels with the addition of cisplatin (6.5-fold), doxorubicin (14.5-fold), 5-FU (1.8-fold) and paclitaxel (1.8-fold). See FIG. 10. PROb cells treated with Ad.TNF showed increased TNF levels with the addition of cisplatin (1.6-fold), doxorubicin (7.3-fold), 5-FU (2.3-fold) and paclitaxel (3.0-fold) and gemcitabine (5.4-fold). See FIG. 11.

Figure 12:
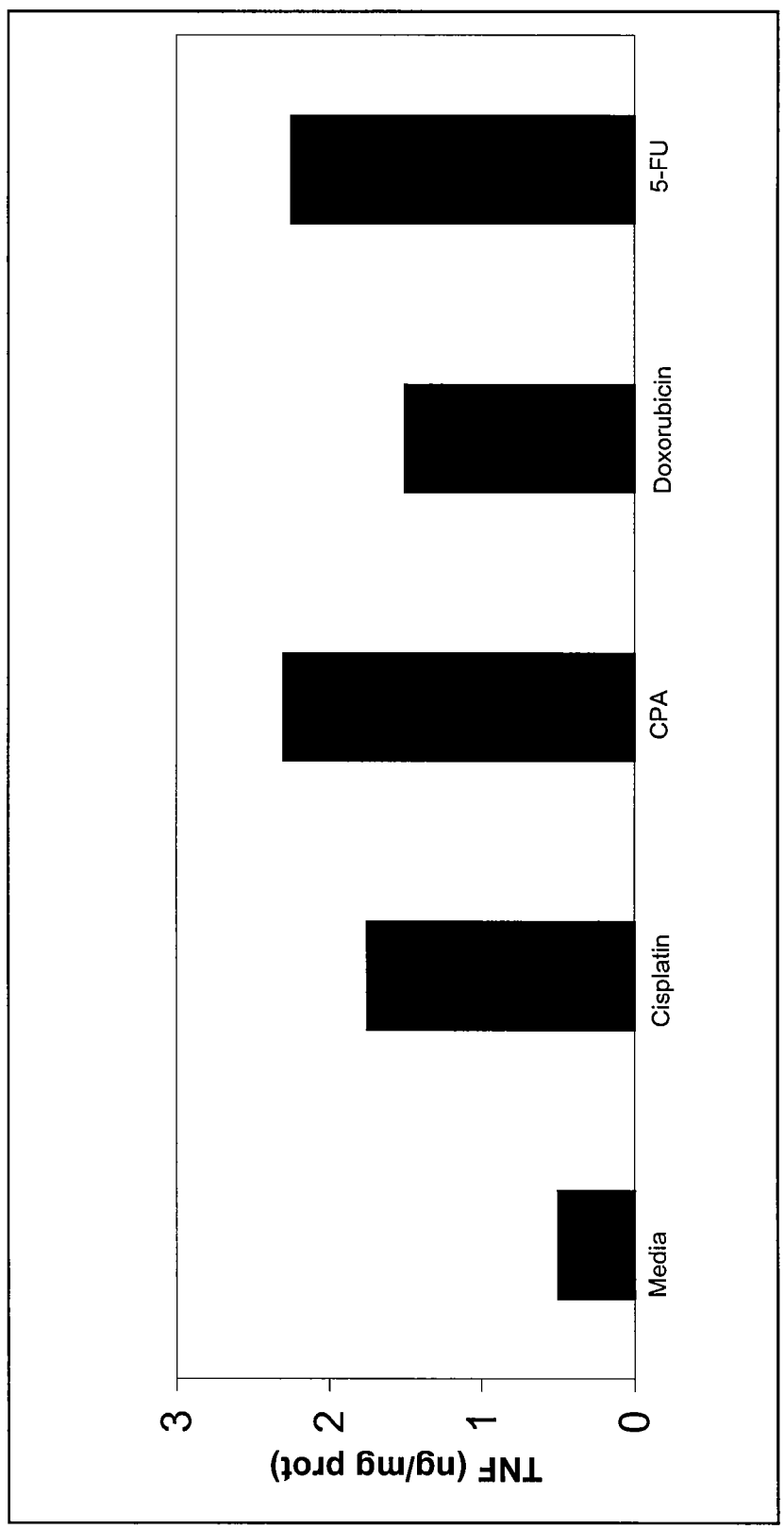
FIG. 12 depicts levels of TNF-α produced in PC-3 xenografts after delivery of Ad. Egr.TNF.
Figure 13:
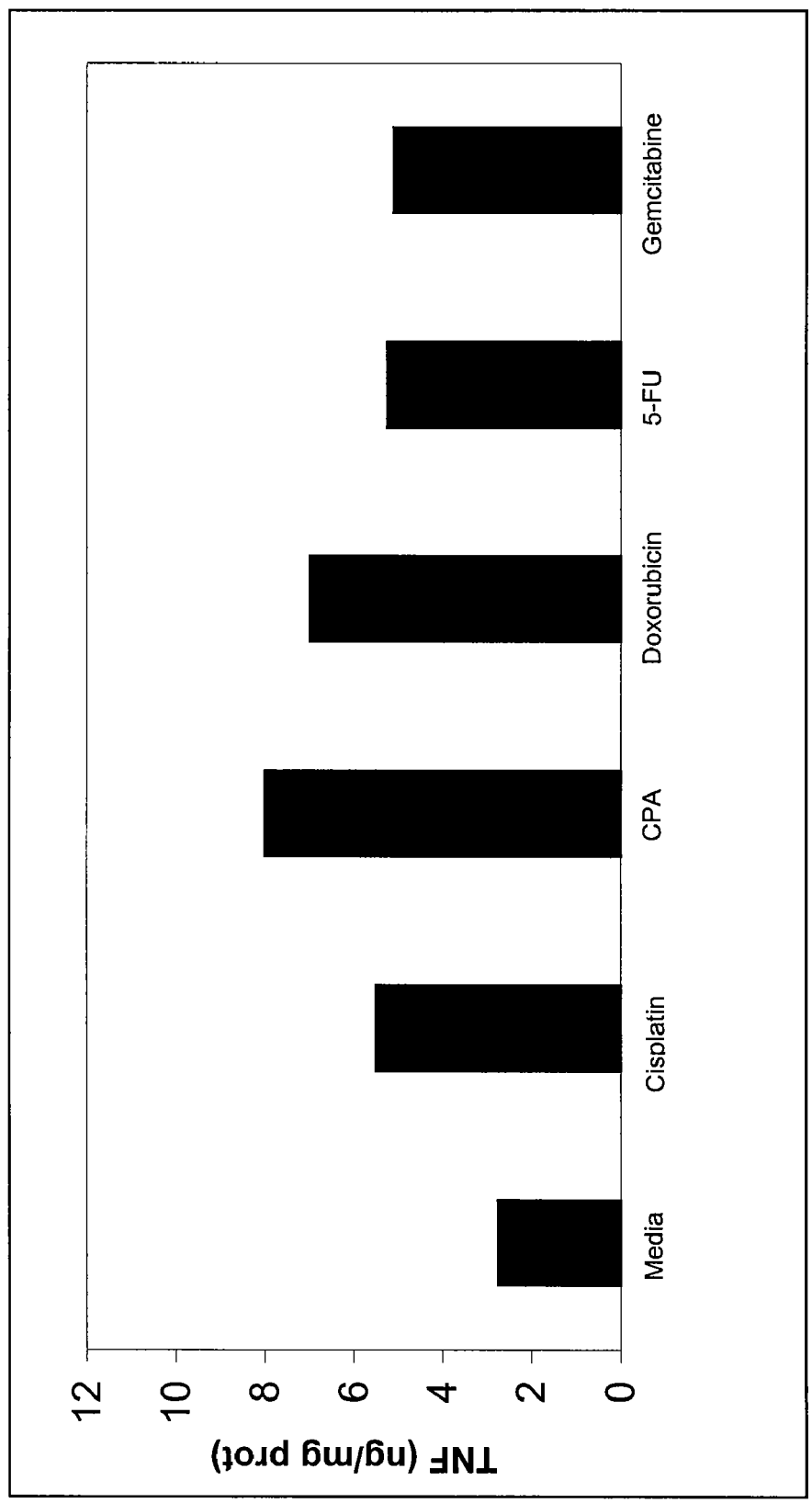
FIG. 13 depicts levels of TNF-α produced in PROb xenografts after delivery of Ad. Egr.TNF.

In vivo study. Compared to vector and NS treated xenografts, agents that induced TNF-α in PC-3 xenographs were cisplatin (3.5-fold), cyclophosphamide (4.4-fold), doxorubicin (3.1-fold) and 5-FU (4.2-fold). See FIG. 12. Vector treated PROb cells demonstrated increased TNF-α levels when given concurrently with cisplatin (1.9-fold), cyclophosphamide (2.8-fold), doxorubicin (2.5-fold), 5-FU (1.9-fold) and gemcitabine (1.8-fold), compared with cells exposed to vector plus NS. See FIG. 13.

Figure 14:
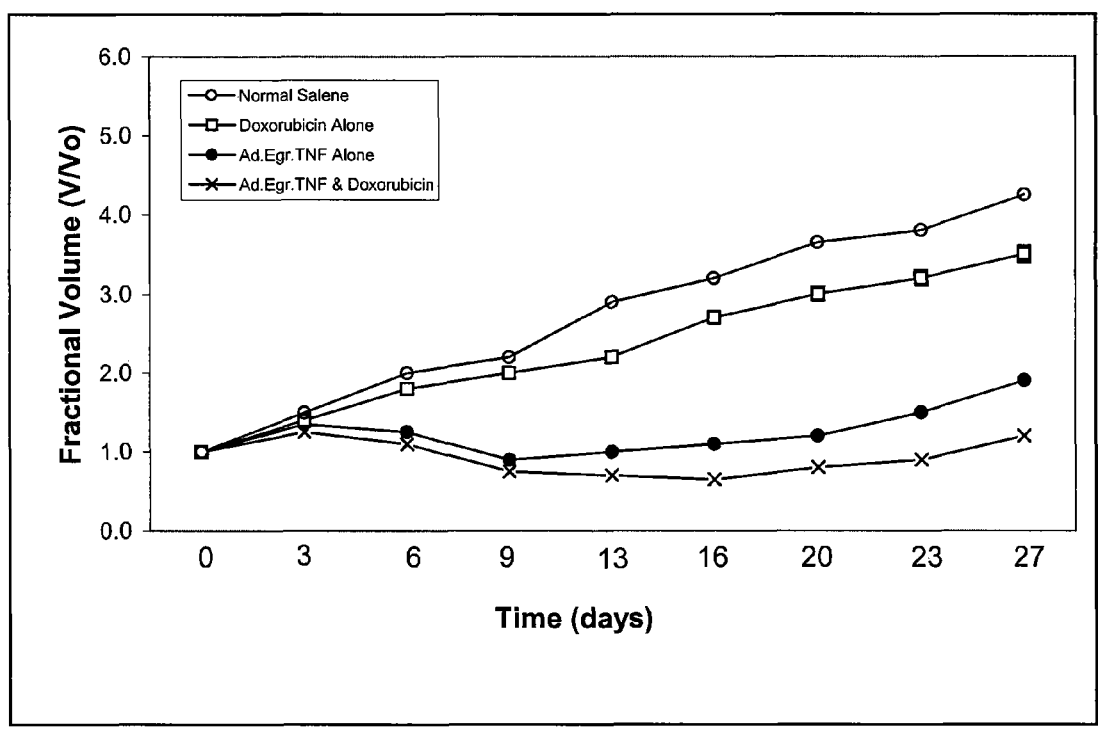
FIG. 14 shows fractional tumor volumes in PC-3 xenografts treated with normal saline (•), doxorubicin alone (o), Ad.Egr.TNF alone (•) or a combination of Ad.Egr.TNF and doxorubicin (x).

Efficacy study. Combined treatment with the vector and doxorubicin resulted in a decrease of tumor volumes when compared to control, doxorubicin alone and the vector alone. See FIG. 14.

Example 8

Chemo-sensitivity of PC-3 and PROb Cells

Percent survival following exposure to Ad.Egr-TNF.11D and chemotherapy was compared with survival in growth media. PC-3 cells demonstrated surviving fractions of 60% (460 μM) and 90% (46 μM) with cisplatin, 30% (300 μM) and 90% (3 μM) with doxorubicin, 20% (200 mM) and 80% (2 mM) with 5-FU and 10% (140 μM) and 80% (1.4 μM) with taxol. PROb demonstrated surviving fractions of 77% (460 μM) and 77% (46 μM) with cisplatin, 85% (300 μM) and 100% (3 μM) with doxorubicin, 38% (200 mM) and 69% (2 mM) with 5-FU and 8% (140 μM) and 85% (1.4 μM) with taxol.

Example 9

Induction of TNF-α Protein

Figure 15A:
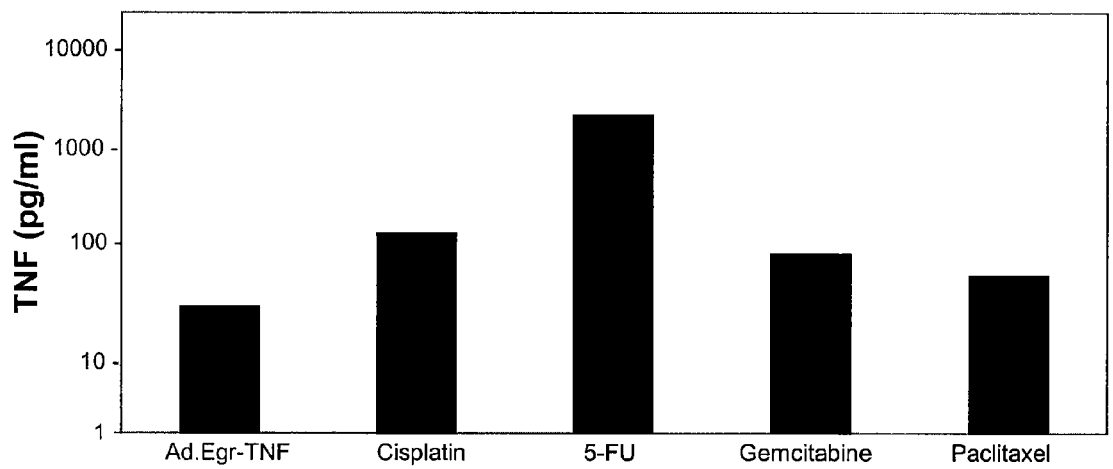
FIGS. 15A & 15B show chemo-induction of TNF-α protein in PC-3 (15A) and PROb (15B) cells for 24 hours measured by ELISA.
Figure 15B:
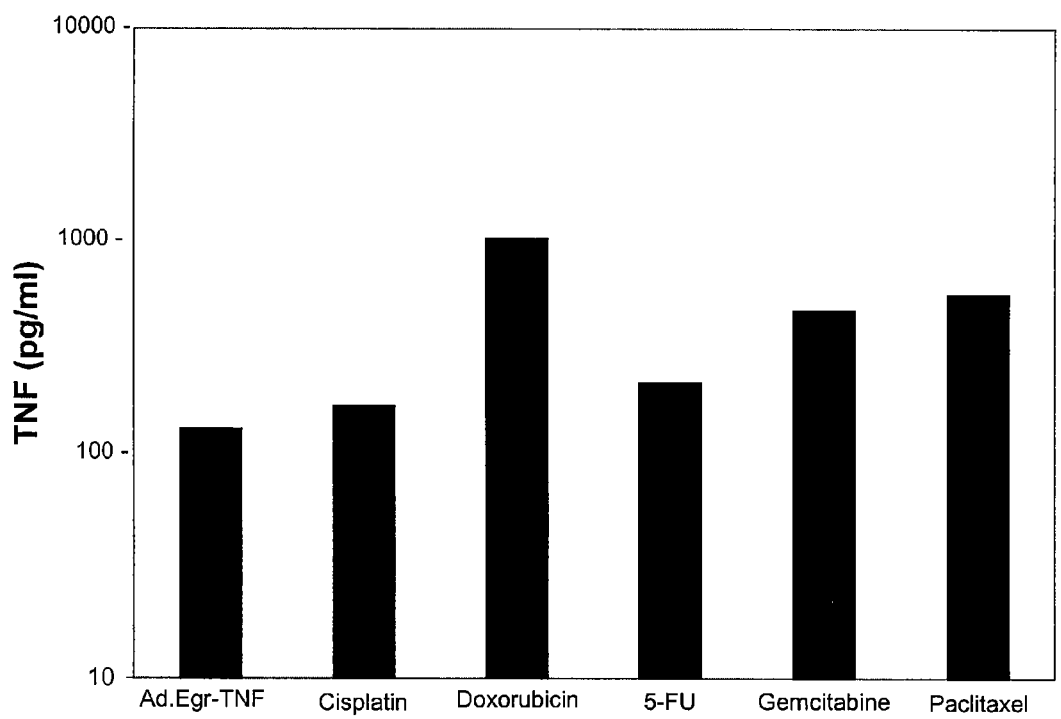

Using an ELISA specific for human TNF-α, TNF-α production was assessed following infection of PC-3 cells and PROb cells with 100 MOI of Ad.Egr-TNF.11D. Neither of these cell lines produced endogenous human TNF-α. In vector-only treated cells, PC-3 cells produced 14 pg/ml of TNF-α and PROb cells produced 130 pg/ml. In vector and chemotherapeutic agent treated cells (cisplatin (250 μM), doxorubicin (3 μM), 5-FU (100 mM), gemcitabine (3 mM) or paclitaxel (14 μM)), PC-3 cells exhibited significant increases in TNF-α levels: cisplatin (3.8-fold), 5-FU (67.4-fold), gemcitabine (2.7-fold) and paclitaxel (1.7-fold). See FIG. 15A. Similarly, PROb cells exhibited significant increases in TNF-α levels: cisplatin (1.3-fold), 5-FU (1.7-fold), gemcitabine (3.5-fold), paclitaxel (4.5-fold) and doxorubicin (7.4-fold). See FIG. 15B. TNF-α induction by doxorubicin in PC-3 cells was not evaluated because it was toxic at the doses used in these experiments, and cyclophosphamide was not investigated because this drug requires hepatic activation.

These data obtained from histologically different neoplastic cell lines demonstrate that Ad.Egr-TNF.11D is activated by different classes of chemotherapeutic agents.

Example 10

N-acetyl Cysteine Alters Induction of TNF-α Protein

Figure 16A:
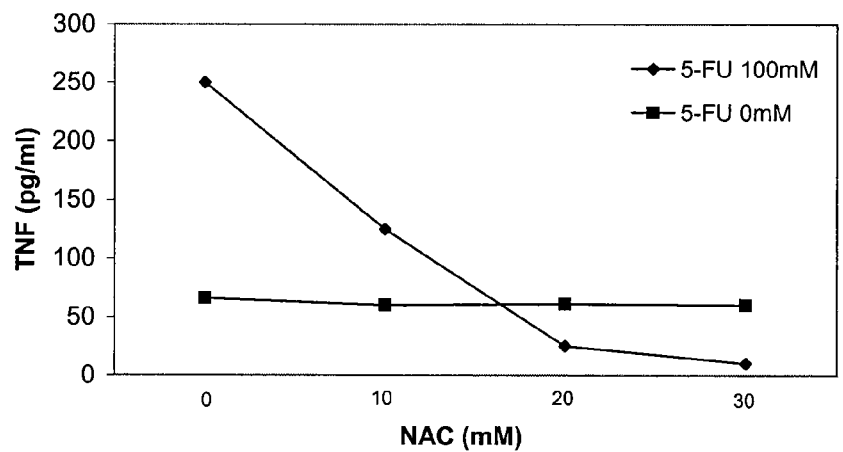
FIGS. 16A & 16B show the effect of N-acetylcysteine ("NAC") on the induction of TNF-α in PC-3 (16A) and PROb (16B) cells.
Figure 16B:
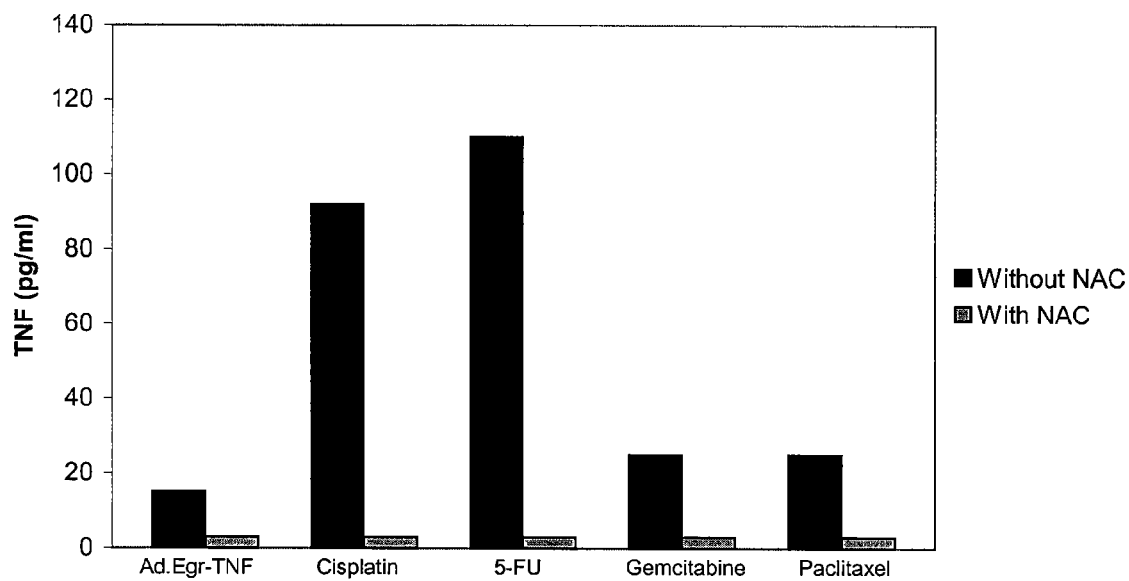

Increasing concentrations of NAC (10 mM to 30 mM) decrease the concentration of TNF-α protein produced by PC-3 cells infected with Ad.Egr-TNF.11D and treated with 100 mM 5-FU, compared with PC-3 cells infected with Ad.Egr-TNF.11D alone. See FIG. 16A. Also, in in vitro chemo-induction experiments, NAC significantly decreased the concentration of TNF-α protein produced by Ad.Egr-TNF.11D transduced PC-3 cells treated with cisplatin, 5-FU, gemcitabine and paclitaxel. See FIG. 16B. NAC also significantly reduced the induction of TNF-α following treatment with 3 μM doxorubicin in PROb cells, and cells treated with cisplatin, 5-FU, gemcitabine or paclitaxel and exposed to NAC (data not shown).

Example 11

In vivo Induction of TNF-α Protein

Figure 17A:
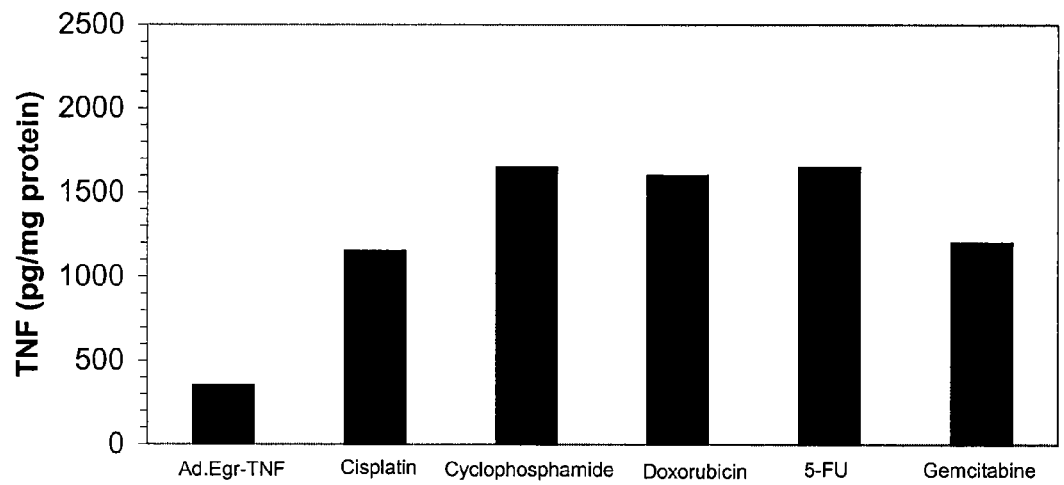
FIGS. 17A & 17B depict in vivo measurement of levels of TNF-α produced in PC-3 (17A) and PROb (17B) xenografts after delivery of Ad. Egr.TNF.

PC-3 Xenografts were injected with Ad.Egr-TNF.11D on days 0 and 1, and chemotherapy was administered on days 1 and 2. Significant increases in human TNF-α levels in the tumors were detected 48 hrs after the second injection of Ad.Egr-TNF.11D. PC-3 tumors injected with Ad.Egr-TNF.11D alone produced 376.33±64.22 pg/mg of TNF-α protein. The combination of Ad.Egr-TNF.11D and chemotherapy produced a significant increase in TNF-α levels following treatment with cisplatin (3.1-fold), cyclophosphamide (4.4-fold), doxorubicin (4.2-fold), 5-FU (4.4-fold) and gemcitabine (3.1-fold). FIG. 17A.

Figure 17B:
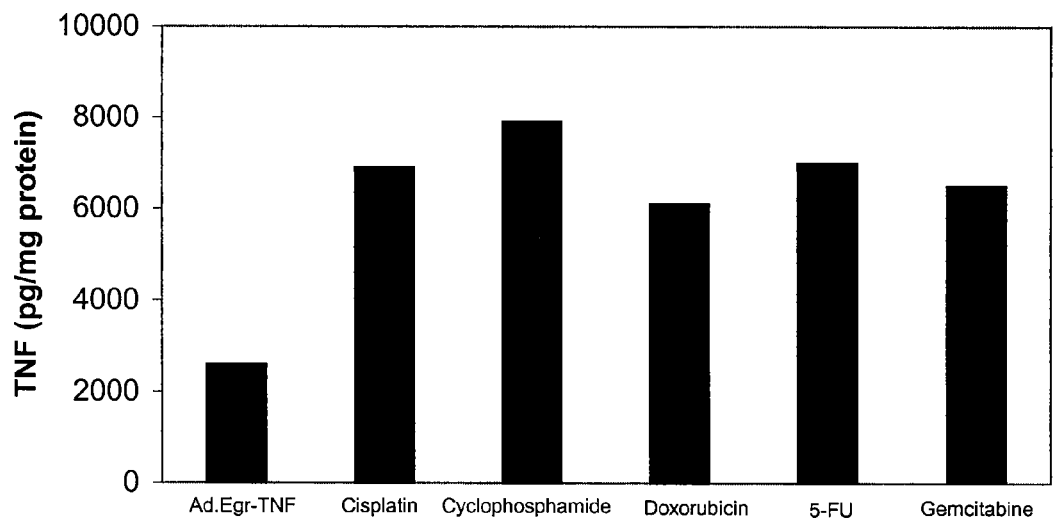

In PROb xenografts, significant induction of TNF-α protein was detected following combined treatment with Ad.Egr-TNF.11D and cisplatin (2.6-fold), cyclophosphamide (3.0-fold), doxorubicin (2.3-fold), 5-FU (1.9-fold) and gemcitabine (2.5-fold) compared to treatment with Ad.Egr-TNF.11D alone. See FIG. 17B. Studies using taxol were not feasible due to severe systemic toxicity at the doses employed in these studies.

These data demonstrate that activation of the Egr-TNF construct is mediated, at least in large part, by ROIs produced by these chemotherapeutic agents, and that, like IR, chemotherapeutic agents induce the production of TNF-α protein by tumors transduced with the Ad.Egr-TNF.11D vector. Although, low levels of TNF-α are produced by the Ad.Egr-TNF vector, toxicity has not been observed in animal or human studies.

Example 12

Xenografts Regrowth Studies

Figure 18A:
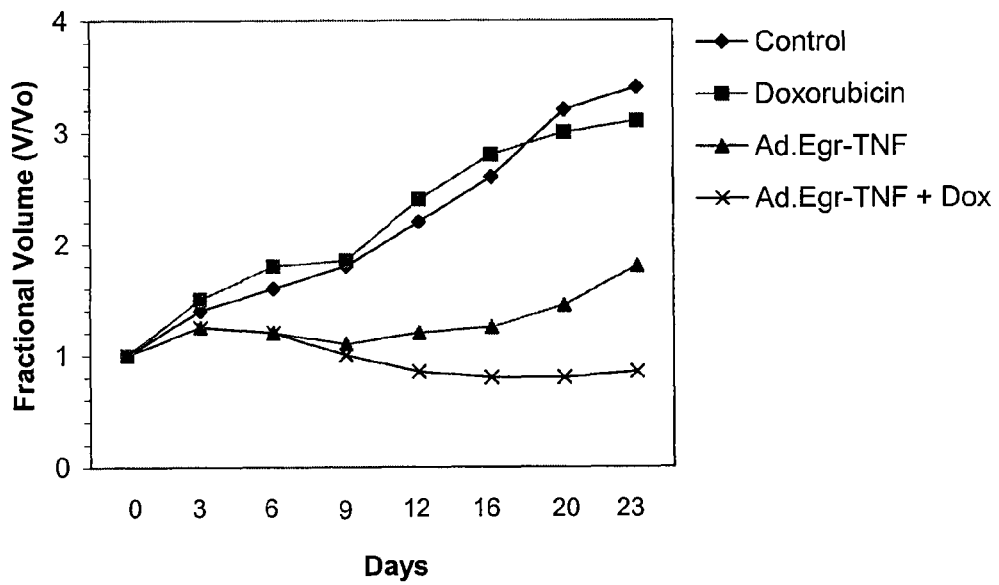
FIGS. 18A & 18B depict xenograft regrowth in PC-3 (18A) and PROb (18B) xenographs.
Figure 18B:
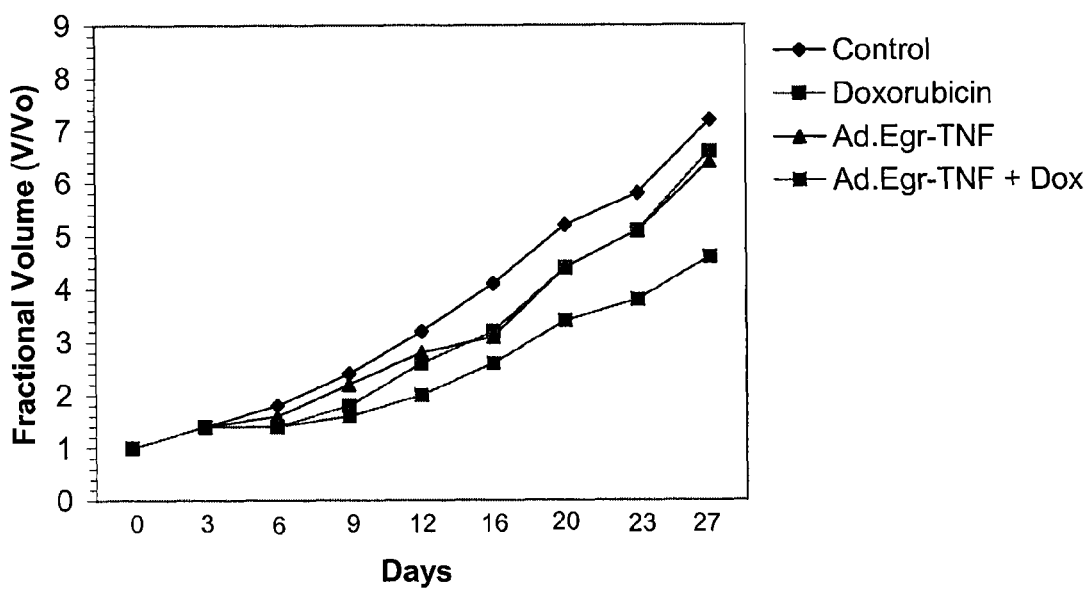

PC-3 tumors (n=59) were injected with Ad.Egr-TNF.11D and mice were treated with doxorubicin. FIGS. 18A-B show combined results of two independent experiments. The control and the doxorubicin-only groups exhibited equivalent tumor growth (3-fold) at day 23, treatment with Ad.Egr-TNF.11D alone significantly reduced mean tumor volume beginning on day 9 and continuing to day 23 compared to the buffer injected control group, and the Ad.Egr-TNF.11D and doxorubicin combination produced the greatest reduction in mean tumor volume (90% reduction) at day 13 that persisted for the duration of the experiment. A significant difference between the Ad.Egr-TNF.11D alone group and the combination group was detectable on day 16 and continued until day 23. See FIG. 18A.

In PROb xenografts, there was no difference in tumor growth delay at day 27 among the buffer injected control, doxorubicin alone and Ad.Egr-TNF.11D alone groups. Notably, treatment with Ad.Egr-TNF.11D and doxorubicin produced a significant reduction in mean fractional tumor volume compared with Ad.Egr-TNF.11D alone at day 23. At day 27, tumors in the Ad.Egr-TNF.11D and doxorubicin group exhibited a 4.9-fold increase in fractional tumor volume compared with a 6.7-fold increase in the Ad.Egr-TNF.11D alone group. See FIG. 18B.

Systemic toxicity, including weight loss and deaths, was observed in groups receiving doxorubicin alone; however, these effects were not increased with the addition of Ad.Egr-TNF.11D.

Example 13

Combined Treatment with AD.EGR-TNF.11D and Doxorubicin Decreases Tumor Microvessel Density PC-3 xenografts (day 27) were obtained following treatment with Ad.Egr-TNF.11D and doxorubicin. Microvessels were visualized in paraffin-embedded tissue sections using anti-CD31 immunohistochemistry and an avidin-biotin peroxidase technique. Combined treatment with Ad.Egr-TNF.11D and doxorubicin reduced the number of vessels per high power field (5.35±0.78) compared with the control group (7.89±0.54), the doxorubicin alone group (6.24±0.35) and the Ad.Egr-TNF.11D alone group (6.5±0.43). In the Ad.Egr-TNF.11D and doxorubicin treatment group there were fewer vessels of all diameters and less branching when compared with tumors from the control, the doxorubicin alone and the Ad.Egr-TNF.11D alone treatment groups. These results indicate that activation of Ad.Egr-TNF.11D enhances treatment with doxorubicin, at least in part, by inhibiting angiogenesis. Taken together, these data suggest that the anti-tumor activity of doxorubicin and Ad.Egr-TNF.11D is mediated by the inhibitory effects of angiostatin and doxorubicin on tumor angiogenesis.

What is claimed is:

1. A method for inducing expression of a polypeptide in a cell, comprising concomitantly contacting the cell with:
   (a) a construct comprising an Egr-1 promoter operably linked to a polynucleotide encoding the polypeptide; and
   (b) at least one DNA damaging chemotherapeutic agent capable of inducing expression from the Egr-1 promoter in the absence of ionizing radiation in an amount effective to induce expression of the polypeptide, wherein expression of the polypeptide is induced.

2. The method of claim 1, wherein the polypeptide comprises TNF-α.

3. The method of claim 1, wherein the DNA damaging chemotherapeutic agent comprises at least one of cisplatin, doxorubicin, cyclophosphamide, 5-fluorouracil, taxol or gemcitabine.

4. The method of claim 1, wherein the cell is contacted with the construct and the DNA damaging chemotherapeutic agent concurrently.

5. The method of claim 1, wherein the polypeptide has anti-tumor activity or an antineoplastic effect.

6. The method of claim 5, wherein the polypeptide is a tumor suppressor, an inducer of apoptosis, an enzyme, a toxin, or a cytokine.

7. The method of claim 5, wherein the DNA damaging chemotherapeutic agent comprises at least one of cisplatin, doxorubicin, cyclophosphamide, 5-fluorouracil, taxol or gemcitabine.

8. A method of inhibiting a neoplastic cell, comprising concomitantly contacting the cell with: (a) a construct, comprising an Egr-1 promoter operably linked to polynucleotide encoding TNF-α; and (b) a one DNA damaging chemotherapeutic agent capable of inducing expression from the Egr-1 promoter in the absence of ionizing radiation in an amount effective to induce expression of TNF-α, wherein the neoplastic cell is inhibited.

9. The method of claim 8, wherein the DNA damaging chemotherapeutic agent comprises at least one of cisplatin, doxorubicin, cyclophosphamide, 5-fluorouracil, taxol or gemcitabine.

10. The method of claim 8, wherein the neoplastic cell is a cell of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow, rectum or kidney.

11. The method of claim 8, further comprising contacting the cell with ionizing radiation.

12. A method of inhibiting or reducing growth of a tumor in a subject, comprising co-administering to the subject: (a) a construct comprising an Egr-1 promoter operably linked to a polynucleotide encoding TNF-α; and (b) a DNA-damaging chemotherapeutic agent capable of inducing expression from the Egr-1 promoter in the absence of ionizing radiation in an amount effective to induce expression of the TNF-α from the Egr-1 promoter, wherein tumor growth is reduced or inhibited.

13. The method of claim 12, wherein the chemotherapeutic agent is cisplatin.

14. The method of claim 13, wherein the cisplatin is administered to the subject in a dosage of about 2 to about 200 mg/m$^2$.

15. The method of claim 12, wherein the chemotherapeutic agent is doxorubicin.

16. The method of claim 15, wherein, the doxorubicin is administered to the subject in a dosage of about 0.6 to about 60 mg/m$^2$.

17. The method of claim 12, wherein the chemotherapeutic agent is cyclophosphamide.

18. The method of claim 17, wherein the cyclophosphamide is administered to the subject in a dosage of about 20 to about 2000 mg/m$^2$.

19. The method of claim 12, wherein the chemotherapeutic agent is 5-fluorouracil.

20. The method of claim 19, wherein the 5-fluorouracil is administered to the subject in a dosage of about 7.5 to about 1000 mg/m$^2$.

21. The method of claim 12, wherein the chemotherapeutic agent is taxol.

22. The method of claim 21, wherein the taxol is administered to the subject in a dosage of about 1.75 to about 175 mg/m$^2$.

23. The method of claim 12, wherein the DNA damaging chemotherapeutic agent is gemcitabine.

24. The method of claim 23, wherein the gemcitabine is administered to the subject in a dosage of about 10 to about 1000 mg/m$^2$.

25. The method of claim 12, wherein the construct is administered to the subject intratumorally.

26. The method of claim 12, wherein the construct is administered to the subject daily, semi-weekly, biweekly or weekly.

27. The method of claim 12, wherein the construct is delivered to the subject in about six doses over a 7 to 70 day period.

28. The method of claim 12, wherein the construct and the DNA damaging chemotherapeutic agent are administered to the subject concurrently.

29. The method of claim 12, wherein the subject is a mammal.

30. The method of claim 29, wherein the mammal is a human.

31. The method of claim 12, wherein the tumor is at least one of lung cancer, prostate cancer, ovarian cancer, testicular cancer, brain cancer, skin cancer, melanoma, colon cancer, rectal cancer, gastric cancer, esophageal cancer, tracheal cancer, head & neck cancer, pancreatic cancer, liver cancer, breast cancer, ovarian cancer, lymphoid cancer, leukemia, cervical cancer, and vulvar cancer.

32. The method of claim 12, the method further comprising administering an adjunct cancer therapy to the subject.

33. The method of claim 32, wherein the adjunct cancer therapy is ionizing radiation or surgery.

* * * * *